United States Patent
Dickhaut et al.

(10) Patent No.: US 11,399,543 B2
(45) Date of Patent: Aug. 2, 2022

(54) SUBSTITUTED 1,2,3,5-TETRAHYDROIMIDAZO [1,2-A]PYRIMIDINIUMOLATES FOR COMBATING ANIMAL PESTS

(71) Applicant: BASF SE, Ludwigshafen am Rhein (DE)

(72) Inventors: Joachim Dickhaut, Ludwigshafen (DE); Olesya Kuzmina, Ludwigshafen (DE); Ashokkumar Adisechan, Navi Mumbai (IN); Gopal Krishna Datta, Goettingen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/652,700

(22) PCT Filed: Oct. 10, 2018

(86) PCT No.: PCT/EP2018/077583
§ 371 (c)(1),
(2) Date: Apr. 1, 2020

(87) PCT Pub. No.: WO2019/072906
PCT Pub. Date: Apr. 18, 2019

(65) Prior Publication Data
US 2020/0236941 A1 Jul. 30, 2020

(30) Foreign Application Priority Data
Oct. 13, 2017 (EP) .................................. 17196408

(51) Int. Cl.
*A61K 31/519* (2006.01)
*C07D 487/04* (2006.01)
*A01N 43/90* (2006.01)

(52) U.S. Cl.
CPC ........... *A01N 43/90* (2013.01); *C07D 487/04* (2013.01)

(58) Field of Classification Search
CPC ........................... A61K 31/519; C07D 487/04
USPC ........................................ 514/259.5; 544/281
See application file for complete search history.

(56) References Cited

U.S. PATENT DOCUMENTS

2016/0066577 A1   3/2016   Zhang et al.

FOREIGN PATENT DOCUMENTS

| EP | 3601298 A1 | 2/2020 | |
|---|---|---|---|
| WO | WO-2009/099929 A1 | 8/2009 | |
| WO | WO-2011/017347 A2 | 2/2011 | |
| WO | WO-2014/167084 A1 | 10/2014 | |
| WO | WO-2018/177970 A1 | 10/2018 | |
| WO | WO-2018/202654 A1 | 11/2018 | |
| WO | WO-2018/229202 A1 | 12/2018 | |
| WO | WO-2018/234202 A1 | 12/2018 | |
| WO | WO-2019/042932 A1 | 3/2019 | |
| WO | WO-2019/043183 A1 | 3/2019 | |
| WO | WO-2019072906 A1 * | 4/2019 | .......... C07D 487/04 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
European Search Report for EP Patent Application No. 17196408.3, dated Apr. 9, 2018, 4 pages.
International Application No. PCT/EP2018/077583, International Search Report and Written Opinion, dated Dec. 11, 2018.

* cited by examiner

*Primary Examiner* — Douglas M Willis
(74) *Attorney, Agent, or Firm* — Marshall, Gerstein & Borun LLP

(57) ABSTRACT

The invention relates to compounds of formula (I): wherein the variables are defined in the specification. The invention also relates to a pesticidal mixture comprising a compound of formula (I), and another agrochemically active ingredient; and to an agrochemical or veterinary composition comprising a compound of formula (I) or the pesticidal mixture, and a liquid or solid carrier. It also relates to uses and methods of application for controlling invertebrate pests, or for protecting plants from infestation by invertebrate pests by application of compounds of formula (I), or of the pesticidal mixture. It also relates to seeds comprising a compound of formula (I) or the pesticidal mixture in certain amounts.

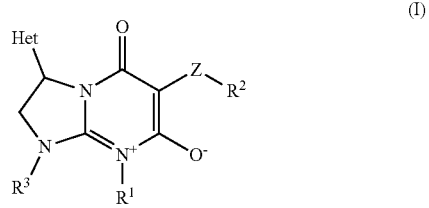

(I)

22 Claims, No Drawings

SUBSTITUTED 1,2,3,5-TETRAHYDROIMIDAZO [1,2-A]PYRIMIDINIUMOLATES FOR COMBATING ANIMAL PESTS

The present invention relates to insecticidal substituted imidazoline pyrimidinium compounds and/or to the compositions comprising such compounds for combating invertebrate pests. The invention also relates to pesticidal methods, to uses and to applications of substituted imidazoline pyrimidinium compounds as described in the present invention and the stereoisomers, salts, tautomers and N-oxides thereof as well as compositions comprising them.

Invertebrate pests and in particular insects, arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes.

It is therefore an object of the present invention to provide compounds having a good pesticidal activity and showing a broad activity spectrum against a large number of different invertebrate pests, especially against difficult to control insects, arachnids and nematodes.

It has been found that these objectives can be achieved by substituted imidazoline pyrimidinium compounds of formula (I), as defined below, including their stereoisomers, their salts, in particular their agriculturally or veterinary acceptable salts, their tautomers and their N-oxides.

The invention provides substituted imidazoline-pyrimidinium compounds of formula (I)

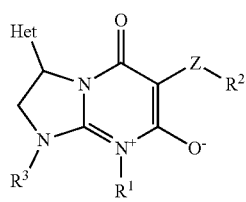

(I)

wherein

Z is a direct bond, O, $S(O)_m$, $NR^b$, $C(R^a R^{aa})O$, $C(=X^1)$, $C(=X^1)Y^1$, or $Y^1C(=X^1)$;

$X^1$ is O, S, or $NR^b$;

$Y^1$ is O, S, or $NR^c$;

Het is a three- to ten-membered heterocyclic ring, or a seven- to eleven-membered heterocyclic ring system, wherein the ring or ring system contains up to four ring members independently selected from O, S, and $N(R^c)_p$ with the proviso that up to two ring members are O, up to two ring members are S, and up to four ring members are $N(R^c)_p$, and wherein up to 3 carbon atom ring members are independently replaced by C(=O) and C(=S), wherein the S-ring members are independently replaced by $S(=O)_o(=NR^b)_q$, and wherein each ring or ring system is unsubstituted or substituted with up to five $R^a$;

o, q are each independently 0, 1 or 2, provided that the sum (o+q) is 0, 1 or 2 for each ring;

$R^1$, $R^3$ are independently H;
$C_1$-$C_8$-alkyl, $C_2$-$C_8$-alkenyl, $C_2$-$C_8$-alkynyl, $C_3$-$C_{10}$-cycloalkyl, $C_4$-$C_{10}$-cycloalkenyl, $C_5$-$C_{14}$-cycloalkylcycloalkyl, which groups are unsubstituted, or partially, or fully substituted with $R^a$; or a three- to eleven-membered saturated, partially unsaturated, or aromatic carbo-, or heterocyclic ring or ring system, which ring or ring system is unsubstituted, partially, or fully substituted with $R^a$, and wherein the heterocyclic ring or ring system contains 1 to 4 ring members independently selected from $N(R^c)_p$, O, and S, wherein S is non-oxidized or oxidized; or $C(=O)R^b$, $C(=O)OR^e$, $NR^bR^c$, $C(=O)NR^bR^c$, $C(=S)NR^bR^c$, $SO_2NR^bR^c$, $OC(=O)R^c$, $OC(=O)OR^e$, $OC(=O)NR^bR^e$, $N(R^c)C(=O)R^c$, $N(R^c)C(=O)OR^e$, $N(R^c)C(=O)NR^bR^c$, $NR^cSO_2R^b$, $NR^cSO_2NR^bR^c$, $Si(R^d)_3$, $C(=NR^c)R^c$, $C(=NOR^c)R^c$, $C(=NNR^bR^c)R^c$, $C(=NN(C(=O)R^b)R^c)R^c$, $C(=NN(C(=O)OR^c)(R^c)_2$, $S(=O)_o(=NR^b)_qR^c$ or $N=CR^bR^c$;

$R^a$ is each independently halogen, CN, $OR^e$, $NR^bR^c$, $NO_2$, $C(=O)(O)_pR^c$, $OC(=O)(O)_pR^e$, $C(=O)NR^b R^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $N=S(=O)_pR^cR^c$, $S(=O)_o(=NR^b)_qR^c$, $SF_5$, OCN, SCN, $Si(R^d)_3$;

$C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, which groups are unsubstituted, partially or fully substituted with $R^{aa}$;

a three- to six-membered saturated, or partially unsaturated or aromatic carbo- or heterocyclic ring, which ring is unsubstituted, partially, or fully substituted with $R^{aa}$, wherein the heterocyclic ring contains 1 to 3 ring members independently selected from $N(R^c)_p$, O, and S, wherein S is unoxidized or oxidized;

or two geminally bound groups $R^a$ together may form a group selected from =O, =S, =$CR^bR^c$, =$NR^c$, =$NOR^c$, and =$NNR^cR^c$;

$R^{aa}$ is each independently halogen, $C_1$-$C_6$-alkyl, $C_1$-$C_6$-haloalkyl, $C_1$-$C_6$-alkoxy or $C_1$-$C_6$-haloalkoxy;

$R^b$ is each independently H;
$C_1$-$C_6$-alkyl, $C_1$-$C_6$-haloalkyl, $C_1$-$C_6$-alkoxy, $C_1$-$C_6$-haloalkoxy, which groups are unsubstituted, partially or fully substituted with $R^{aa}$; or a three- to six-membered saturated, or partially unsaturated or aromatic carbo- or heterocyclic ring, which ring is unsubstituted, partially, or fully substituted with $R^{aa}$, wherein the heterocyclic ring contains 1 to 3 ring members independently selected from $N(R^c)_p$, O, and S, wherein S is non-oxidized or oxidized;

$R^b$ is each independently H;
$C_1$-$C_4$-alkyl, $C_1$-$C_4$-haloalkyl, $C_1$-$C_4$-alkylcarbonyl, or $C_1$-$C_6$ cycloalkyl; or a three- to six-membered saturated, partially unsaturated or aromatic carbo- or heterocyclic ring, which ring is unsubstituted, partially, or fully substituted with $R^{aa}$, wherein the heterocyclic ring contains 1 to 3 ring members independently selected from $N(R^c)_p$, O, and S, wherein S is non-oxidized or oxidized;

wherein two geminally bound groups $R^bR^b$, $R^cR^b$ or $R^cR^c$ together with the atom to which they are bound, may form a 3-, 4-, 5-, 6- or 7-membered saturated, partially unsaturated or aromatic carboor heterocyclic ring, which ring is unsubstituted, partially or fully substituted with $R^{bb}$, and wherein the heterocyclic ring contains 1 to 2 ring members independently selected from N, O, S, NO, SO and $SO_2$;

$R^d$ is each independently H;
phenyl, $C_1$-$C_6$-alkyl, $C_2$-$C_6$-alkenyl, $C_2$-$C_6$-alkynyl, $C_3$-$C_8$-cycloalkyl, or $C_1$-$C_6$-alkoxyalkyl, which groups are unsubstituted, or substituted with one or more, same or different halogen;

$R^e$ is each independently, $C_1$-$C_4$-alkyl, $C_1$-$C_4$-haloalkyl, $C_1$-$C_4$-alkylcarbonyl, $C_1$-$C_6$ cycloalkyl; or
a three- to six-membered saturated, partially unsaturated or aromatic carbo- or heterocyclic ring, which ring may be unsubstituted, partially, or fully substituted with $R^{aa}$, wherein the heterocyclic ring contains 1 to 3 ring members independently selected from $N(R^{aa})_p$, O and S, and wherein S is non-oxidized or oxidized;

m is 0, 1, or 2;
p is 0 or 1;
$R^2$ is H, halogen, CN;
$C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, or $C_3$-$C_6$ cycloalkenyl, which groups are unsubstituted, partially, or fully substituted with $R^{2a}$; or
a carbo- or heterocyclic three- to ten-membered ring or a seven- to eleven-membered rings system, which ring or ring system may be saturated, partially unsaturated, or aromatic, and is unsubstituted, partially, or fully substituted with $R^{2a}$, wherein the heterocyclic ring or ring system contains 1 to 4 ring members independently selected from $N(R^c)_p$, O, and S, wherein S is non-oxidized or oxidized; with the proviso that if $R^2$ is halogen or CN, then Z is a direct bond;

$R^{2a}$ is each independently halogen, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF^5$, OCN, SCN, $Si(R^d)_3$, $C(=N(O)_pR^b)R^b$, $C(=NNR^bR^c)R^b$, $C(=NN(C(=O)_pR^c)R^c)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, $N=S(=O)_pR^cR^c$; $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, which groups are unsubstituted, partially, or fully substituted with $R^{2aa}$; or
or a three- to six-membered saturated, or partially unsaturated or aromatic carbo- or heterocyclic ring, which ring is unsubstituted, partially, or fully substituted with $R^{2aa}$, and wherein the heterocyclic ring contain 1 to 3 ring members independently selected from $N(R^c)_p$, O, and S, wherein S is non-oxidized or oxidized; or
two geminally bound groups $R^{2a}$ together may form a group selected from =O, =S, =$CR^bR^c$, =$NR^c$, =$NOR^c$, and =$NNR^cR^c$;

$R^{2aa}$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF^5$, OCN, SCN, $Si(R^d)_3$, $C(=N(O)_pR^b)R^b$, $C(=NNR^bR^c)R^b$, $C(=NN(C(=O)O_pR)R^b)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, or $N=S(=O)_pR^cR^c$ or
two geminally bound groups $R^{2aa}$ together may form a group selected from =O, =S, =$CR^bR^c$, =$NR^c$, =$NOR^c$, and =$NNR^cR^c$;

$X^2$ is independently O or S;

$R^{bb}$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF^5$, OCN, SCN, $Si(R^d)_3$, $C(=N(O)_pR^b)R^b$, $C(=NNR^bR^c)R^b$, $C(=NN(C(=O)O_pR)R^b)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, or $N=S(=O)_pR^cR^c$ or
two geminally bound groups $R^{bb}$ together may form a group selected from =O, =S, =$CR^bR^c$, =$NR^c$, =$NOR^c$, and =$NNR^cR^c$;

and/or stereoisomers or agriculturally or veterinary acceptable salts or tautomers or N-oxides thereof.

Compounds of formula (I) are novel. WO2014/167084 generally discloses substituted bicyclic pyrimidinium compounds and their insecticidal properties. WO2011/017347 discloses pyrimidinium compounds, as well as their activity against invertebrate pests. EP-application 17164175.6 discloses S-containing pyrimidinium compounds for combating animal pests.

The imidazolinone pyrimidinium compounds of formula (I) and their agriculturally acceptable salts are highly active against animal pest, i.e. harmful arthropods and nematodes, especially against insects and acaridae which are difficult to control by other means.

Moreover, the present invention relates to and includes the following embodiments:

pesticidal mixtures comprising at least one compound of formula (I) as defined above and another agrochemically active ingredient.

compositions comprising at least one compound of formula (I) as defined above;

agricultural or veterinary compositions comprising an amount of at least one compound of formula (I) and a liquid or solid carrier;

a method for controlling invertebrate pests, infestation, or infection by invertebrate pests, preferably wherein the invertebrate pests are insects or nematodes, more preferably insects, comprising contacting the pests, their food supply, habitat, breeding grounds or their locus with a compound of formula (I) as defined above, or the pesticidal mixture.

a method for preventing or protecting against invertebrate pests, preferably against insects or nematodes, more preferably against insects, comprising contacting the invertebrate pests, or their food supply, habitat or breeding grounds with a compound of formula (I) as defined above or the pesticidal mixture;

a method of protecting plants from attack or infestation by invertebrate pests, preferably from insects or nematodes, more preferably from insects, comprising contacting the plant, or the soil or water in which the plant is growing, with a pesticidally effective amount of a compound of formula (I) as defined above or the pesticidal mixture.

a method for protection of plant propagation material comprising contacting the plant propagation material with a compound of formula (I) as defined above or the pesticidal mixture in pesticidally effective amounts.

seed comprising a compound of formula (I) as defined above, or the pesticidal mixture in an amount of from 0.1 g to 10 kg per 100 kg of seed;

The use of compounds of formula (I) as defined above, or of the pesticidal mixture, for combating invertebrate pests, preferably for combating insects and nematodes, more preferably for combating insects.

a non-therapeutic method for treating animals infested or infected by parasites or preventing animals of getting infected or infested by parasites or protecting animals against infestation or infection by parasites which comprises orally, topically or parenterally administering or applying to the animals a parasiticidally effective amount of a compound of formula (I) as defined above or the pesticidal mixture;

a method for treating, controlling, preventing or protecting animals against infestation or infection by parasites by administering or applying orally, topically or parenterally to the animals a compound of formula (I) as defined above or the pesticidal mixture;

the use of the compounds of formula (I) as defined above for protecting growing plants or plant propagation material from attack or infestation by invertebrate pests, preferably by insects or nematodes, more preferably from insects;

the use of compounds of formula (I) for combating parasites in and on animals;

a process for the preparation of a veterinary composition for treating, controlling, preventing or protecting animals against infestation or infection by parasites which comprises adding a parasiticidally effective amount of an compound of formula (I) or the enantiomers, diastereomers and/or veterinary acceptable salt thereof to a carrier composition suitable for veterinary use;

the use of a compound of formula (I) or the enantiomers, diastereomers and/or veterinary acceptable salt thereof for the preparation of a medicament for treating, controlling, preventing or protecting animals against infestation or infection by parasites.

All the compounds of the present invention including if applicable their stereoisomers, their tautomers, their salts or their N-oxides as well as compositions thereof are particularly useful for controlling invertebrate pests, in particular for controlling arthropods and nematodes and especially insects. Therefore, the invention relates to the use of a compound of formula (I), for combating or controlling invertebrate pests, in particular invertebrate pests of the group of insects, arachnids or nematodes.

The term "compound(s) according to the invention" or "compound(s) of formula (I)" as used in the present invention refers to and comprises the compound(s) as defined herein and/or stereoisomer(s), salt(s), tautomer(s) or N-oxide(s) thereof. The term "compound(s) of the present invention" is to be understood as equivalent to the term "compound(s) according to the invention", therefore also comprising stereoisomer(s), salt(s), tautomer(s) or N-oxide(s) of compounds of formula (I). The terms "pesticidal mixture", "composition(s) according to the invention" or "composition(s) of the present invention" encompasses composition(s) comprising at least one compound of formula (I) according to the invention as defined above, therefore also including a stereoisomer, an agriculturally or veterinary acceptable salt, tautomer or an N-oxide of the compounds of formula (I).

The compounds of the formula (I) are present in mesomeric forms. These forms may be expressed in different isoelectronic formulae, each having the formal positive and negative charges on different atoms (as shown below). The present invention extends to all representative isoelectronic structures of compounds of formula I:

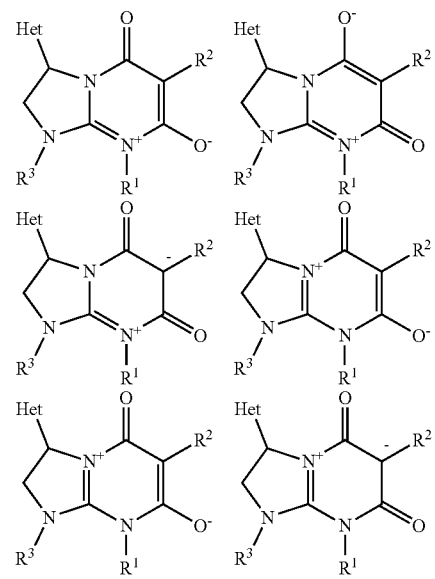

The compounds of the formula (I) have one or, depending on the substitution pattern, more centers of chirality, in which case they are present as mixtures of enantiomers or diastereomers. The invention provides both the single pure enantiomers or pure diastereomers of the compounds of formula (I), and their mixtures and the use according to the invention of the pure enantiomers or pure diastereomers of the compound of formula (I) or its mixtures. Suitable compounds of the formula (I) also include all possible geometrical stereoisomers (cis/trans isomers) and mixtures thereof. Cis/trans isomers may be present with respect to an alkene, carbon-nitrogen double-bond or amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula (I), i.e. to single enantiomers or diastereomers, as well as to mixtures thereof. Preferred embodiments of specific enantiomers are described in more detail below, as compounds of formula (I-R) and (I-S).

Depending on the substitution pattern, the compounds of the formula (I) may be present in the form of their tautomers. Hence the invention also relates to the tautomers of the formula (I) and the stereoisomers, salts, tautomers and N-oxides of said tautomers.

Salts of the compounds of the formula (I) are preferably agriculturally and/or veterinary acceptable salts. They can be formed in a customary method, e.g. by reacting the compound with an acid of the anion in question if the compound of formula (I) has a basic functionality or by reacting an acidic compound of formula (I) with a suitable base.

Suitable agriculturally or veterinary useful salts are especially the salts of those cations or the acid addition salts of those acids whose cations and anions, respectively, do not have any ad-verse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The term "N-oxide" includes any compound of the present invention which has at least one tertiary nitrogen atom that is oxidized to an N-oxide moiety.

The organic moieties groups mentioned in the above definitions of the variables are—like the term halogen—collective terms for individual listings of the individual group members. The prefix $C_n$-$C_m$ indicates in each case the possible number of carbon atoms in the group. "Halogen" will be taken to mean F, Cl, Br, and I, preferably Cl.

The term "substituted with", e.g. as used in "partially, or fully substituted with" means that one or more, e.g. 1, 2, 3, 4 or 5 or all of the hydrogen atoms of a given radical have been replaced by one or more, same or different substituents, such as a halogen, in particular F or Cl.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted with fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl. Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen (or sulfur linkages, respectively) at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio. Accordingly, the terms "$C_n$-$C_m$-haloalkoxy" and "$C_n$-$C_m$-haloalkylthio" (or $C_n$-$C_m$-haloalkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethyl-thio, bromomethylthio, dichloromethylthio, trichloromethylthio, fluoromethylthio, difluoromethyl-thio, trifluoromethylthio, chlorofluoromethylthio, dichlorofluoromethylthio, chlorodifluoromethyl-thio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_n$-$C_m$-alkoxy-$C_n$-$C_m$-alkyl" as used herein refers to alkyl having n to m carbon atoms, e.g. like specific examples mentioned above, wherein one hydrogen atom of the alkyl radical is replaced by an $C_n$-$C_m$-alkoxy group; wherein the value of n and m of the alkoxy group are independently chosen from that of the alkyl group.

The suffix "-carbonyl" in a group or "C(=O)" denotes in each case that the group is bound to the remainder of the molecule via a carbonyl C=O group. This is the case e.g. in alkylcarbonyl, haloalkylcarbonyl, aminocarbonyl, alkylaminocarbonyl, dialkylaminocarbonyl, alkoxycarbonyl, haloalkoxycarbonyl.

The term "aryl" as used herein refers to a mono-, bi- or tricyclic aromatic hydrocarbon radical such as phenyl or naphthyl, in particular phenyl (also referred as to $C_6H_5$ as subsitituent).

The term "ring system" denotes two or more directly connected rings.

The term "$C_3$-$C_m$-cycloalkyl" as used herein refers to a monocyclic ring of 3- to m-membered saturated cycloaliphatic radicals, e.g. cyclopropyl, cyclobutyl, cyclopentyl, cyclohexyl, cycloheptyl, cyclooctyl and cyclodecyl.

The term "alkylcycloalkyl" denotes as well as the term "alkyl which may be substituted with cycloalkyl" an alkyl group which is substituted with a cycloalkyl ring, wherein alkyl and cycloakyl are as herein defined.

The term "cycloalkylalkyl" denotes as well as the term "cycloalkyl which may be substituted with alkyl" a cycloalkyl ring which is substituted with an alkyl group, wherein alkyl and cycloakyl are as herein defined.

The term "alkylcycloalkylalkyl" denotes as well as the term "alkylcycloalkyl which may be substituted with alkyl" an alkylcycloalkyl group which is substituted with an alkyl, wherein alkyl and alkylcycloakyl are as herein defined.

The term "$C_3$-$C_m$-cycloalkenyl" as used herein refers to a monocyclic ring of 3- to m-membered partially unsaturated cycloaliphatic radicals.

The term "cycloalkylcycloalkyl" denotes as well as the term "cycloalkyl which may be substituted with cycloalkyl" a cycloalkyl substitution on another cycloalkyl ring, wherein each cycloalkyl ring independently has from 3 to 7 carbon atom ring members and the cycloalkyls are linked through one single bond or have one common carbon atom. Examples of cycloalkylcycloalkyl include cyclopropylcyclopropyl (e.g. 1,1'-bicyclopropyl-2-yl), cyclohexylcyclohexyl wherein the two rings are linked through one single common carbon atom (e.g. 1,1'-bicyclohexyl-2-yl), cyclohexylcyclopentyl wherein the two rings are linked through one single bond (e.g. 4-cyclopentylcyclohexyl) and their different stereoisomers such as (1R,2S)-1,1'-bicyclopropyl-2-yl and (1R,2R)-1,1'-bicyclopropyl-2-yl.

The term "3- to 6-membered carbocyclic ring" as used herein refers to cyclopropane, cyclobutane, cyclopentane and cyclohexane rings.

The term "3-, 4-, 5-, 6- or 7-membered saturated, partially unsaturated or aromatic heterocyclic ring which may contain 1, 2, 3 or 4 heteroatoms" or "containing heteroatom groups", wherein those heteroatom(s) (group(s)) are selected from N (N-substituted groups), O and S (S-substituted groups) as used herein refers to monocyclic radicals, the monocyclic radicals being saturated, partially unsaturated or aromatic (completely unsaturated). The heterocyclic radical may be attached to the remainder of the molecule via a carbon ring member or via a nitrogen ring member.

Examples of 3-, 4-, 5-, 6- or 7-membered saturated heterocyclyl or heterocyclic rings include: oxiranyl, aziridinyl, azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin 5 yl, 1,2,4-thiadiazolidin-3-yl, 1,2,4-thiadiazolidin-5-yl, 1,2,4-triazolidin-3-yl,-1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl or heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3 yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7 tetrahydro[1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples of 5- or 6-membered aromatic heterocyclic (hetaryl) or heteroaromatic rings are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

A "$C_2$-$C_m$-alkylene" is divalent branched or preferably unbranched saturated aliphatic chain having 2 to m, e.g. 2 to 7 carbon atoms, for example $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$.

The compounds of formula (I) can be prepared in analogy to the compounds described in WO2014/167084.

In particular, compounds of formula (I) can be prepared analogously to the methods described in WO2009/099929 (pp. 46-54), e.g. by reaction of appropriately substituted compounds of formula (II) with compounds of formula (III).

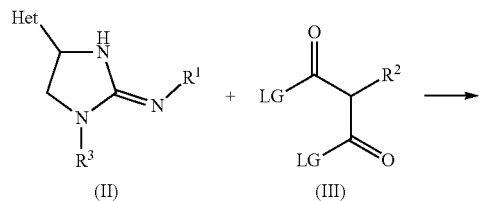

(II)     (III)

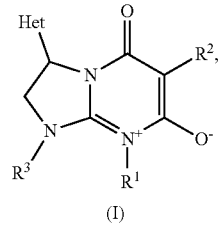

(I)

wherein each LG is independently a leaving group and all other variables have a meaning as defined for compounds of formula (I). Suitable leaving groups include halogen (e.g. Cl), alcoholates (e.g. $CH_3O$), pentafluorophenyl, or 1,3,5-trichlorophenyl. Alternatively, compounds of formula (III) may be applied in the form of their free acid, i.e. wherein LG is OH, wherein an activating agent or a coupling agent is added to the reaction mixture containing compounds of formula (II) and compounds of formula (III), or wherein the activating agent is added to compound of formula (III) before compound of formula (II) are added.

Suitable activating agents are halogenating agents, which are usually selected from chlorinating agents and brominating agents, such as oxalylchloride, thionylchloride, phosphortri- and pentabromide, phorphortri- and pentachloride, preferably from thionylchloride and oxalylchloride. Suitable coupling agents are selected from carbodiimides, such as DCC (dicyclohexylcarbodiimide) and DIC (diisopropylcarbodiimide), benzotriazole derivatives, such as HATU (O-(7-azabenzotriazol-1-yl)-N,N,N',N'-tetramethyluronium hexafluorophosphate), HBTU ((Obenzotriazol-1-yl)-N,N,N',N'-tetramethyluronium hexafluorophosphate) and HCTU (1H-benzotriazolium-1-[bis(dimethylamino)methylene]-5-chloro tetrafluoroborate) and phosphonium-derived activators, such as BOP ((benzotriazol-1-yloxy)-tris(dimethylamino) phosphonium hexafluorophosphate), PyBOP ((benzotriazol-1-yloxy)-tripyrrolidinphosphonium hexafluorophosphate) and PyBrOP (bromotripyrrolidinphosphonium hexafluorophosphate).

Compounds of formula (III) are commercially available and can be prepared as described in Shabanov A. L. et al., Russian Journal of Organic Chemistry, 2009, p. 26-29; Journal of Organic Chemistry, 2002, p. 269-272; or in IP.com, vol. 13 (12B), 2013, p. 1-4.

Compounds of formula (II) can be prepared by reaction of compounds of formula (IV) with compounds of formula (V)

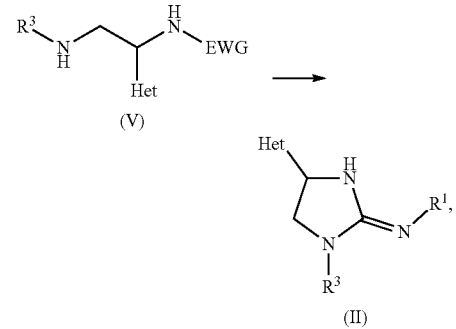

wherein EWG is an electron-withdrawing-group (e.g. tert-butyl sulfonyl), and wherein all other variables have a meaning as defined for compounds of formula (I).

Compounds of formula IV are commercially available. Compounds of formula (V) are available by hydrogenation or reduction and deprotection of compounds of formula (VI).

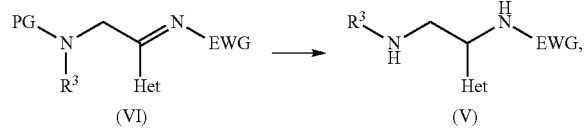

wherein PG is a protective group, EWG is an electron withdrawing group, and all other variables have a meaning as defined for compounds of formula (I). Hydrogenation or reduction may be performed with $H_2$-gas in the presence of a catalyst, or by addition of a metal hydride, e.g. $NaBH_4$.

Compounds of formula (VI) are available by a condensation reaction of compounds of formula (VII) with tert-butyl sulfinylamide in the presence of a lewis catalyst.

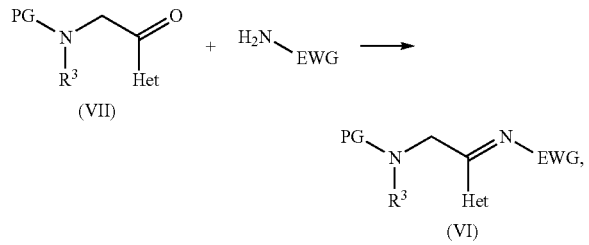

wherein PG is a protective group, EWG is an electron withdrawing group, and all other variables have a meaning as defined for compounds of formula (I).

Compounds of formula (VII) may be prepared by a reaction of Weinreb-amide VIII with HetMgCl.

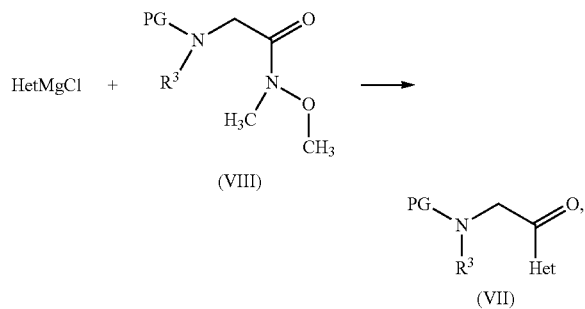

wherein PG is a protective group, and all other variables have a meaning as defined for compounds of formula (I). HetMgCl can be prepared by Br/Mg exchange reaction of Het(Br)Cl or magnesiation reaction of HetCl using in both cases i-PrMgCl.LiCl reagent as described by Steib, Andreas K. et al, Angew. Chem., Inter. Ed., 50(14), 3303-3307.

Het(Br)Cl or Het-Cl compounds are commercially available, or can be prepared by halogenation reaction of the corresponding heterocyclic ring Het.

Compounds of formula (VIII) can be prepared by amidation of compounds of formula (IX) with N,O-dimethyl-hydroxylamine in the presence of a coupling agent, e.g. dicyclohexylcarbodiimide, or (2-(1H-benzotriazol-1-yl)-1,1,3,3-tetramethyluronium hexafluorophosphate.

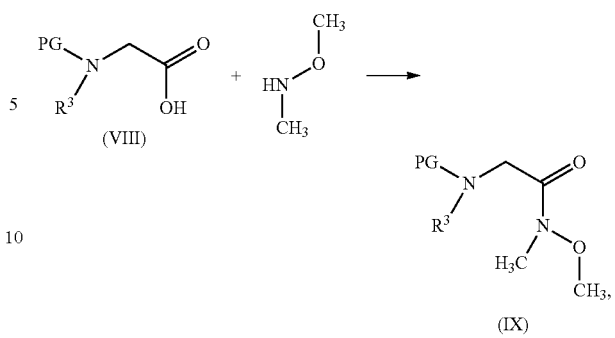

wherein PG is a protective group, and all other variables have a meaning as defined for compounds of formula (I). Compounds of formula (X) are commercially available. They can also be prepared by derivatization of glycine; or by reaction of commercially available glycine derivatives with a group $R^3$ bound to the alpha-amine moiety (e.g. N-alkyl glycine, or N-phenyl glycine) with PG-Cl, e.g. BOC-Cl, or Fmoc-Cl in the presence of a suitable base.

Compounds of formula (I) occur as the two different stereoisomers (I-S) and (I-R). These compounds can be prepared by reacting commercially available enantiopure Ellmann's sulfinamide (tert-butanesulfinamide) with compounds of formula (VII) to generate compounds of formula (VI). Hydrogenation or reduction of compounds of formula (VI) results in a mixture of diastereomers of compounds of formula (Va)

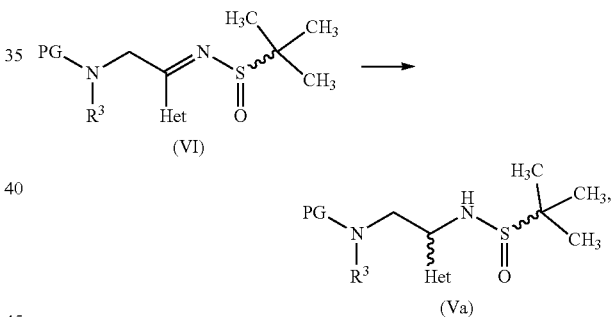

wherein PG is a protective group and all other variable have a meaning as defined for compounds of formula (I). Diastereomeric compounds of formula (Va) can be separated from another by standard chromatographical techniques, e.g. reversed phase HPLC. These pure diastereomers can then be deprotected to prepare the stereoisomerically pure compounds of formula (V), which can be used in the above reaction sequence to selectively prepare compounds of formula (I-S) or (I-R).

Alternatively, compounds of formula (I-S) and (I-R) can be purified from a isomer mixture of compounds of formula (I) via methods customary for this purpose, such as crystallization or chromatography, also on optically active adsorbate, to give the pure isomers.

If individual compounds cannot be prepared via the above described routes, they can be prepared by derivatization of other compounds of formula (I) or by customary modifications of the synthesis routes described. For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or silica gel.

Embodiments and preferred compounds of the present invention for use in pesticidal methods and for insecticidal application purposes are outlined in the following paragraphs. The remarks made below concerning preferred embodiments of the variables of compounds of formula (I) are valid both on their own in combination with each other. In a particular embodiment, the variables of the compounds of formula (I) have the following meanings, these meanings, both on their own and in combination with one another, being particular embodiments of the compounds of the formula (I):

In an embodiment of the compounds of formula (I), Z is a direct bond or $C(R^aR^{aa})O$. In a further embodiment of the compounds of formula (I), Z is a direct bond. In an embodiment of the compounds of formula (I), Z is O, $S(O)_m$, $NR^b$, $C(=X^1)$, $C(=X^1)Y^1$, or $Y^1C(=X^1)$. In a further embodiment, Z is O, $S(O)_m$, or $NR^b$. In another embodiment, Z is $C(=X^1)$, $C(=X^1)Y^1$, or $Y^1C(=X^1)$.

In one embodiment of the compounds of formula (I), $X^1$ is O. In another embodiment of the compounds of formula (I), $X^1$ is S. In an embodiment of the compounds of formula (I), $X^1$ is $NR^b$. In an embodiment of the compounds of formula (I), $Y^1$ is O. In an embodiment of the compounds of formula (I), $Y^1$ is S. In an embodiment of the compounds of formula (I), $Y^1$ is $NR^c$.

In an embodiment, $R^1$ is H, $C_1$-$C_8$-alkyl, $C_2$-$C_8$-alkenyl, $C_2$-$C_8$-alkynyl, $C_1$-$C_6$-alkoxy, $C_3$-$C_6$-cycloalkyl, $C_4$-$C_{10}$-cycloalkenyl or $C_5$-$C_{11}$-cycloalkylcycloalkyl, wherein the C-atoms of the aforementioned groups are unsubstituted, partially or fully substituted with $R^a$. In another embodiment, $R^1$ is a three- to ten-membered saturated, or partially saturated or heterocyclic ring system, which contains 1 to 3 ring members independently selected from $N(R^c)_p$, O, and S, wherein S is non-oxidized or oxidized and which heterocyclic ring is unsubstituted or substituted with $R^a$, and wherein the heterocyclic ring or ring system contains 1 to 4 ring members independently selected from $N(R^c)_p$, O, and S, wherein S is non-oxidized or oxidized In another embodiment, $R^1$ is H, $C_1$-$C_4$-alkyl, $C_2$-$C_8$-alkenyl, $C_1$-$C_6$-alkoxy, $C_3$-$C_6$-cycloalkyl or $C_5$-$C_{11}$-cycloalkylcycloalkyl, wherein the C-atoms of the aforementioned groups are unsubstituted, partially or fully substituted with halogen.

In another embodiment $R^1$ is $C_1$-$C_4$-alkyl, $C_2$-$C_8$-alkenyl, $C_3$-$C_6$-cycloalkyl, phenyl or benzyl, wherein the C-atoms of the aforementioned groups are unsubstituted, partially or fully substituted with $R^a$. In another embodiment, $R^1$ is $C_1$-$C_4$-alkyl, $C_1$-$C_4$-haloalkyl, $C_3$-$C_6$-cycloalkyl, $C_2$-$C_4$-alkenyl, phenyl, or benzyl. In another embodiment, $R^1$ is $C_1$-$C_4$-alkyl, $C_1$-$C_4$-haloalkyl, $C_3$-$C_6$-cycloalkyl, $C_2$-$C_4$-alkenyl. In another embodiment, $R^1$ is $CH_3$ or $CH_2CH_3$.

In a further embodiment $R^1$ is $C_1$-$C_4$-alkyl, $C_3$-$C_6$-cycloalkyl or phenyl, wherein the C-atoms of the aforementioned groups are unsubstituted, partially or fully substituted with halogen or $C_1$-$C_4$-alkyl. In a further embodiment $R^1$ is $C_1$-$C_4$-alkyl, $C_2$-$C_4$-alkenyl, phenyl or benzyl, wherein the C-atoms of the aforementioned groups are unsubstituted, partially, or fully substituted with halogen, preferably Cl or F.

In a further embodiment $R^1$ is $C_1$-$C_4$-alkyl, $C_3$-$C_6$-cycloalkyl or phenyl, preferably $CH_3$, $CH_2CH_3$, $CH(CH_3)_2$, cyclopropyl or phenyl. In another embodiment $R^1$ is $C_1$-$C_3$-alkyl, preferably $CH_3$, $CH_2CH_3$ or $CH(CH_3)_2$.

In one embodiment, $R^2$ is H, halogen, CN, $C_1$-$C_6$-alkyl, $C_1$-$C_6$-haloalkyl, $C_1$-$C_6$-haloalkoxy, $C_1$-$C_6$-alkoxy, $C_2$-$C_6$-alkenyl, $C_2$-$C_6$-alkynyl, $C_3$-$C_6$-cycloalkyl, $C_5$-$C_6$-cycloalkenyl, $C_5$-$C_{14}$-cycloalkylcycloalkyl or $S(O)_mR^b$, wherein the C-atoms of the aforementioned groups are unsubstituted, partially or fully substituted with $R^{2a}$.

In another embodiment, $R^2$ is H, halogen, CN, $C_1$-$C_6$-alkyl, $C_1$-$C_2$-alkoxy-$C_1$-$C_2$-alkyl or $C_3$-$C_6$-cycloalkyl, wherein the C-atoms of the aforementioned groups are unsubstituted or substituted with halogen or CN. In another embodiment, $R^2$ is H, halogen, CN or $C_1$-$C_4$-alkyl, wherein the C-atoms of the aforementioned groups are unsubstituted or substituted with halogen. In a further embodiment $R^2$ is CN. In a further embodiment, $R^2$ is H or $C_1$-$C_2$-alkyl, particularly $CH_3$.

In a further embodiment, $R^2$ is $C_1$-$C_6$-haloalkyl, preferably $C_1$-$C_2$-haloalkyl, particularly halomethyl, such as $CF_3$ or $CHF_2$. In another embodiment, $R^2$ is $C_1$-$C_2$-alkoxy-$C_1$-$C_2$-alkyl, preferably $C_1$-$C_2$-alkoxy-methyl, particularly $CH_2OCH_3$.

In another embodiment, $R^2$ is $C_3$-$C_6$-cycloalkyl, preferably cyclopropyl which is unsubstituted or substituted with halogen or cyano. In another embodiment, $R^2$ is $C_2$-$C_6$-alkyl, preferably $C_2$-$C_4$-alkyl, particularly $CH_2CH_3$ or $C(CH_3)_3$. In another embodiment, $R^2$ is $C_1$-$C_6$-alkyl, preferably $C_1$-$C_2$-alkyl, particularly $CH_3$. In another embodiment, $R^2$ is halogen, preferably Cl or F, particularly F.

In one embodiment, $R^2$ is a five- or six-membered carbo- or heterocyclic ring, which ring is unsubstituted, partially, or fully substituted with $R^{2a}$, and wherein preferably $R^{2a}$ is each independently halogen, $C_1$-$C_6$-alkyl, $C_1$-$C_6$-haloalkyl, $OR^c$, $C(=O)OR^c$, $C(=O)NR^bR^c$;
phenyl, or pyridyl which groups are unsubstituted or substituted with halogen, $C_1$-$C_6$-haloalkyl or $C_1$-$C_6$-haloalkoxy;
more preferably wherein
$R^{2a}$ is each independently halogen, $C_1$-$C_6$-alkyl, $C_1$-$C_6$-haloalkyl, $C_1$-$C_6$-alkoxy, $C_1$-$C_6$-haloalkoxy;
most preferably wherein
$R^{2a}$ is each independently halogen, $C_1$-$C_4$-alkyl, $C_1$-$C_4$-haloalkyl, $C_1$-$C_4$-alkoxy, $C_1$-$C_4$-haloalkoxy.

In another embodiment, $R^2$ is a five- or six-membered carbo- or heterocyclic ring, which ring is unsubstituted, partially, or fully substituted with $R^{2a}$, and wherein preferably $R^{2a}$ is each independently halogen, $C_1$-$C_6$-haloalkyl, $OR^c$, $C(=O)OR^c$, $C(=O)NR^bR^c$; phenyl, or pyridyl which groups are unsubstituted or substituted with halogen, $C_1$-$C_6$-haloalkyl or $C_1$-$C_6$-haloalkoxy;
more preferably wherein
$R^b$ is each independently H, $C_1$-$C_4$-alkyl, $C_1$-$C_4$-haloalkyl, or $C_1$-$C_6$ cycloalkyl; and
$R^c$ is each independently H, $C_1$-$C_6$-alkyl, $C_1$-$C_6$-haloalkyl, $C_1$-$C_6$-alkoxy, or $C_1$-$C_6$-haloalkoxy; or
two geminally bound groups $R^bR^c$ together with the atom to which they are bound, form a 3-, 4-, 5-, 6- or 7-membered saturated, partially unsaturated, or aromatic carbo- or heterocyclic ring.

In another further embodiment, $R^2$ is a six-membered carbo- or heterocyclic ring, which ring is unsubstituted, partially, or fully substituted with $R^{2a}$, and wherein $R^{2a}$ is each independently halogen, $C_1$-$C_6$-haloalkyl, $OR^c$, $C(=O)OR^c$, $C(=O)NR^bR^c$; phenyl, or pyridyl, which groups are unsubstituted or substituted with $R^{2aa}$.

In a further embodiment, $R^2$ is a six-membered aromatic carbocyclic ring, which ring is unsubstituted, partially, or fully substituted with $R^{2a}$, and wherein $R^{2a}$ is each independently halogen, $C_1$-$C_6$-haloalkyl, $OR^c$, $C(=O)OR^c$, $C(=O)NR^bR^c$; phenyl, or pyridyl, which groups are unsubstituted or substituted with halogen, $C_1$-$C_6$-haloalkyl or $C_1$-$C_6$-haloalkoxy.

In another embodiment, $R^2$ is phenyl, which is unsubstituted, partially, or fully substituted with $R^{2a}$.

In another embodiment, $R^2$ is phenyl which is unsubstituted, partially or fully substituted with halogen, $C_1$-$C_4$-alkyl, $C_1$-$C_4$-haloalkyl, $C_1$-$C_4$-alkoxy, or $C_1$-$C_4$-haloalkoxy. In another embodiment, $R^2$ is phenyl, which is unsubstituted, partially, or fully substituted with halogen, $C_1$-$C_3$-alkyl, $C_1$-$C_3$-haloalkyl, $C_1$-$C_3$-alkoxy, or $C_1$-$C_3$-haloalkoxy. In another embodiment, $R^2$ is phenyl, which is unsubstituted, partially, or fully substituted with halogen, $C_1$-$C_3$-haloalkyl, or $C_1$-$C_3$-alkoxy. In another embodiment, $R^2$ is phenyl, 3,5-dichlorophenyl, 3-trifluoromethylphenyl, 3-difluoromethylphenyl, or 4-methoxyphenyl.

In another embodiment, $R^2$ is phenyl. In another embodiment, $R^2$ is phenyl, which is partially substituted with halogen, preferably Cl. In another embodiment, $R^2$ is phenyl, which is fully substituted with halogen, preferably Cl. In another embodiment, $R^2$ is phenyl, which is partially substituted with $C_1$-$C_6$-alkoxy. In another embodiment, $R^2$ is phenyl, which is partially substituted with $C_1$-$C_6$-haloalkoxy.

In another embodiment, $R^2$ is phenyl which is unsubstituted, or substituted with phenyl. In another embodiment, $R^2$ is a six-membered heterocyclic ring, which contains 1 or 2, preferably 1, ring member(s) independently selected from $NR^c$, O, and S, wherein S is non-oxidized or oxidized, and wherein the heterocyclic ring is unsubstituted or substituted with one or more groups $R^{2a}$.

In one embodiment, $R^3$ is H. In another embodiment, $R^3$ is $C_1$-$C_8$-alkyl, $C_2$-$C_8$-alkenyl, $C_2$-$C_8$-alkynyl, $C_3$-$C_{10}$-cycloalkyl, $C_4$-$C_{10}$-cycloalkenyl, $C_5$-$C_{14}$-cycloalkylcycloalkyl, which groups are unsubstituted, or partially, or fully substituted with $R^a$.

In another embodiment, $R^3$ is
$C_1$-$C_6$-alkyl, $C_1$-$C_6$-haloalkyl;
$C_3$-$C_6$-cycloalkyl, $C_2$-$C_4$-alkenyl, phenyl, or benzyl, which groups are unsubstituted, partially, or fully substituted with halogen or $C_1$-$C_4$-alkyl; or
$C(=O)R^b$, $C(=O)OR^e$, $C(=O)NR^bR^c$, $C(=S)NR^bR^c$, $SO_2NR^bR^c$, $C(=NR^c)R^c$, $C(=NOR^c)R^c$; or $C(=NNR^bR^c)R^c$.

preferably wherein $R^3$ is
$C_1$-$C_4$-alkyl, $C_1$-$C_4$-haloalkyl, $C_2$-$C_4$-alkenyl, $C_2$-$C_4$-haloalkenyl, $C(=O)NR^bR^c$, or $C(=O)OR^e$, more preferably $C_1$-$C_4$-alkyl, $C_1$-$C_4$-haloalkyl, $C_2$-$C_4$-alkenyl, $C_2$-$C_4$-haloalkenyl, $C(=O)NH-C_1$-$C_6$-alkyl, or $C(=O)O-C_1$-$C_6$-alkyl, most preferably $C_1$-$C_3$-alkyl or $C(=O)O-C_1$-$C_4$-alkyl.

In another embodiment, $R^3$ is $C_1$-$C_4$-alkyl, $C_1$-$C_4$-haloalkyl; $C_3$-$C_6$-cycloalkyl, $C_2$-$C_4$-alkenyl, phenyl, or benzyl, which groups are unsubstituted, partially, or fully substituted with halogen or $C_1$-$C_4$-alkyl. In another embodiment, $R^3$ is $C_1$-$C_4$-alkyl, $C_1$-$C_4$-haloalkyl, $C_2$-$C_4$-alkenyl, or $C_2$-$C_4$-haloalkenyl, more preferably $C_1$-$C_4$-alkyl, most preferably $CH_3$ or $CH_2CH_3$.

In another embodiment, $R^3$ is a three- to eleven-membered saturated, partially unsaturated, or aromatic carbo-, or heterocyclic ring or ring system, which ring or ring system is unsubstituted, partially, or fully substituted with $R^a$, and wherein the heterocyclic ring or ring system contains 1 to 4 ring members independently selected from $N(R^c)_p$, O, and S, wherein S is non-oxidized or oxidized.

In another embodiment, $R^3$ is 2-pyridyl, 3-pyridyl, or 3,4-pyrimidyl, which groups are unsubstituted, partially, or fully substituted with $R^a$. In another embodiment, $R^3$ is 2-pyridyl, 3-pyridyl, or 3,4-pyrimidyl, which groups are unsubstituted, partially, or fully substituted with halogen, $C_1$-$C_3$-alkyl, $C_1$-$C_3$-haloalkyl, $C_1$-$C_3$-alkoxy, or $C_1$-$C_3$-haloalkoxy.

In another embodiment, $R^3$ is phenyl, which is unsubstituted, partially, or fully substituted with $R^a$. In another embodiment, $R^3$ is phenyl. In another embodiment, $R^3$ is phenyl, which is partially, or fully substituted with halogen, $C_1$-$C_6$-alkyl, $C_1$-$C_6$-haloalkyl, $C_1$-$C_6$-alkoxy, or $C_1$-$C_6$-haloalkoxy. In another embodiment, $R^3$ is phenyl, which is partially, or fully substituted with halogen, $C_1$-$C_3$-alkyl, $C_1$-$C_3$-haloalkyl, $C_1$-$C_3$-alkoxy, or $C_1$-$C_3$-haloalkoxy.

In another embodiment, $R^3$ is $C(=O)R^b$, $C(=O)OR^e$, $NR^bR^c$, $C(=O)NR^bR^c$, $C(=S)NR^bR^c$, $SO_2NR^bR^c$, $OC(=O)R^c$, $OC(=O)OR^e$, $OC(=O)NR^bR^e$, $N(R^c)C(=O)R^c$, $N(R^c)C(=O)OR^e$, $N(R^c)C(=O)NR^bR^c$, $NR^cSO_2R^b$, $NR^cSO_2NR^bR^c$, $Si(R^d)_3$, $C(=NR^c)R^c$, $C(=NOR^c)R^c$, $C(=NNR^bR^c)R^c$, $C(=NN(C(=O)R^b)R^c)R^c$, $C(=NN(C=O)OR^c)(R^c)_2$, $S(=O)_o(=NR^b)_qR^c$ or $N=CR^bR^c$.

In another embodiment, $R^3$ is $C(=O)R^b$, $C(=O)OR^e$, $NR^bR^c$, $C(=O)NR^bR^c$, $C(=S)NR^bR^c$, $SO_2NR^bR^c$, $OC(=O)R^c$, $OC(=O)OR^e$, $OC(=O)NR^bR^e$, $N(R^c)C(=O)R^c$, $N(R^c)C(=O)OR^e$, $N(R^c)C(=O)NR^bR^c$, $NR^cSO_2R^b$, $NR^cSO_2NR^bR^c$, $Si(R^d)_3$, $C(=NR^c)R^c$, $C(=NOR^c)R^c$, $C(=NNR^bR^c)R^c$, $C(=NN(C(=O)R^b)R^c)R^c$, $C(=NN(C=O)OR^c)(R^c)_2$, $S(=O)_o(=NR^b)_qR^c$ or $N=CR^bR^c$.

In another embodiment, $R^3$ is $C(=O)R^b$, $C(=O)OR^e$, $C(=O)NR^bR^c$, $SO_2NR^bR^c$, $OC(=O)R^c$, $OC(=O)OR^e$, $OC(=O)NR^bR^e$, $N(R^c)C(=O)R^c$, $N(R^c)C(=O)OR^e$, $N(R^c)C(=O)NR^bR^c$, $NR^cSO_2NR^bR^c$, $C(=NR^c)R^c$, $C(=NOR^c)R^c$, $C(=NNR^bR^c)R^c$, $C(=NN(C(=O)R^b)R^c)R^c$, $C(=NN(C=O)OR^c)(R^c)_2$, or $N=CR^bR^c$.

In another embodiment, $R^3$ is $C(=O)R^b$, $C(=O)OR^e$, $C(=O)NR^bR^c$, $N(R^c)C(=O)R^c$, $N(R^c)C(=O)OR^e$, $N(R^c)C(=O)NR^bR^c$, or $NR^cSO_2NR^bR^c$.

In another embodiment, $R^3$ is $C(=O)R^b$, $C(=O)OR^e$, or $C(=O)NR^bR^c$. In another embodiment, $R^3$ is $C(=O)OR^e$, wherein preferably $R^e$ is $C_1$-$C_6$-alkyl.

In one embodiment, each $R^a$ is independently selected from
halogen, CN, OH, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $N=S(=O)_pR^cR^c$, $S(=O)_o(=NR^b)_qR^c$, $SF_5$, OCN, SCN, $Si(R^d)_3$; or $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, which groups are unsubstituted, partially or fully substituted with $R^{aa}$.

In another embodiment, each $R^a$ is independently selected from
halogen, OH, CN, $NO_2$, $OR^c$, or
$C_1$-$C_6$-alkyl, $C_2$-$C_4$-alkenyl, $C_2$-$C_4$-alkynyl, $C_3$-$C_6$-cycloalkyl, which groups are unsubstituted, partially, or fully substituted with $R^{aa}$.

In another embodiment, each $R^a$ is independently selected from halogen, OH, $C_1$-$C_4$-alkyl, $C_1$-$C_4$-haloalkyl, $C_1$-$C_4$- alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalky, or $C_3$-$C_6$-halocycloalkyl.

In another embodiment, each $R^a$ is independently selected from halogen, OH, $C_1$-$C_4$-alkyl, $C_1$-$C_4$-haloalkyl, $C_1$-$C_4$-alkoxy, or $C_1$-$C_4$-haloalkoxy.

In one embodiment, each $R^a$ is independently selected from halogen, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, OH, CN, $OR^c$, $NR^bR^c$, $NO_2$, phenyl, pyridyl, thiazyl, furanyl, pyrimidinyl or thienyl, wherein the C-atoms of the aforementioned groups are unsubstituted or substituted with one or more $R^{aa}$.

In another embodiment, each $R^a$ is independently selected from halogen, OH, $C_1$-$C_4$-alkyl, $C_1$-$C_4$-haloalkyl, $C_1$-$C_4$-alkoxy, $C_1$-$C_4$-haloalkoxy, or $C_3$-$C_6$-cycloalkyl. In another embodiment, $R^a$ is halogen, OH, $C_1$-$C_3$-alkyl, $C_1$-$C_3$-haloalkyl, $C_1$-$C_3$-alkoxy, $C_1$-$C_3$-haloalkoxy. In one embodiment, $R^a$ is halogen, preferably Cl. In another embodiment, each $R^a$ is independently selected from $C_1$-$C_3$-haloalkyl. In another embodiment, each $R^a$ is independently selected from $C_1$-$C_3$-alkoxy. In another embodiment, $R^a$ is OH.

In an embodiment, each $R^b$ is independently H, $C_1$-$C_6$-alkyl, $C_1$-$C_6$-haloalkyl, $C_1$-$C_6$-alkoxy, $C_1$-$C_6$-haloalkoxy, phenyl, pyridyl, thiazyl or thienyl, wherein the C-atoms of the aforementioned groups are unsubstituted or substituted with $R^{aa}$. In a further embodiment, each $R^b$ is independently H, $C_1$-$C_6$-alkyl, $C_1$-$C_6$-haloalkyl, $C_1$-$C_6$-alkoxy or $C_1$-$C_6$-haloalkoxy. In a further embodiment, each $R^b$ is independently H, $C_1$-$C_6$-alkyl or $C_1$-$C_6$-haloalkyl. In an embodiment, each $R^b$ is independently $C_1$-$C_6$-alkyl or $C_1$-$C_6$-haloalkyl. In another embodiment, $R^b$ is H.

In one embodiment, each $R^c$ is independently hydrogen, $C_1$-$C_4$-alkyl, $C_1$-$C_4$-haloalkyl, $C_1$-$C_4$-alkylcarbonyl, $C_1$-$C_6$ cycloalkyl, phenyl, pyridyl, thiazyl or thienyl, wherein the C-atoms of the aforementioned groups may be substituted with $R^{aa}$. In a further embodiment, each $R^c$ is independently hydrogen, $C_1$-$C_4$-alkyl, $C_1$-$C_4$-haloalkyl, $C_1$-$C_4$-alkylcarbonyl, or $C_1$-$C_6$-cycloalkyl. In another embodiment, each $R^c$ is independently hydrogen, $C_1$-$C_6$-alkyl or $C_1$-$C_6$-haloalkyl. In another embodiment, each $R^c$ is independently $C_1$-$C_6$-alkyl or $C_1$-$C_6$-haloalkyl. In another embodiment, $R^c$ is H.

In one embodiment, two geminally bound groups $R^bR^b$, $R^cR^b$ or $R^cR^c$ together with the atom to which they are bound, form a 3-, 4-, 5-, 6- or 7-membered saturated, partially unsaturated or aromatic carbo- or heterocyclic ring, which heterocyclic ring contains 1 to 2 ring members independently selected from N, O, S, NO, SO and $SO_2$ and wherein the carbo- or heterocyclic ring is unsubstituted, partially or fully substituted with $R^{bb}$.

In another embodiment, two geminally bound groups $R^bR^b$, $R^cR^b$ or $R^cR^c$ together with the atom to which they are bound, form a 5- or 6-membered saturated, partially unsaturated or aromatic carbocyclic ring, which ring is unsubstituted, partially or fully substituted with $R^{bb}$.

In another embodiment, two geminally bound groups $R^bR^b$, $R^cR^b$ or $R^cR^c$ together with the atom to which they are bound, form a 5- or 6-membered saturated, partially unsaturated or aromatic heterocyclic ring, which ring contains 1 to 2 ring members independently selected from N, O, S, NO, SO and $SO_2$, wherein the heterocyclic ring is unsubstituted, partially or fully substituted with $R^{bb}$.

In one embodiment, each $R^d$ is independently H, phenyl, $C_1$-$C_4$-alkyl or $C_2$-$C_6$-alkenyl, wherein the C-atoms of the aforementioned groups are unsubstituted or substituted with one or more halogen atoms. In another embodiment, each $R^d$ is independently $C_1$-$C_4$-alkyl or phenyl, which is unsubstituted or substituted with halogen. In another embodiment, each $R^c$ is independently $C_1$-$C_4$-alkyl, preferably $CH_3$.

In one embodiment, each $R^e$ is independently $C_1$-$C_4$-alkyl, $C_1$-$C_4$-haloalkyl, $C_1$-$C_4$-alkylcarbonyl, $C_1$-$C_6$ cycloalkyl, phenyl, pyridyl, thiazyl or thienyl wherein the aforementioned groups are unsubstituted, partially, or fully substituted with $R^{aa}$. In a further embodiment, each $R^e$ is independently $C_1$-$C_4$-alkyl, $C_1$-$C_4$-haloalkyl, $C_1$-$C_4$-alkylcarbonyl, or $C_1$-$C_6$-cycloalkyl. In another embodiment, each $R^e$ is independently $C_1$-$C_4$-alkyl. In another embodiment, each $R^e$ is independently $C_1$-$C_6$-alkyl or $C_1$-$C_6$-haloalkyl. In another embodiment, each $R^e$ is independently $C_1$-$C_4$-alkyl or $C_1$-$C_4$-haloalkyl.

In an embodiment, each $R^{aa}$ is independently halogen, $C_1$-$C_6$-alkyl or $C_1$-$C_6$-haloalkyl. In another embodiment, each $R^{aa}$ is independently $C_1$-$C_6$-alkoxy or $C_1$-$C_6$-haloalkoxy. In an embodiment, each $R^{aa}$ is independently halogen.

In an embodiment, $R^{2a}$ is halogen, $C_1$-$C_6$-haloalkyl, $OR^c$, $C(=O)OR^c$, $C(=O)NR^bR^c$; or phenyl, which is unsubstituted, or substituted with one or more $R^{2aa}$. In another embodiment, $R^{2a}$ is halogen, $C_1$-$C_6$-haloalkyl, or $C_1$-$C_6$-alkoxy, or $C_1$-$C_6$-haloalkoxy. In another embodiment, $R^{2a}$ is halogen, $C_1$-$C_3$-haloalkyl, $C_1$-$C_3$-alkoxy, or $C_1$-$C_3$-haloalkoxy. In another embodiment, $R^{2a}$ is halogen, $C_1$-$C_6$-haloalkyl, or $C_1$-$C_6$-alkoxy. In another embodiment, $R^{2a}$ is halogen, $C_1$-$C_3$-haloalkyl, or $C_1$-$C_3$-alkoxy.

In another embodiment, two geminally bound groups $R^{2a}$ together may form a group selected from =O, =S and $=N(C_1$-$C_6$-alkyl).

In another embodiment, each $R^{2a}$ is independently halogen, CN, $OR^c$, $NR^bR^c$, $NO_2$; or $C_1$-$C_6$-alkyl, $C_1$-$C_6$-haloalkyl, $C_3$-$C_6$-cycloalkyl, phenyl, pyridyl, thiazyl, furanyl, pyrimidinyl or thienyl, which groups are unsubstituted, or substituted with one or more $R^{2aa}$. In another embodiment, each $R^{2aa}$ is independently $C_3$-$C_6$-cycloalkyl, phenyl, pyridyl, thiazyl, furanyl, pyrimidinyl or thienyl, which groups are unsubstituted, or substituted with one or more $R^{2aa}$.

In a another embodiment, each $R^{2a}$ is independently phenyl which is unsubstituted or substituted with one or more $R^{2aa}$. In a another embodiment, each $R^{2a}$ is independently halogen. In another embodiment, each $R^{2a}$ is independently $C_1$-$C_6$-haloalkyl. In another embodiment, each $R^{2a}$ is independently $C_1$-$C_6$-haloalkoxy. In another embodiment, each $R^{2a}$ is independently $C_1$-$C_6$-alkoxy.

In another embodiment, each $R^{2a}$ is independently halogen, CN, $NO_2$, $S(O)_mR^b$, $C(=O)R^c$, $C(=O)OR^c$, $C(O)NR^bR^c$, $C(=S)NR^bR^c$; or $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, which groups are unsubstituted, partially or fully substituted with $R^{aa}$.

In further embodiment, each $R^{2a}$ is independently $C(=O)OR^c$ or $C(=O)NR^bR^c$. In another embodiment, each $R^{2a}$ is independently halogen, CN; or $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, which groups are unsubstituted, partially or fully substituted with $R^{2aa}$. In an embodiment, each $R^{2a}$ is independently Br, Cl or F, particularly Cl. In another embodiment, each $R^{2a}$ is independently $C_1$-$C_2$-haloalkyl or $C_1$-$C_2$-alkoxy, preferably halomethyl or methoxy, such as $CHF_2$, $CF_3$, or $OCH_3$.

In an embodiment, each $R^{2aa}$ is independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $N(C_1$-$C_6$-alkyl)($C_1$-$C_6$-alkyl), $C(=O)(O)_p(C_1$-$C_6$-alkyl), $C(=O)N(C_1$-$C_6$-alkyl)($C_1$-$C_6$-alkyl), $S(O)_m(C_1$-$C_6$-alkyl), SO$_2$N(C$_1$-C$_6$-alkyl)(C$_1$-C$_6$-alkyl), OSO$_2$(C$_1$-C$_6$-alkyl), N(C$_1$-C$_6$-alkyl)SO$_2$(C$_1$-C$_6$-alkyl), or S(=O)$_p$(=N(C$_1$-C$_6$-alkyl))(C$_1$-C$_6$-alkyl) or two geminally bound groups R$^{2aa}$ together may form a group selected from =O, =S and =N(C$_1$-C$_6$-alkyl).

In an embodiment, each R$^{2aa}$ is independently halogen, C$_1$-C$_6$-alkyl, C$_1$-C$_6$-haloalkyl, C$_1$-C$_6$-alkoxy, C$_1$-C$_6$-haloalkoxy, C$_2$-C$_4$-alkenyl, C$_2$-C$_4$-alkynyl, C$_3$-C$_6$-cycloalkyl, CN, N(C$_1$-C$_6$-alkyl)(C$_1$-C$_6$-alkyl), C(=O)(O)$_p$(C$_1$-C$_6$-alkyl), C(=O)N(C$_1$-C$_6$-alkyl)(C$_1$-C$_6$-alkyl), S(O)$_m$(C$_1$-C$_6$-alkyl), SO$_2$N(C$_1$-C$_6$-alkyl)(C$_1$-C$_6$-alkyl), OSO$_2$(C$_1$-C$_6$-alkyl), N(C$_1$-C$_6$-alkyl)SO$_2$(C$_1$-C$_6$-alkyl), or S(=O)$_p$(=N(C$_1$-C$_6$-alkyl))(C$_1$-C$_6$-alkyl). In another embodiment, two geminally bound groups R$^{2aa}$ together form a group selected from =O, =S and =N(C$_1$-C$_6$-alkyl).

In an embodiment, each R$^{bb}$ is independently halogen, C$_1$-C$_6$-alkyl, C$_1$-C$_6$-haloalkyl, C$_1$-C$_6$-alkoxy, C$_1$-C$_6$-haloalkoxy, C$_2$-C$_4$-alkenyl, C$_2$-C$_4$-alkynyl, C$_3$-C$_6$-cycloalkyl, CN, N(C$_1$-C$_6$-alkyl)(C$_1$-C$_6$-alkyl), C(=O)(O)$_p$(C$_1$-C$_6$-alkyl), C(=O)N(C$_1$-C$_6$-alkyl)(C$_1$-C$_6$-alkyl), S(O)$_m$(C$_1$-C$_6$-alkyl), SO$_2$N(C$_1$-C$_6$-alkyl)(C$_1$-C$_6$-alkyl), OSO$_2$(C$_1$-C$_6$-alkyl), N(C$_1$-C$_6$-alkyl)SO$_2$(C$_1$-C$_6$-alkyl), S(=O)$_p$(=N(C$_1$-C$_6$-alkyl))(C$_1$-C$_6$-alkyl); or two geminally bound groups R$^3$ together form a group selected from =O, =S and =N(C$_1$-C$_6$-alkyl).

In an embodiment, each R$^{bb}$ is independently halogen, C$_1$-C$_6$-alkyl, C$_1$-C$_6$-haloalkyl, C$_1$-C$_6$-alkoxy, C$_1$-C$_6$-haloalkoxy, C$_2$-C$_4$-alkenyl, C$_2$-C$_4$-alkynyl, C$_3$-C$_6$-cycloalkyl, CN, N(C$_1$-C$_6$-alkyl)(C$_1$-C$_6$-alkyl), C(=O)(O)$_p$(C$_1$-C$_6$-alkyl), C(=O)N(C$_1$-C$_6$-alkyl)(C$_1$-C$_6$-alkyl), S(O)$_m$(C$_1$-C$_6$-alkyl), SO$_2$N(C$_1$-C$_6$-alkyl)(C$_1$-C$_6$-alkyl), OSO$_2$(C$_1$-C$_6$-alkyl), N(C$_1$-C$_6$-alkyl)SO$_2$(C$_1$-C$_6$-alkyl), or S(=O)$_p$(=N(C$_1$-C$_6$-alkyl))(C$_1$-C$_6$-alkyl). In another embodiment, two geminally bound groups R$^{3a}$ together form a group selected from =O, =S and =N(C$_1$-C$_6$-alkyl).

In an embodiment, m is 0. In another embodiment, m is 1. In another embodiment, m is 2. In an embodiment, p is 0. In another embodiment, p is 1.

In an embodiment Het is a five- or six-membered saturated, partially unsaturated or aromatic heterocyclic ring, which contains 1 to 4 ring members independently selected from N(R$^c$)$_p$, O and S, wherein the heterocyclic ring is substituted with one or more, same or different substituents R$^a$.

In an embodiment Het is a five- or six-membered saturated, partially unsaturated or aromatic heterocyclic ring, which contains 1 to 2 ring member independently selected from N(R$^c$)$_p$, O and S, wherein the heterocyclic ring is substituted with one or more, same or different substituents R$^a$.

In an embodiment Het is a five-membered aromatic heterocyclic ring, which contains 2 ring members independently selected from N(R$^c$)$_p$, O and S, wherein the heterocyclic ring is substituted with one or more, same or different substituents R$^a$.

In an embodiment Het is a six-membered aromatic heterocyclic ring, which contains 2 heteroatoms independently selected from N(R$^c$)$_p$, O and S, preferably independently selected from S and N(R$^c$)$_p$, wherein the heterocyclic ring is substituted with one or more, same or different substituents R$^a$.

In an embodiment Het is a six-membered aromatic heterocyclic ring, which contains 1 ring member selected from N(R$^c$)$_p$, O and S, preferably N(R$^c$)$_p$, wherein the heterocyclic ring is substituted with one or more, same or different substituents R$^a$.

In an embodiment Het is pyridyl, which is substituted with one or more, same or different substituents R$^a$. In another embodiment, Het is thiazole, which is substituted with one or more, same or different R$^a$. In another embodiment, Het is pyrimidine, which is substituted with one or more, same or different substituents R$^a$.

In another embodiment, Het is selected from any one of the rings D-1 to D-56:

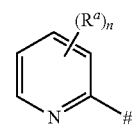
D-1

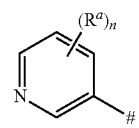
D-2

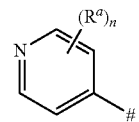
D-3

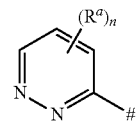
D-4

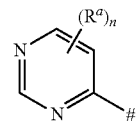
D-5

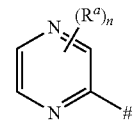
D-6

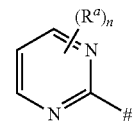
D-7

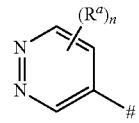
D-8

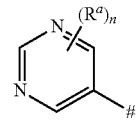
D-9

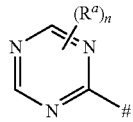
D-10

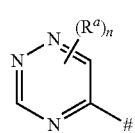 D-11
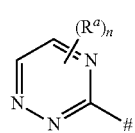 D-12
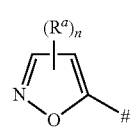 D-13
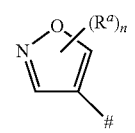 D-14
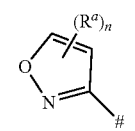 D-15
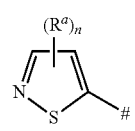 D-16
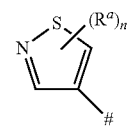 D-17
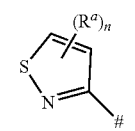 D-18
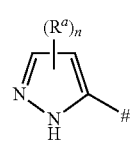 D-19
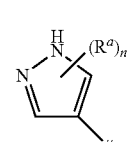 D-20
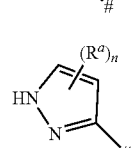 D-21
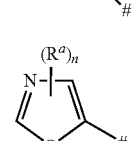 D-22
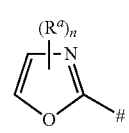 D-23
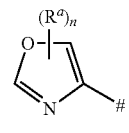 D-24
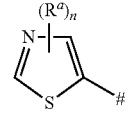 D-25
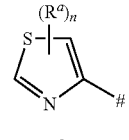 D-26
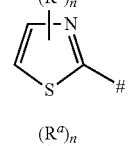 D-27
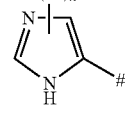 D-28
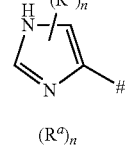 D-29
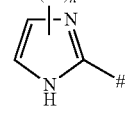 D-30
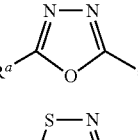 D-36
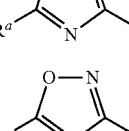 D-37
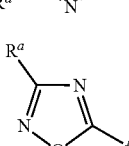 D-38
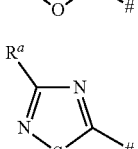 D-39
D-40

-continued

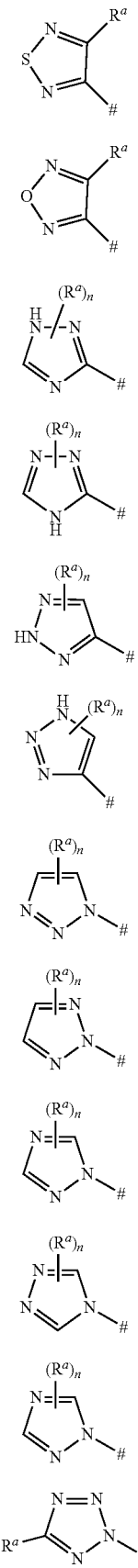

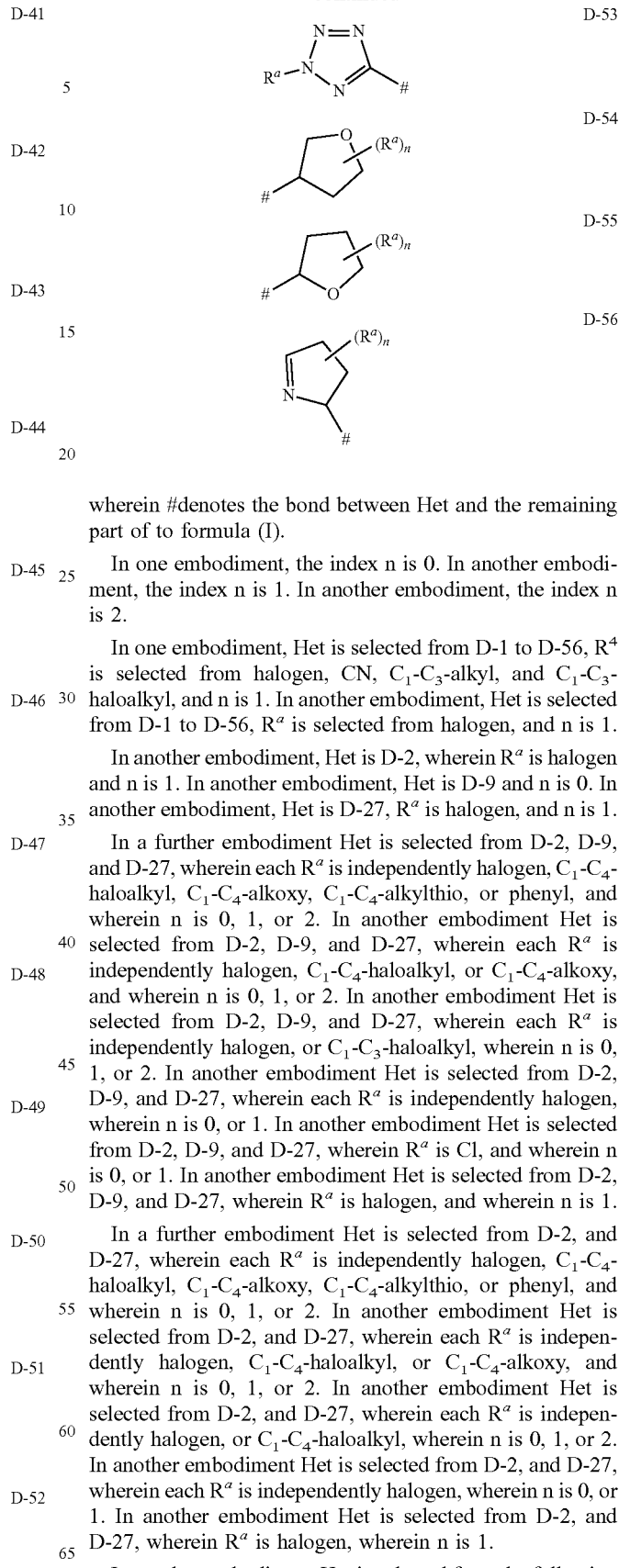

wherein #denotes the bond between Het and the remaining part of to formula (I).

In one embodiment, the index n is 0. In another embodiment, the index n is 1. In another embodiment, the index n is 2.

In one embodiment, Het is selected from D-1 to D-56, $R^a$ is selected from halogen, CN, $C_1$-$C_3$-alkyl, and $C_1$-$C_3$-haloalkyl, and n is 1. In another embodiment, Het is selected from D-1 to D-56, $R^a$ is selected from halogen, and n is 1.

In another embodiment, Het is D-2, wherein $R^a$ is halogen and n is 1. In another embodiment, Het is D-9 and n is 0. In another embodiment, Het is D-27, $R^a$ is halogen, and n is 1.

In a further embodiment Het is selected from D-2, D-9, and D-27, wherein each $R^a$ is independently halogen, $C_1$-$C_4$-haloalkyl, $C_1$-$C_4$-alkoxy, $C_1$-$C_4$-alkylthio, or phenyl, and wherein n is 0, 1, or 2. In another embodiment Het is selected from D-2, D-9, and D-27, wherein each $R^a$ is independently halogen, $C_1$-$C_4$-haloalkyl, or $C_1$-$C_4$-alkoxy, and wherein n is 0, 1, or 2. In another embodiment Het is selected from D-2, D-9, and D-27, wherein each $R^a$ is independently halogen, or $C_1$-$C_3$-haloalkyl, wherein n is 0, 1, or 2. In another embodiment Het is selected from D-2, D-9, and D-27, wherein each $R^a$ is independently halogen, wherein n is 0, or 1. In another embodiment Het is selected from D-2, D-9, and D-27, wherein $R^a$ is Cl, and wherein n is 0, or 1. In another embodiment Het is selected from D-2, D-9, and D-27, wherein $R^a$ is halogen, and wherein n is 1.

In a further embodiment Het is selected from D-2, and D-27, wherein each $R^a$ is independently halogen, $C_1$-$C_4$-haloalkyl, $C_1$-$C_4$-alkoxy, $C_1$-$C_4$-alkylthio, or phenyl, and wherein n is 0, 1, or 2. In another embodiment Het is selected from D-2, and D-27, wherein each $R^a$ is independently halogen, $C_1$-$C_4$-haloalkyl, or $C_1$-$C_4$-alkoxy, and wherein n is 0, 1, or 2. In another embodiment Het is selected from D-2, and D-27, wherein each $R^a$ is independently halogen, or $C_1$-$C_4$-haloalkyl, wherein n is 0, 1, or 2. In another embodiment Het is selected from D-2, and D-27, wherein each $R^a$ is independently halogen, wherein n is 0, or 1. In another embodiment Het is selected from D-2, and D-27, wherein $R^a$ is halogen, wherein n is 1.

In another embodiment Het is selected from the following rings D-1a, D-2a, D-9a, and D-27a.

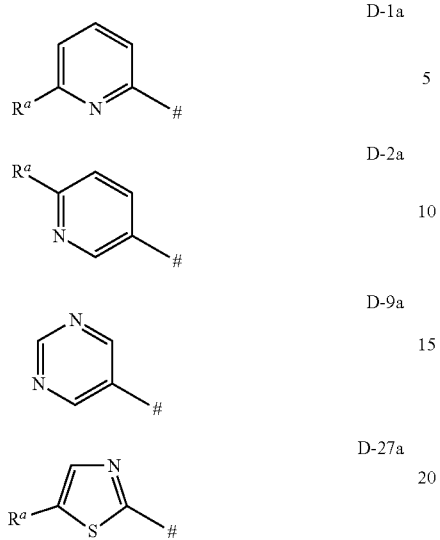

D-1a

D-2a

D-9a

D-27a

In another embodiment, Het is selected from D-1a, D-2a, and D-27a, wherein $R^a$ is halogen, preferably wherein $R^a$ is Cl.

In another embodiment, Het is selected from D-1a, wherein $R^a$ is halogen, preferably wherein $R^a$ is Cl.

In another embodiment Het is selected from the following rings D-2a, D-9a, and D-27a.

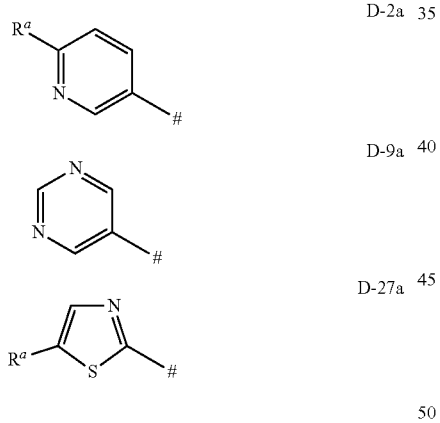

D-2a

D-9a

D-27a wherein #denotes the bond between Het and the remaining part of to formula (I), preferably wherein $R^a$ is halogen, more preferably wherein $R^a$ is Cl.

In another embodiment, Het is selected from D-2a, and D-27a, wherein $R^a$ is halogen, preferably wherein $R^a$ is Cl. In another embodiment, Het is D-2a, wherein $R^a$ is halogen, preferably wherein $R^a$ is Cl. In another embodiment, Het is D-27a, wherein $R^a$ is halogen, preferably wherein $R^a$ is Cl.

In another embodiment Het is D-2, preferably D-2a, more preferably D-2a, wherein $R^a$ is Cl. In another embodiment, Het is D-9, preferably D-9a. In another embodiment, Het is D-27, preferably D-27a, more preferably D-27a, wherein $R^a$ is Cl.

In another embodiment Het is selected from the following rings D-1aa, D-2aa, D-9a, and D-27aa.

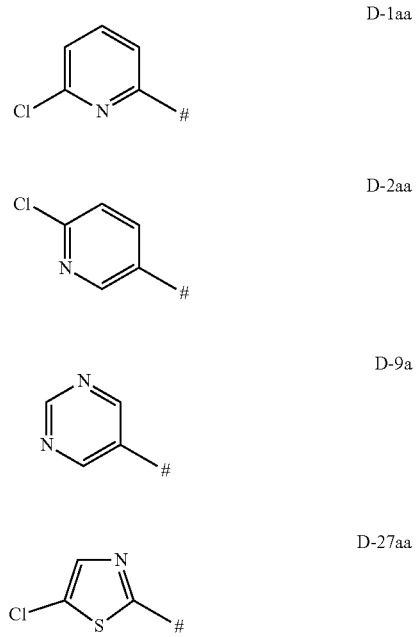

D-1aa

D-2aa

D-9a

D-27aa

In one embodiment, the compounds of formula (I) have the following stereochemistry as in formula (I-R):

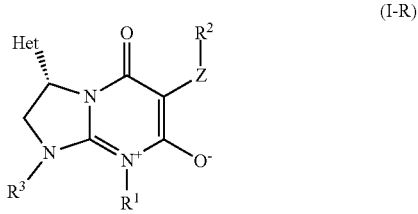

(I-R)

In another embodiment, the compounds of formula (I) have the following stereochemistry as in formula (I-S):

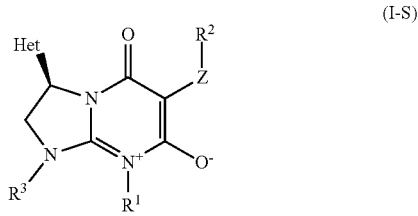

(I-S)

The compounds of formula (I-R) show a higher pesticidal efficacy compared to their stereoisomers of formula (I-S), as is proven by biological examples.

Each of the groups mentioned for the substituents in Table A is per se, independently of the combination in which they are mentioned, a particularly preferred aspect of the substituent in question. Each row of Table A individually represents an embodiment of compounds of formula (I), wherein Z is a direct bond, O, $S(O)_m$, $NR^b$, $C(R^aR^{aa})O$, $C(=X^1)$, $C(=X^1)Y^1$, or $Y^1C(=X^1)$; preferably wherein Z is a direct bond.

TABLE A

| Compound No | R¹ | R² | R³ | Het |
|---|---|---|---|---|
| I-1 | $CH_3$ | phenyl | $C(=O)OC(CH_3)_3$ | D-2aa |
| I-2 | $CH_3$ | phenyl | $CH_3$ | D-2aa |
| I-3 | $CH_3$ | phenyl | $CH_2CH_3$ | D-2aa |
| I-4 | $CH_3$ | 3,5-dichlorophenyl | $C(=O)OC(CH_3)_3$ | D-2aa |
| I-5 | $CH_3$ | 3,5-dichlorophenyl | $CH_3$ | D-2aa |
| I-6 | $CH_3$ | 3,5-dichlorophenyl | $CH_2CH_3$ | D-2aa |
| I-7 | $CH_3$ | 3-trifluoromethylphenyl | $C(=O)OC(CH_3)_3$ | D-2aa |
| I-8 | $CH_3$ | 3-trifluoromethylphenyl | $CH_3$ | D-2aa |
| I-9 | $CH_3$ | 3-trifluoromethylphenyl | $CH_2CH_3$ | D-2aa |
| I-10 | $CH_3$ | 4-methoxyphenyl | $C(=O)OC(CH_3)_3$ | D-2aa |
| I-11 | $CH_3$ | 4-methoxyphenyl | $CH_3$ | D-2aa |
| I-12 | $CH_3$ | 4-methoxyphenyl | $CH_2CH_3$ | D-2aa |
| I-13 | $CH_3$ | 3-difluoromethylphenyl | $C(=O)OC(CH_3)_3$ | D-2aa |
| I-14 | $CH_3$ | 3-difluoromethylphenyl | $CH_3$ | D-2aa |
| I-15 | $CH_3$ | 3-difluoromethylphenyl | $CH_2CH_3$ | D-2aa |
| I-16 | $CH_3$ | phenyl | $C(=O)OC(CH_3)_3$ | D-27aa |
| I-17 | $CH_3$ | phenyl | $CH_3$ | D-27aa |
| I-18 | $CH_3$ | phenyl | $CH_2CH_3$ | D-27aa |
| I-19 | $CH_3$ | 3,5-dichlorophenyl | $C(=O)OC(CH_3)_3$ | D-27aa |
| I-20 | $CH_3$ | 3,5-dichlorophenyl | $CH_3$ | D-27aa |
| I-21 | $CH_3$ | 3,5-dichlorophenyl | $CH_2CH_3$ | D-27aa |
| I-22 | $CH_3$ | 3-trifluoromethylphenyl | $C(=O)OC(CH_3)_3$ | D-27aa |
| I-23 | $CH_3$ | 3-trifluoromethylphenyl | $CH_3$ | D-27aa |
| I-24 | $CH_3$ | 3-trifluoromethylphenyl | $CH_2CH_3$ | D-27aa |
| I-25 | $CH_3$ | 4-methoxyphenyl | $C(=O)OC(CH_3)_3$ | D-27aa |
| I-26 | $CH_3$ | 4-methoxyphenyl | $CH_3$ | D-27aa |
| I-27 | $CH_3$ | 4-methoxyphenyl | $CH_2CH_3$ | D-27aa |
| I-28 | $CH_3$ | 3-difluoromethylphenyl | $C(=O)OC(CH_3)_3$ | D-27aa |
| I-29 | $CH_3$ | 3-difluoromethylphenyl | $CH_3$ | D-27aa |
| I-30 | $CH_3$ | 3-difluoromethylphenyl | $CH_2CH_3$ | D-27aa |
| I-31 | $CH_2CH_3$ | phenyl | $C(=O)OC(CH_3)_3$ | D-2aa |
| I-32 | $CH_2CH_3$ | phenyl | $CH_3$ | D-2aa |
| I-33 | $CH_2CH_3$ | phenyl | $CH_2CH_3$ | D-2aa |
| I-34 | $CH_2CH_3$ | 3,5-dichlorophenyl | $C(=O)OC(CH_3)_3$ | D-2aa |
| I-35 | $CH_2CH_3$ | 3,5-dichlorophenyl | $CH_3$ | D-2aa |
| I-36 | $CH_2CH_3$ | 3,5-dichlorophenyl | $CH_2CH_3$ | D-2aa |
| I-37 | $CH_2CH_3$ | 3-trifluoromethylphenyl | $C(=O)OC(CH_3)_3$ | D-2aa |
| I-38 | $CH_2CH_3$ | 3-trifluoromethylphenyl | $CH_3$ | D-2aa |
| I-39 | $CH_2CH_3$ | 3-trifluoromethylphenyl | $CH_2CH_3$ | D-2aa |
| I-40 | $CH_2CH_3$ | 4-methoxyphenyl | $C(=O)OC(CH_3)_3$ | D-2aa |
| I-41 | $CH_2CH_3$ | 4-methoxyphenyl | $CH_3$ | D-2aa |
| I-42 | $CH_2CH_3$ | 4-methoxyphenyl | $CH_2CH_3$ | D-2aa |
| I-43 | $CH_2CH_3$ | 3-difluoromethylphenyl | $C(=O)OC(CH_3)_3$ | D-2aa |
| I-44 | $CH_2CH_3$ | 3-difluoromethylphenyl | $CH_3$ | D-2aa |
| I-45 | $CH_2CH_3$ | 3-difluoromethylphenyl | $CH_2CH_3$ | D-2aa |
| I-46 | $CH_2CH_3$ | phenyl | $C(=O)OC(CH_3)_3$ | D-27aa |
| I-47 | $CH_2CH_3$ | phenyl | $CH_3$ | D-27aa |
| I-48 | $CH_2CH_3$ | phenyl | $CH_2CH_3$ | D-27aa |
| I-49 | $CH_2CH_3$ | 3,5-dichlorophenyl | $C(=O)OC(CH_3)_3$ | D-27aa |
| I-50 | $CH_2CH_3$ | 3,5-dichlorophenyl | $CH_3$ | D-27aa |
| I-51 | $CH_2CH_3$ | 3,5-dichlorophenyl | $CH_2CH_3$ | D-27aa |
| I-52 | $CH_2CH_3$ | 3-trifluoromethylphenyl | $C(=O)OC(CH_3)_3$ | D-27aa |
| I-53 | $CH_2CH_3$ | 3-trifluoromethylphenyl | $CH_3$ | D-27aa |
| I-54 | $CH_2CH_3$ | 3-trifluoromethylphenyl | $CH_2CH_3$ | D-27aa |
| I-55 | $CH_2CH_3$ | 4-methoxyphenyl | $C(=O)OC(CH_3)_3$ | D-27aa |
| I-56 | $CH_2CH_3$ | 4-methoxyphenyl | $CH_3$ | D-27aa |
| I-57 | $CH_2CH_3$ | 4-methoxyphenyl | $CH_2CH_3$ | D-27aa |
| I-58 | $CH_2CH_3$ | 3-difluoromethylphenyl | $C(=O)OC(CH_3)_3$ | D-27aa |
| I-59 | $CH_2CH_3$ | 3-difluoromethylphenyl | $CH_3$ | D-27aa |
| I-60 | $CH_2CH_3$ | 3-difluoromethylphenyl | $CH_2CH_3$ | D-27aa |
| I-61 | $CH_3$ | phenyl | $C(=O)OC(CH_3)_3$ | D-1aa |
| I-62 | $CH_3$ | phenyl | $CH_3$ | D-1aa |
| I-63 | $CH_3$ | phenyl | $CH_2CH_3$ | D-1aa |
| I-64 | $CH_3$ | 3,5-dichlorophenyl | $C(=O)OC(CH_3)_3$ | D-1aa |
| I-65 | $CH_3$ | 3,5-dichlorophenyl | $CH_3$ | D-1aa |
| I-66 | $CH_3$ | 3,5-dichlorophenyl | $CH_2CH_3$ | D-1aa |
| I-67 | $CH_3$ | 3-trifluoromethylphenyl | $C(=O)OC(CH_3)_3$ | D-1aa |
| I-68 | $CH_3$ | 3-trifluoromethylphenyl | $CH_3$ | D-1aa |
| I-69 | $CH_3$ | 3-trifluoromethylphenyl | $CH_2CH_3$ | D-1aa |
| I-70 | $CH_3$ | 4-methoxyphenyl | $C(=O)OC(CH_3)_3$ | D-1aa |
| I-71 | $CH_3$ | 4-methoxyphenyl | $CH_3$ | D-1aa |
| I-72 | $CH_3$ | 4-methoxyphenyl | $CH_2CH_3$ | D-1aa |
| I-73 | $CH_3$ | 3-difluoromethylphenyl | $C(=O)OC(CH_3)_3$ | D-1aa |
| I-74 | $CH_3$ | 3-difluoromethylphenyl | $CH_3$ | D-1aa |
| I-75 | $CH_3$ | 3-difluoromethylphenyl | $CH_2CH_3$ | D-1aa |
| I-76 | $CH_2CH_3$ | phenyl | $C(=O)OC(CH_3)_3$ | D-1aa |
| I-77 | $CH_2CH_3$ | phenyl | $CH_3$ | D-1aa |
| I-78 | $CH_2CH_3$ | phenyl | $CH_2CH_3$ | D-1aa |
| I-79 | $CH_2CH_3$ | 3,5-dichlorophenyl | $C(=O)OC(CH_3)_3$ | D-1aa |
| I-80 | $CH_2CH_3$ | 3,5-dichlorophenyl | $CH_3$ | D-1aa |
| I-81 | $CH_2CH_3$ | 3,5-dichlorophenyl | $CH_2CH_3$ | D-1aa |
| I-82 | $CH_2CH_3$ | 3-trifluoromethylphenyl | $C(=O)OC(CH_3)_3$ | D-1aa |
| I-83 | $CH_2CH_3$ | 3-trifluoromethylphenyl | $CH_3$ | D-1aa |
| I-84 | $CH_2CH_3$ | 3-trifluoromethylphenyl | $CH_2CH_3$ | D-1aa |
| I-85 | $CH_2CH_3$ | 4-methoxyphenyl | $C(=O)OC(CH_3)_3$ | D-1aa |
| I-86 | $CH_2CH_3$ | 4-methoxyphenyl | $CH_3$ | D-1aa |
| I-87 | $CH_2CH_3$ | 4-methoxyphenyl | $CH_2CH_3$ | D-1aa |
| I-88 | $CH_2CH_3$ | 3-difluoromethylphenyl | $C(=O)OC(CH_3)_3$ | D-1aa |
| I-89 | $CH_2CH_3$ | 3-difluoromethylphenyl | $CH_3$ | D-1aa |
| I-90 | $CH_2CH_3$ | 3-difluoromethylphenyl | $CH_2CH_3$ | D-1aa |

In one embodiment, the compounds of formula (I) are selected from compounds of formula (I), preferably from compounds of formula (I-R), wherein the variables Z, $R^1$, $R^2$, $R^3$, and Het have the following meaning:

Z is a direct bond;

$R^1$ is $C_1$-$C_4$-alkyl or —$CH_2$-phenyl;

$R^2$ phenyl, —$CH_2$-phenyl, —$CH(CH_3)$-phenyl, or —O—$CH_2$-phenyl, wherein the phenyl ring is unsubstituted, partially or fully substituted with halogen, CN, $C_1$-$C_3$-alkyl, $C_1$-$C_3$-haloalkyl, $C_1$-$C_3$-alkoxy, or $C_1$-$C_3$-haloalkoxy, preferably phenyl, 3,5-dichlorophenyl, 3-trifluoromethylphenyl, 3-difluoromethylphenyl, or 4-methoxyphenyl.

$R^3$ is $C_1$-$C_3$-alkyl or $C(=O)O$—$C_1$-$C_4$-alkyl;

Het is D-1, D-2, D-9, or D-27, wherein the index n is 1, preferably D-1a, D-2a, D-9a, or D-27a, more preferably D-1aa, D-2aa or D-27aa.

In one embodiment, the compounds of formula (I) are selected from compounds of formula (I), preferably from compounds of formula (I-R), wherein the variables Z, $R^1$, $R^2$, $R^3$, and Het have the following meaning:

Z is a direct bond;

$R^1$ is $C_1$-$C_4$-alkyl;

$R^2$ phenyl, which is unsubstituted, partially or fully substituted with halogen, $C_1$-$C_3$-alkyl, $C_1$-$C_3$-haloalkyl, $C_1$-$C_3$-alkoxy, or $C_1$-$C_3$-haloalkoxy, preferably phenyl, 3,5-dichlorophenyl, 3-trifluoromethylphenyl, 3-difluoromethylphenyl, or 4-methoxyphenyl.

$R^3$ is $C_1$-$C_3$-alkyl or $C(=O)O$—$C_1$-$C_4$-alkyl;

Het is D-2, D-9, or D-27, wherein the index n is 1, preferably D-2aa or D-27aa.

In one embodiment, the compounds of formula (I) are selected from compounds of formula (I), preferably from compounds of formula (I-R), wherein the variables Z, $R^1$, $R^2$, $R^3$, and Het have the following meaning:

Z is a direct bond;

$R^1$ is $CH_3$, or $CH_2CH_3$;

$R^2$ is 4-methoxyphenyl, 3-difluoromethylphenyl, 3-trifluoromethylphenyl, 3,5-dichlorophenyl, or phenyl;

$R^3$ is $CH_3$, $CH_2CH_3$, or $C(=O)OC(CH_3)_3$;

Het is D-2aa, or D-27aa.

In another embodiment, the compounds of formula (I) are selected from compounds of formula (I-S), wherein the variables Z, $R^1$, $R^2$, $R^3$, and Het have the following meaning:

Z is a direct bond;

$R^1$ is $C_1$-$C_4$-alkyl;

$R^2$ phenyl, which is unsubstituted, partially or fully substituted with halogen, $C_1$-$C_3$-alkyl, $C_1$-$C_3$-haloalkyl, $C_1$-$C_3$-alkoxy, or $C_1$-$C_3$-haloalkoxy, preferably phenyl, 3,5-dichlorophenyl, 3-trifluoromethylphenyl, 3-difluoromethylphenyl, or 4-methoxyphenyl.

$R^3$ is $C_1$-$C_3$-alkyl or C(=O)O—$C_1$-$C_4$-alkyl;

Het is D-2, D-9, or D-27, wherein the index n is 1, preferably D-2aa or D-27aa.

In another embodiment, the compounds of formula (I) are selected from compounds of formula (I-S), wherein the variables Z, $R^1$, $R^2$, $R^3$, and Het have the following meaning:

Z is a direct bond;

$R^1$ is $CH_3$, or $CH_2CH_3$;

$R^2$ is 4-methoxyphenyl, 3-difluoromethylphenyl, 3-trifluoromethylphenyl, 3,5-dichlorophenyl, or phenyl;

$R^3$ is $CH_3$, $CH_2CH_3$, or C(=O)OC($CH_3$)$_3$;

Het is D-2aa, or D-27aa.

In one embodiment, the variables $R^1$, $R^2$, $R^3$, and Het in formula (I), preferably in formula (I-R), have a meaning as defined for a compound I-1 to I-60 in Table A, and Z is a direct bond. In another embodiment, the variables $R^1$, $R^2$, $R^3$, and Het in formula (I-S) have a meaning as defined for a compound I-1 to I-60 in Table A, and Z is a direct bond.

The present invention also relates to a pesticidal mixture of at least one compound of formula (I) with another agrochemically active ingredient. ##Preferred are binary mixtures of one compound of formula (I) as component I with one mixing partner as defined herein as component II. Preferred weight ratios for such binary mixtures are from 5000:1 to 1:5000, preferably from 1000:1 to 1:1000, more preferably from 100:1 to 1:100, particularly from 10:1 to 1:10. In such binary mixtures, components I and II may be used in equal amounts, or an excess of component I, or an excess of component II may be used.

Mixing partners can be selected from pesticides, in particular insecticides, nematicides, and acaricides, fungicides, herbicides, plant growth regulators, fertilizers. Preferred mixing partners are insecticides, nematicides and fungicides, more preferred insecticides and fungicides.

The following list M of pesticides, grouped and numbered according the Mode of Action Classification of the Insecticide Resistance Action Committee (IRAC), together with which the compounds of the invention can be used and with which potential synergistic effects might be produced, is intended to illustrate the possible combinations, but not to impose any limitation:

M.1 Acetylcholine esterase (AChE) inhibitors: M.1A carbamates, e.g. aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or M.1B organophosphates, e.g. acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, and vamidothion;

M.2. GABA-gated chloride channel antagonists: M.2A cyclodiene organochlorine compounds, e.g. endosulfan or chlordane; or M.2B fiproles (phenylpyrazoles), e.g. ethiprole, fipronil, flufiprole, pyrafluprole, and pyriprole;

M.3 Sodium channel modulators from the class of M.3A pyrethroids, e.g. acrinathrin, allethrin, d-cis-trans allethrin, d-trans allethrin, bifenthrin, bioallethrin, bioallethrin S-cyclopentenyl, bio-resmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin, and transfluthrin; or M.3B sodium channel modulators such as DDT or methoxychlor; M.4 Nicotinic acetylcholine receptor agonists (nAChR): M.4A neonicotinoids, e.g. acetamiprid, clothianidin, cycloxaprid, dinotefuran, imidacloprid, nitenpyram, thiacloprid and thiamethoxam; or the compounds M.4A.1 4,5-Dihydro-N-nitro-1-(2-oxiranylmethyl)-1H-imidazol-2-amine, M.4A.2: (2E-)-1-[(6-Chloropyridin-3-yl)methyl]-N'-nitro-2-pentylidenehydrazinecarboximidamide; or M4.A.3: 1-[(6-Chloropyridin-3-yl)methyl]-7-methyl-8-nitro-5-propoxy-1,2,3,5,6,7-hexahydroimidazo[1,2-a]pyridine; or M.4B nicotine; M.4C sulfoxaflor; M.4D flupyradifurone; M.4E triflumezopyrim;

M.5 Nicotinic acetylcholine receptor allosteric activators: spinosyns, e.g. spinosad or spinetoram;

M.6 Chloride channel activators from the class of avermectins and milbemycins, e.g. abamectin, emamectin benzoate, ivermectin, lepimectin, or milbemectin;

M.7 Juvenile hormone mimics, such as M.7A juvenile hormone analogues hydroprene, kinoprene, and methoprene; or M.7B fenoxycarb, or M.7C pyriproxyfen;

M.8 miscellaneous non-specific (multi-site) inhibitors, e.g. M.8A alkyl halides as methyl bromide and other alkyl halides, M.8B chloropicrin, M.8C sulfuryl fluoride, M.8D borax, or M.8E tartar emetic;

M.9 Chordotonal organ TRPV channel modulators, e.g. M.9B pymetrozine; pyrifluquinazon; M.10 Mite growth inhibitors, e.g. M.10A clofentezine, hexythiazox, and diflovidazin, or M.10B etoxazole;

M.11 Microbial disruptors of insect midgut membranes, e.g. *Bacillus thuringiensis* or *Bacillus sphaericus* and the insecticidal proteins they produce such as *Bacillus thuringiensis* subsp. *israelensis, Bacillus sphaericus, Bacillus thuringiensis* subsp. *aizawai, Bacillus thuringiensis* subsp. *kurstaki* and *Bacillus thuringiensis* subsp. *tenebrionis*, or the Bt crop proteins: Cry1Ab, Cry1Ac, Cry1Fa, Cry2Ab, mCry3A, Cry3Ab, Cry3Bb, and Cry34/35Ab1; M.12 Inhibitors of mitochondrial ATP synthase, e.g. M.12A diafenthiuron, or M.12B organotin miticides such as azocyclotin, cyhexatin, or fenbutatin oxide, M.12C propargite, or M.12D tetradifon;

M.13 Uncouplers of oxidative phosphorylation via disruption of the proton gradient, e.g. chlorfenapyr, DNOC, or sulfluramid;

M.14 Nicotinic acetylcholine receptor (nAChR) channel blockers, e.g. nereistoxin analogues bensultap, cartap hydrochloride, thiocyclam, or thiosultap sodium;

M.15 Inhibitors of the chitin biosynthesis type 0, such as benzoylureas e.g. bistrifluron, chlorfluazuron, diflubenzuron, flucycloxuron, flufenoxuron, hexaflumuron, lufenuron, novaluron, noviflumuron, teflubenzuron, or triflumuron;

M.16 Inhibitors of the chitin biosynthesis type 1, e.g. buprofezin;

M.17 Moulting disruptors, Dipteran, e.g. cyromazine;

M.18 Ecdyson receptor agonists such as diacylhydrazines, e.g. methoxyfenozide, tebufenozide, halofenozide, fufenozide, or chromafenozide;

M.19 Octopamin receptor agonists, e.g. amitraz;

M.20 Mitochondrial complex III electron transport inhibitors, e.g. M.20A hydramethylnon, M.20B acequinocyl, M.20C fluacrypyrim; or M.20D bifenazate;

M.21 Mitochondrial complex I electron transport inhibitors, e.g. M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, e.g. M.22A indoxacarb, M.22B metaflumizone, or M.22B.1: 2-[2-(4-Cyanophenyl)-1-[3-(trifluoromethyl)phenyl]ethylidene]-N-[4-(difluoromethoxy)phenyl]-hydrazinecarboxamide or M.22B.2: N-(3-Chloro-2-methylphenyl)-2-[(4-chlorophenyl)[4-[methyl(methylsulfonyl)amino]phenyl]methylene]-hydrazinecarboxamide;

M.23 Inhibitors of the of acetyl CoA carboxylase, such as Tetronic and Tetramic acid derivatives, e.g. spirodiclofen, spiromesifen, or spirotetramat; M.23.1 spiropidion M.24 Mitochondrial complex IV electron transport inhibitors, e.g. M.24A phosphine such as aluminium phosphide, calcium phosphide, phosphine or zinc phosphide, or M.24B cyanide;

M.25 Mitochondrial complex II electron transport inhibitors, such as beta-ketonitrile derivatives, e.g. cyenopyrafen or cyflumetofen;

M.28 Ryanodine receptor-modulators from the class of diamides, e.g. flubendiamide, chlorantraniliprole, cyantraniliprole, tetraniliprole, M.28.1: (R)-3-Chlor-N1-{2-methyl-4-[1,2,2,2-tetrafluoro-1-(trifluoromethyl)ethyl]phenyl}-N2-(1-methyl-2-methylsulfonylethyl)phthalamid, M.28.2: (S)-3-Chloro-N1-{2-methyl-4-[1,2,2,2-tetrafluoro-1-(trifluoromethyl)ethyl]phenyl}-N2-(1-methyl-2-methylsulfonylethyl)phthalamid, M.28.3: cyclaniliprole, or M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or M.28.5a) N-[4,6-dichloro-2-[(diethyl-lambda-4-sulfanylidene)-carbamoyl]-phenyl]-2-(3-chloro-2-pyridyl)-5-(trifluoromethyl)pyrazole-3-carboxamide; M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide; M.28.5c) N-[4-chloro-2-[(di-2-propyl-lambda-4-sulfanyl idene)carbamoyl]-6-methyl-phenyl]-2-(3-chloro-2-pyridyl)-5-(trifluoromethyl)pyrazole-3-carboxamide; M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide; M.28.5i) N-[2-(5-Amino-1,3,4-thiadiazol-2-yl)-4-chloro-6-methyl phenyl]-3-bromo-1-(3-chloro-2-pyridinyl)-1H-pyrazole-5-carboxamide; M.28.5j) 3-Chloro-1-(3-chloro-2-pyridinyl)-N-[2,4-dichloro-6-[[(1-cyano-1-methylethyl)amino]carbonyl]phenyl]-1H-pyrazole-5-carboxamide; M.28.5k) 3-Bromo-N-[2,4-dichloro-6-(methylcarbamoyl)phenyl]-1-(3,5-dichloro-2-pyridyl)-1H-pyrazole-5-carboxamide; M.28.5I) N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide; or M.28.6: cyhalodiamide; or M.29: Chordotonal organ Modulators—undefined target site, e.g. flonicamid;

M.UN. insecticidal active compounds of unknown or uncertain mode of action, e.g. afidopyropen, afoxolaner, azadirachtin, amidoflumet, benzoximate, broflanilide, bromopropylate, chinomethionat, cryolite, dicloromezotiaz, dicofol, flufenerim, flometoquin, fluensulfone, fluhexafon, fluopyram, fluralaner, metoxadiazone, piperonyl butoxide, pyflubumide, pyridalyl, tioxazafen, M.UN.3: 11-(4-chloro-2,6-dimethylphenyl)-12-hydroxy-1,4-dioxa-9-azadispiro[4.2.4.2]-tetradec-11-en-10-one, M. UN.4: 3-(4'-fluoro-2,4-dimethylbiphenyl-3-yl)-4-hydroxy-8-oxa-1-azaspiro[4.5]dec-3-en-2-one, M. UN.5:1-[2-fluoro-4-methyl-5-[(2,2,2-trifluoroethyl)sulfinyl]phenyl]-3-(trifluoromethyl)-1H-1,2,4-triazole-5-amine, or actives on basis of *Bacillus firmus* (Votivo, I-1582);

M.UN.6: flupyrimin;

M.UN.8: fluazaindolizine; M.UN.9.a): 4-[5-(3,5-dichlorophenyl)-5-(trifluoromethyl)-4H-isoxazol-3-yl]-2-methyl-N-(1-oxothietan-3-yl)benzamide; M.UN.9.b): fluxametamide; M.UN.10: 5-[3-[2,6-dichloro-4-(3,3-dichloroallyloxy)phenoxy]propoxy]-1H-pyrazole;

M.UN.11.b) 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide; M.UN.11.c) 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide; M.UN.11.d) N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.UN.11.e) N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methyl-benzamide; M.UN.11.f) 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.UN.11.g) 3-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.UN.11.h) 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide; M.UN.11.i) 4-cyano-N-[2-cyano-5-[[2,6-dibromo-4-[1,2,2,3,3,3-hexafluoro-1-(trifluoromethyl)-propyl]phenyl]carbamoyl]phenyl]-2-methyl-benzamide; M.UN.11.j) 4-cyano-3-[(4-cyano-2-methyl-benzoyl)amino]-N-[2,6-dichloro-4-[1,2,2,3,3,3-hexafluoro-1-(trifluoromethyl)-propyl]phenyl]-2-fluoro-benzamide; M.UN.11.k) N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide; M. UN.11.l) N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide; M.UN.11.m) N-[5-[[2-bromo-6-chloro-4-[1,2,2,3,3,3-hexafluoro-1-(trifluoromethyl)-propyl]phenyl]carbamoyl]-2-cyano-phenyl]-4-cyano-2-methyl-benzamide; M.UN.11.n) 4-cyano-N-[2-cyano-5-[[2,6-dichloro-4-[1,2,2,3,3,3-hexafluoro-1-(trifluoromethyl)-propyl]phenyl]carbamoyl]phenyl]-2-methyl-benzamide; M.UN.11.o) 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide; M.UN.11.p) N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide; or M.UN.12.a) 2-(1,3-Dioxan-2-yl)-6-[2-(3-pyridinyl)-5-thiazolyl]-pyridine; M.UN.12.b) 2-[6-[2-(5-Fluoro-3-pyridinyl)-5-thiazolyl]-2-pyridinyl]-pyrimidine; M.UN.12.c) 2-[6-[2-(3-Pyridinyl)-5-thiazolyl]-2-pyridinyl]-pyrimidine; M.UN.12.d) N-Methylsulfonyl-6-[2-(3-pyridyl)thiazol-5-yl]pyridine-2-carboxamide; M.UN.12.e) N-Methylsulfonyl-6-[2-(3-pyridyl)thiazol-5-yl]pyridine-2-carboxamide;

M.UN.12.f) N-Ethyl-N-[4-methyl-2-(3-pyridyl)thiazol-5-yl]-3-methylthio-propanamide; M.UN.12.g) N-Methyl-N-[4-methyl-2-(3-pyridyl)thiazol-5-yl]-3-methylthio-propanamide; M. UN.12.h) N,2-Dimethyl-N-[4-methyl-2-(3-pyridyl)thiazol-5-yl]-3-methylthio-propanamide;

M.UN.12.i) N-Ethyl-2-methyl-N-[4-methyl-2-(3-pyridyl)thiazol-5-yl]-3-methylthio-propanamide; M.UN.12.j) N-[4-Chloro-2-(3-pyridyl)thiazol-5-yl]-N-ethyl-2-methyl-3-methylthio-propanamide; M.UN.12.k) N-[4-Chloro-2-(3-pyridyl)thiazol-5-yl]-N,2-dimethyl-3-methylthio-propanamide; M.UN.12.l) N-[4-Chloro-2-(3-pyridyl)thiazol-5-yl]-N-methyl-3-methylthio-propanamide;

M.UN.12.m) N-[4-Chloro-2-(3-pyridyl)thiazol-5-yl]-N-ethyl-3-methylthio-propanamide;

M.UN.14a) 1-[(6-Chloro-3-pyridinyl)methyl]-1,2,3,5,6,7-hexahydro-5-methoxy-7-methyl-8-nitro-imidazo[1,2-a]pyridine; or M.UN.14b) 1-[(6-Chloropyridin-3-yl)methyl]-7-methyl-8-nitro-1,2,3,5,6,7-hexahydroimidazo[1,2-a]pyridin-5-ol;

M.UN.16a) 1-isopropyl-N,5-dimethyl-N-pyridazin-4-yl-pyrazole-4-carboxamide; or M.UN.16b) 1-(1,2-dimethylpropyl)-N-ethyl-5-methyl-N-pyridazin-4-yl-pyrazole-4-carboxamide; M.UN.16c) N,5-dimethyl-N-pyridazin-4-yl-1-(2,2,2-trifluoro-1-methyl-ethyl)pyrazole-4-carboxamide;

M.UN.16d) 1-[1-(1-cyanocyclopropyl)ethyl]-N-ethyl-5-methyl-N-pyridazin-4-yl-pyrazole-4-carboxamide; M.UN.16e) N-ethyl-1-(2-fluoro-1-methyl-propyl)-5-methyl-N-pyridazin-4-yl-pyrazole-4-carboxamide; M.UN.16f) 1-(1,2-dimethylpropyl)-N,5-dimethyl-N-pyridazin-4-yl-pyrazole-4-carboxamide; M.UN.16g) 1-[1-(1-cyanocyclopropyl)ethyl]-N,5-dimethyl-N-pyridazin-4-yl-pyrazole-4-carboxamide; M.UN.16h) N-methyl-1-(2-fluoro-1-methyl-propyl]-5-methyl-N-pyridazin-4-yl-pyrazole-4-carboxamide; M.UN.16i) 1-(4,4-difluorocyclohexyl)-N-ethyl-5-methyl-N-pyridazin-4-yl-pyrazole-4-carboxamide; or M.UN.16j) 1-(4,4-difluorocyclohexyl)-N,5-dimethyl-N-pyridazin-4-yl-pyrazole-4-carboxamide, M.UN.17a) N-(1-methylethyl)-2-(3-pyridinyl)-2H-indazole-4-carboxamide; M.UN.17b) N-cyclopropyl-2-(3-pyridinyl)-2H-indazole-4-carboxamide; M.UN.17c) N-cyclohexyl-2-(3-pyridinyl)-2H-indazole-4-carboxamide;

M.UN.17d) 2-(3-pyridinyl)-N-(2,2,2-trifluoroethyl)-2H-indazole-4-carboxamide; M.UN.17e) 2-(3-pyridinyl)-N-[(tetrahydro-2-furanyl)methyl]-2H-indazole-5-carboxamide;

M.UN.17f) methyl 2-[[2-(3-pyridinyl)-2H-indazol-5-yl]carbonyl]hydrazinecarboxylate; M.UN.17g) N-[(2,2-difluorocyclopropyl)methyl]-2-(3-pyridinyl)-2H-indazole-5-carboxamide; M.UN.17h) N-(2,2-difluoropropyl)-2-(3-pyridinyl)-2H-indazole-5-carboxamide; M.UN.17i) 2-(3-pyridinyl)-N-(2-pyrimidinylmethyl)-2H-indazole-5-carboxamide; M.UN.17j) N-[(5-methyl-2-pyrazinyl)methyl]-2-(3-pyridinyl)-2H-indazole-5-carboxamide, M.UN.18a) N-[3-chloro-1-(3-pyridyl)pyrazol-4-yl]-N-ethyl-3-(3,3,3-trifluoropropylsulfanyl)propanamide; M.UN.18b) N-[3-chloro-1-(3-pyridyl)pyrazol-4-yl]-N-ethyl-3-(3,3,3-trifluoropropylsulfinyl)propanamide; M.UN.18c) N-[3-chloro-1-(3-pyridyl)pyrazol-4-yl]-3-[(2,2-difluorocyclopropyl)methylsulfanyl]-N-ethyl-propanamide; M.UN.18d) N-[3-chloro-1-(3-pyridyl)pyrazol-4-yl]-3-[(2,2-difluorocyclopropyl)methylsulfinyl]-N-ethyl-propanamide;

M.UN.19 sarolaner, M.UN.20 lotilaner;

M.UN.21 N-[4-Chloro-3-[[(phenylmethyl)amino]carbonyl]phenyl]-1-methyl-3-(1,1,2,2,2-pentafluoroethyl)-4-(trifluoromethyl)-1H-pyrazole-5-carboxamide; M.UN.22a 2-(3-ethylsulfonyl-2-pyridyl)-3-methyl-6-(trifluoromethyl)imidazo[4,5-b]pyridine, or M.UN.22b 2-[3-ethylsulfonyl-5-(trifluoromethyl)-2-pyridyl]-3-methyl-6-(trifluoromethyl)imidazo[4,5-b]pyridine;

M.UN.23a 4-[5-(3,5-dichlorophenyl)-5-(trifluoromethyl)-4H-isoxazol-3-yl]-N-[(4R)-2-ethyl-3-oxo-isoxazolidin-4-yl]-2-methyl-benzamide, or M.UN.23b 4-[5-(3,5-dichloro-4-fluoro-phenyl)-5-(trifluoromethyl)-4H-isoxazol-3-yl]-N-[(4R)-2-ethyl-3-oxo-isoxazolidin-4-yl]-2-methyl-benzamide;

M. UN.24a) N-[4-chloro-3-(cyclopropylcarbamoyl)phenyl]-2-methyl-5-(1,1,2,2,2-pentafluoroethyl)-4-(trifluoromethyl)pyrazole-3-carboxamide or M.UN.24b) N-[4-chloro-3-[(1-cyanocyclopropyl)carbamoyl]phenyl]-2-methyl-5-(1,1,2,2,2-pentafluoroethyl)-4-(trifluoromethyl)pyrazole-3-carboxamide; M.UN.25 acynonapyr; M.UN.26 benzpyrimoxan;

M.UN.27 2-chloro-N-(1-cyanocyclopropyl)-5-[1-[2-methyl-5-(1,1,2,2,2-pentafluoroethyl)-4-(trifluoromethyl)pyrazol-3-yl]pyrazol-4-yl]benzamide.

The commercially available compounds of the group M listed above may be found in The Pesticide Manual, 17th Edition, C. MacBean, British Crop Protection Council (2015) among other publications. The online Pesticide Manual is updated regularly and is accessible through http://bcpcdata.com/pesticide-manual.html.

Another online data base for pesticides providing the ISO common names is http://www.alanwood.net/pesticides.

The M.4 cycloxaprid is known from WO2010/069266 and WO2011/069456. M.4A.1 is known from CN 103814937; CN105367557, CN 105481839. M.4A.2, guadipyr, is known from WO 2013/003977, and M.4A.3 (approved as paichongding in China) is known from WO 2007/101369. M.22B.1 is described in CN10171577 and M.22B.2 in CN102126994. Spiropidion M.23.1 is known from WO 2014/191271. M.28.1 and M.28.2 are known from WO2007/101540. M.28.3 is described in WO2005/077934. M.28.4 is described in WO2007/043677. M.28.5a) to M.28.5d) and M.28.5h) are described in WO 2007/006670, WO2013/024009 and WO 2013/024010, M.28.5i) is described in WO2011/085575, M.28.5j) in WO2008/134969, M.28.5k) in US2011/046186 and M.28.5l) in WO2012/034403. M.28.6 can be found in WO2012/034472. M.UN.3 is known from WO2006/089633 and M.UN.4 from WO2008/067911. M.UN.5 is described in WO2006/043635, and biological control agents on the basis of *Bacillus firmus* are described in WO2009/124707. Flupyrimin is described in WO2012/029672. M.UN.8 is known from WO2013/055584. M.UN.9.a) is described in WO2013/050317. M.UN.9.b) is described in WO2014/126208. M.UN.10 is known from WO2010/060379. Broflanilide and M.UN.11.b) to M.UN.11.h) are described in WO2010/018714, and M.UN.11i) to M.UN.11.p) in WO 2010/127926. M.UN.12.a) to M.UN.12.c) are known from WO2010/006713, M.UN.12.d) and M.UN.12.e) are known from WO2012/000896, and M.UN.12.f) to M.UN.12.m) from WO 2010/129497. M.UN.14a) and M.UN.14b) are known from WO2007/101369. M.UN.16.a) to M.UN.16h) are described in WO2010/034737, WO2012/084670, and WO2012/143317, resp., and M.UN.16i) and M.UN.16j) are described in WO2015/055497. M.UN.17a) to M.UN.17.j) are described in WO2015/038503. M.UN.18a) to M.UN.18d) are described in US2014/0213448.

M.UN.19 is described in WO2014/036056. M.UN.20 is known from WO2014/090918. M.UN.21 is known from EP2910126. M.UN.22a and M.UN.22b are known from WO2015/059039 and WO2015/190316. M.UN.23a and M.UN.23b are known from WO2013/050302. M.UN.24a and M.UN.24b are known from WO2012/126766. Acynonapyr M.UN.25 is known from WO 2011/105506. Benzpyrimoxan M.UN.26 is known from WO2016/104516. M.UN.27 is known from WO2016174049.

The following list of fungicides, in conjunction with which the compounds of the present invention can be used, is intended to illustrate the possible combinations but does not limit them:

A) Respiration Inhibitors
  Inhibitors of complex III at Qo site: azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17), 2 (2-(3-(2,6-dichlorophenyl)-1-methyl-allylideneaminooxymethyl)-phenyl)-2 methoxyimino-N methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5 phenyl-pyrazol-3-yl)oxylmethyl]phenyl]-N-methoxy-carbamate (A.1.22), 1-[3-chloro-2 [[1 (4-chlorophenyl)-1H-pyrazol-3-yl]oxymethyl]phenyl]-4-methyl-tetrazol-5-one (A.1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl-tetrazol-5-one (A.1.25), 1-[2-[[1-(4-chlorophenyl)pyrazol-3-yl]oxymethyl]-3-fluoro-phenyl]-4-methyl-tetrazol-5-one (A. 1.26), 1-[2-[[1-(2,4-dichlorophenyl)pyrazol-3-yl]oxymethyl]-3-fluoro-phenyl]-4-methyl-tetrazol-5-one (A.1.27), 1-[3-cyclopropyl-2-[[2-methyl-4 (1 methylpyrazol-3-yl) phenoxy]methyl]phenyl]-4 methyl-tetrazol-5-one (A.1.30), 1 [3 (difluoromethoxy)-2-[[2-methyl-4-(1 methylpyrazol-3 yl)phenoxy]methyl]phenyl]-4 methyl-tetrazol-5-one (A.1.31), 1-methyl-4-[3-methyl-2 [[2 methyl-4-(1-methylpyrazol-3 yl)phenoxy]methyl]phenyl]tetrazol-5-one (A.1.32), (Z,2E)-5-[1-(2,4-dichlorophenyl)pyrazol-3-yl]-oxy-2-methoxyimino-N,3-dimethyl-pent-3-enamide (A.1.34), (Z,2E) 5 [1 (4-chlorophenyl)pyrazol-3-yl]oxy-2-methoxyimino-N,3-dimethyl-pent-3-enamide (A.1.35), pyriminostrobin (A.1.36), bifujunzhi (A.1.37), 2-(ortho-((2,5-dimethylphenyl-oxy-methylen)phenyl)-3-methoxy-acrylic acid methylester (A.1.38);
  inhibitors of complex III at Qi site: cyazofamid (A.2.1), amisulbrom (A.2.2), [(6S,7R,8R) 8 benzyl-3-[(3-hydroxy-4-methoxy-pyridine-2-carbonyl)amino]-6-methyl-4,9-dioxo-1,5-dioxonan-7-yl]2-methylpropanoate (A.2.3), fenpicoxamid (A.2.4);
  inhibitors of complex II: benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyrox-ad (A.3.9), furametpyr (A.3.10), isofetamid (A.3.11), isopyrazam (A.3.12), mepronil (A.3.13), oxycarboxin (A.3.14), penflufen (A.3.15), penthiopyrad (A.3.16), pydiflumetofen (A.3.17), pyraziflumid (A.3.18), sedaxane (A.3.19), tecloftalam (A.3.20), thifluzamide (A.3.21), 3 (difluoromethyl)-1-methyl-N-(1,1,3-trimethylindan-4-yl) pyrazole-4 carboxamide (A.3.22), 3 (trifluoromethyl)-1-methyl-N-(1,1,3-trimethylindan-4-yl)pyrazole-4 carboxamide (A.3.23), 1,3-dimethyl-N-(1,1,3-trimethylindan-4-yl)pyrazole-4-carboxamide (A.3.24), 3-(trifluoromethyl)-1,5 dimethyl-N-(1,1,3-trimethylindan-4-yl)pyrazole-4-carboxamide (A.3.25), 1,3,5-trimethyl-N-(1,1,3-trimethylindan-4-yl)pyrazole-4-carboxamide (A.3.26), 3-(difluoromethyl)-1,5 dimethyl-N-(1,1,3-trimethylindan-4-yl)pyrazole-4-carboxamide (A.3.27), 3-(difluoromethyl)-N (7 fluoro-1,1,3-trimethyl-indan-4-yl)-1-methyl-pyrazole-4-carboxamide (A.3.28), N-[(5-chloro-2-isopropyl-phenyl)methyl]-N-cyclopropyl-5-fluoro-1,3-dimethyl-pyrazole-4-carboxamide (A.3.29), methyl (E)-2-[2-[[(5-cyano-2-methyl-phenoxy)methyl]phenyl]-3-methoxy-prop-2 enoate (A.3.30), N-[(5-chloro-2-isopropyl-phenyl)methyl]-N-cyclopropyl-3-(difluoromethyl)-5 fluoro-1-methyl-pyrazole-4-carboxamide (A.3.31), 2-(difluoromethyl)-N-(1,1,3-trimethyl-indan-4-yl)pyridine-3-carboxamide (A.3.32), 2-(difluoromethyl)-N-[(3R)-1,1,3-trimethyl-indan-4-yl]pyridine-3-carboxamide (A.3.33), 2-(difluoromethyl)-N-(3-ethyl-1,1-dimethyl-indan-4-yl) pyridine-3-carboxamide (A.3.34), 2-(difluoromethyl)-N-[(3R)-3-ethyl-1,1-dimethyl-indan-4-yl]pyridine-3-carboxamide (A.3.35), 2-(difluoromethyl)-N-(1,1-dimethyl-3-propyl-indan-4-yl)pyridine-3-carboxamide (A.3.36), 2-(difluoromethyl)-N-[(3R)-1,1-dimethyl-3-propyl-indan-4-yl]pyridine-3-carboxamide (A.3.37), 2-(difluoromethyl)-N-(3-isobutyl-1,1-dimethyl-indan-4-yl)pyridine-3-carboxamide (A.3.38), 2-(difluoromethyl)-N-[(3R)-3-isobutyl-1,1-dimethyl-indan-4 yl]pyridine-3-carboxamide (A.3.39);
  other respiration inhibitors: diflumetorim (A.4.1); nitrophenyl derivates: binapacryl (A.4.2), dinobuton (A.4.3), dinocap (A.4.4), fluazinam (A.4.5), meptyldinocap (A.4.6), ferimzone (A.4.7); organometal compounds: fentin salts, e.g. fentin-acetate (A.4.8), fentin chloride (A.4.9) or fentin hydroxide (A.4.10); ametoctradin (A.4.11); silthiofam (A.4.12);

B) Sterol Biosynthesis Inhibitors (SBI Fungicides)
C14 demethylase inhibitors: triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), ipfentrifluconazole, (B.1.37), mefentrifluconazole (B.1.38), 2-(chloromethyl)-2-methyl-5-(p-tolylmethyl)-1 (1,2,4-triazol-1-ylmethyl)cyclopentanol (B.1.43); imidazoles: imazalil (B.1.44), pefurazoate (B.1.45), prochloraz (B.1.46), triflumizol (B.1.47); pyrimidines, pyridines and piperazines: fenarimol (B.1.49), pyrifenox (B.1.50), triforine (B.1.51), [3-(4-chloro-2-fluoro-phenyl)-5-(2,4-difluorophenyl)isoxazol-4-yl]-(3-pyridyl) methanol (B.1.52);
Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

Other Sterol biosynthesis inhibitors: chlorphenomizole (B.4.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (C.1.5), ofurace (C.1.6), oxadixyl (C.1.7);

other nucleic acid synthesis inhibitors: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4 amine (C.2.6), 5-fluoro-2-(4-fluorophenylmethoxy)pyrimidin-4 amine (C.2.7), 5-fluoro-2 (4 chlorophenylmethoxy)pyrimidin-4 amine (C.2.8);

D) Inhibitors of Cell Division and Cytoskeleton tubulin inhibitors: benomyl (D.1.1), carbendazim (D.1.2), fuberidazole (D1.3), thiabendazole (D.1.4), thiophanate-methyl (D.1.5), 3-chloro-4-(2,6-difluorophenyl)-6-methyl-5-phenyl-pyridazine (D.1.6), 3-chloro-6-methyl-5-phenyl-4-(2,4,6-trifluorophenyl)pyridazine (D.1.7), N ethyl-2-[(3-ethynyl-8-methyl-6-quinolyl) oxy]butanamide (D.1.8), N-ethyl-2-[(3-ethynyl-8 methyl-6 quinolyl)oxy]-2-methylsulfanyl-acetamide (D.1.9), 2-[(3-ethynyl-8-methyl-6-quinolyl)oxy]-N (2-fluoroethyl)butanamide (D.1.10), 2-[(3-ethynyl-8-methyl-6-quinolyl)oxy]-N-(2-flu-oroethyl)-2-methoxy-acetamide (D.1.11), 2-[(3-ethynyl-8-methyl-6-quinolyl)oxy]-N-propyl-butanamide (D.1.12), 2-[(3-ethynyl-8-methyl-6-quinolyl)oxy]-2-methoxy-N-propyl-acetamide (D.1.13), 2-[(3-ethynyl-8-methyl-6-quinolyl)oxy]-2-methylsulfanyl-N-propyl-acetamide (D. 1.14), 2 [(3 ethynyl-8-methyl-6-quinolyl)oxy]-N-(2-fluoroethyl)-2-methylsulfanyl-acetamide (D.1.15), 4-(2-bromo-4-fluoro-phenyl)-N-(2-chloro-6-fluoro-phenyl)-2,5-dimethyl-pyrazol-3 amine (D.1.16);

other cell division inhibitors: diethofencarb (D.2.1), ethaboxam (D.2.2), pencycuron (D.2.3), fluopicolide (D.2.4), zoxamide (D.2.5), metrafenone (D.2.6), pyriofenone (D.2.7);

E) Inhibitors of Amino Acid and Protein Synthesis methionine synthesis inhibitors: cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6);

F) Signal Transduction Inhibitors

MAP/histidine kinase inhibitors: fluoroimid (F.1.1), iprodione (F.1.2), procymidone (F.1.3), vinclozolin (F.1.4), fludioxonil (F.1.5);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7);

compounds affecting cell membrane permeability and fatty acids: propamocarb (G.4.1);

inhibitors of oxysterol binding protein: oxathiapiprolin (G.5.1), 2-{3-[2-(1-{[3,5-bis(difluoro-methyl-1H-pyrazol-1-yl]acetyl}piperidin-4-yl)-1,3-thiazol-4-yl]-4,5-dihydro-1,2 oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5 yl}-3-chlorophenyl methanesulfonate (G.5.3), 4-[1-[2-[3-(difluoromethyl)-5-methyl-pyrazol-1-yl]acetyl]-4-piperidyl]-N-tetralin-1-yl-pyridine-2-carboxamide (G.5.4), 4-[1-[2-[3,5-bis(difluoromethyl)pyrazol-1-yl]acetyl]-4-piperidyl]-N-tetralin-1-yl-pyridine-2-carboxamide (G.5.5), 4-[1-[2-[3-(difluoromethyl)-5-(trifluoromethyl)pyrazol-1-yl]acetyl]-4-piperidyl]-N-tetralin-1-yl-pyridine-2-carboxamide (G.5.6), 4-[1-[2-[5-cyclopropyl-3-(difluoromethyl)pyrazol-1-yl]acetyl]-4-piperidyl]-N-tetralin-1-yl-pyridine-2-carboxamide (G.5.7), 4-[1-[2-[5-methyl-3-(trifluoromethyl)pyrazol-1-yl]acetyl]-4-piperidyl]-N-tetralin-1-yl-pyridine-2-carboxamide (G.5.8), 4-[1-[2-[5-(difluoromethyl)-3-(trifluoromethyl)pyrazol-1-yl]acetyl]-4-piperidyl]-N-tetralin-1-yl-pyridine-2-carboxamide (G.5.9), 4 [1 [2-[3,5-bis(trifluoromethyl)pyrazol-1-yl]acetyl]-4-piperidyl]-N-tetralin-1-yl-pyridine-2-carboxamide (G.5.10), (4-[1-[2-[5-cyclopropyl-3-(trifluoromethyl)pyrazol-1-yl] acetyl]-4-piperidyl]-N-tetralin-1-yl-pyridine-2-carboxamide (G.5.11);

H) Inhibitors with Multi Site Action inorganic active substances: Bordeaux mixture (H.1.1), copper (H.1.2), copper acetate (H.1.3), copper hydroxide (H.1.4), copper oxychloride (H.1.5), basic copper sulfate (H.1.6), sulfur (H.1.7);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds: anilazine (H.3.1), chlorothalonil (H.3.2), captafol (H.3.3), cap-tan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (1.1.1), polyoxin B (1.1.2);

melanin synthesis inhibitors: pyroquilon (1.2.1), tricyclazole (1.2.2), carpropamid (1.2.3), dicyclomet (1.2.4), fenoxanil (1.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), calcium phosphonate (J.1.11), potassium phosphonate (J.1.12), potassium or sodium bicarbonate (J.1.9), 4 cyclopropyl-N-(2,4-dimethoxyphenyl)thiadiazole-5-carboxamide (J.1.10);

K) Unknown Mode of Action bronopol (K.1.1), chinomethionat (K.1.2), cyflufenamid (K.1.3), cymoxanil (K.1.4), dazomet (K.1.5), debacarb (K.1.6), diclocymet (K.1.7), diclomezine (K.1.8), difenzoquat (K.1.9), difenzoquat-methylsulfate (K.1.10), diphenylamin (K.1.11), fenitropan (K.1.12), fenpyrazamine (K.1.13), flumetover (K.1.14), flusulfamide (K.1.15), flutianil (K.1.16), harpin (K.1.17), methasulfocarb (K.1.18), nitrapyrin (K.1.19), nitrothal-isopropyl (K.1.20), tolprocarb (K.1.21), oxincopper (K.1.22), proquinazid (K.1.23), tebufloquin (K.1.24), tecloftalam (K.1.25), triazoxide (K.1.26), N'-(4-(4-chloro-3-trifluoromethyl-phenoxy)-2,5-dimethyl-phenyl)-N-ethyl-N methyl formamidine (K.1.27), N' (4-(4-fluoro-3-trifluoromethyl-phenoxy)-2,5-dimethyl-phenyl)-N-ethyl-N-methyl formamidine (K.1.28), N'-[4-[[3-[(4-chlorophenyl)methyl]-1,2,4-thiadiazol-5-yl]oxy]-2,5-dimethyl-phenyl]-N-ethyl-N-methyl-formamidine (K.1.29), N'-(5-bromo-6-indan-2-yloxy-2-methyl-3-pyridyl)-N-ethyl-N-methyl-formamidine (K.1.30), N'-[5-bromo-6-[1-(3,5-difluorophenyl)ethoxy]-2-methyl-3-pyridyl]-N-ethyl-N-methyl-formamidine (K.1.31), N'-[5-bromo-6-(4-isopropylcyclohexoxy)-2-methyl-3-pyridyl]-N-ethyl-N-methyl-formamidine (K.1.32), N' [5 bromo-2-methyl-6-(1-phenylethoxy)-3-pyridyl]-N-ethyl-N-methyl-formamidine (K.1.33), N'-(2-methyl-5-trifluoromethyl-4-(3-trimethylsilanyl-propoxy)-phenyl)-N-ethyl-N-methyl formamidine (K.1.34), N'-(5-difluoromethyl-2 methyl-4-(3-trimethylsilanyl-propoxy)-phenyl)-N-ethyl-N-methyl formamidine (K, 1.35), 2-(4-chloro-phenyl)-N-[4-(3,4-dimethoxy-phenyl)-isoxazol-5 yl]-2-prop-2-ynyloxy-acetamide (K.1.36), 3 [5-(4-chloro-phenyl)-2,3-dimethyl-isoxazolidin-3-yl]-pyridine (pyrisoxazole) (K.1.37), 3-[5-(4-methylphenyl)-2,3-dimethyl-isoxazolidin-3 yl]-pyridine (K.1.38), 5-chloro-1 (4,6-dimethoxy-pyrimidin-2-yl)-2-methyl-1H-benzoimidazole (K.1.39), ethyl (Z) 3 amino-2-cyano-3-phenyl-prop-2-enoate (K, 1.40), picarbutrazox (K.1.41), pentyl N-[6-[[(Z)-[(1-methyltetrazol-5-yl)-phenyl-methylene]amino]oxymethyl]-2-pyridyl]carbamate (K, 1.42), but-3-ynyl N-[6-[[(Z)-[(1-methyltetrazol-5-yl)-phenyl-methylene]amino]oxymethyl]-2-pyridyl]carbamate (K.1.43), 2-[2-[(7,8-difluoro-2-methyl-3-quinolyl)oxy]-6-fluoro-phenyl]propan-2-ol (K.1.44), 2-[2-fluoro-6-[(8-fluoro-2-methyl-3-quinolyl)oxy]phen-yl]propan-2-ol (K.1.45), quinofumelin (K.1.47), 9-fluoro-2,2-dimethyl-5-(3-quinolyl)-3H 1,4 benzoxazepine (K.1.49), 2-(6-benzyl-2-pyridyl)quinazoline (K.1.50), 2-[6-(3-fluoro-4 methoxy-phenyl)-5-methyl-2-pyridyl]quinazoline (K.1.51), dichlobentiazox (K.1.52), N'-(2,5-dimethyl-4-phenoxy-phenyl)-N-ethyl-N-methyl-formamidine (K.1.53).

The fungicides described by common names, their preparation and their activity e.g. against harmful fungi is known (cf.: http://www.alanwood.net/pesticides/); these substances are commercially available.

The fungicides described by IUPAC nomenclature, their preparation and their pesticidal activity is also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 10/139271, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833), CN 1907024, CN 1456054, CN 103387541, CN 1309897, WO 12/84812, CN 1907024, WO 09094442, WO 14/60177, WO 13/116251, WO 08/013622, WO 15/65922, WO 94/01546, EP 2865265, WO 07/129454, WO 12/165511, WO 11/081174, WO 13/47441).

Biopesticides

Suitable mixing partners for the compounds of the present invention also include biopesticides.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classified as microbial pesticides, even though they are multicellular.

(2) Biochemical pesticides are naturally occurring substances or structurally-similar and functionally identical to a naturally-occurring substance and extracts from biological sources that control pests or provide other crop protection uses as defined below, but have non-toxic mode of actions (such as growth or developmental regulation, attractants, repellents or defence activators (e.g. induced resistance) and are relatively non-toxic to mammals.

Biopesticides for use against crop diseases have already established themselves on a variety of crops. For example, biopesticides already play an important role in controlling downy mildew diseases. Their benefits include: a 0-Day Pre-Harvest Interval, the ability to use under moderate to severe disease pressure, and the ability to use in mixture or in a rotational program with other registered pesticides.

A major growth area for biopesticides is in the area of seed treatments and soil amendments. Biopesticidal seed treatments are e.g. used to control soil borne fungal pathogens that cause seed rots, damping-off, root rot and seedling blights. They can also be used to control internal seed borne fungal pathogens as well as fungal pathogens that are on the surface of the seed. Many biopesticidal products also show capacities to stimulate plant host defenses and other physiological processes that can make treated crops more resistant to a variety of biotic and abiotic stresses or can regulate plant growth. Many biopesticidal products also show capacities to stimulate plant health, plant growth and/or yield enhancing activity.

The following list of biopesticides, in conjunction with which the compounds of the present invention can be used, is intended to illustrate the possible combinations but does not limit them:

L) Biopesticides

L1) Microbial pesticides with fungicidal, bactericidal, viricidal and/or plant defense activator activity: *Ampelomyces quisqualis, Aspergillus flavus, Aureobasidium pullulans, Bacillus altitudinis, B. amyloliquefaciens, B. megaterium, B. mojavensis, B. mycoides, B. pumilus, B. simplex, B. solisalsi, B. subtilis, B. subtilis* var. *amyloliquefaciens, Candida oleo-*

*phila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea f. catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus alvei, Paenibacillus polymyxa, Pantoea vagans, Penicillium bilaiae, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperelloides, T. asperellum, T. atroviride, T. fertile, T. gamsii, T. harmatum, T. harzianum, T. polysporum, T. stromaticum, T. virens, T. viride, Typhula phacorrhiza, Ulocladium oudemansii, Verticillium dahlia*, zucchini yellow mosaic virus (avirulent strain);

L2) Biochemical pesticides with fungicidal, bactericidal, viricidal and/or plant defense activator activity: harpin protein, *Reynoutria sachalinensis* extract;

L3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai*, B. t. ssp. *israelensis*, B. t. ssp. *galleriae*, B. t. ssp. *kurstaki*, B. t. ssp. *tenebrionis*, *Beauveria bassiana, B. brongniartii, Burkholderia* spp., *Chromobacterium subtsugae, Cydia pomonella* granulovirus (CpGV), *Cryptophlebia leucotreta* granulovirus (CrleGV), *Flavobacterium* spp., *Helicoverpa armigera* nucleopolyhedrovirus (HearNPV), *Helicoverpa zea* nucleopolyhedrovirus (HzNPV), *Helicoverpa zea* single capsid nucleopolyhedrovirus (HzSNPV), *Heterorhabditis bacteriophora, Isaria fumosorosea, Lecanicillium longisporum, L. muscarium, Metarhizium anisopliae, Metarhizium anisopliae* var. *anisopliae, M. anisopliae* var. *acridum, Nomuraea rileyi, Paecilomyces fumosoroseus, P. lilacinus, Paenibacillus popilliae, Pasteuria* spp., *P. nishizawae, P. penetrans, P. ramosa, P. thornea, P. usgae, Pseudomonas fluorescens, Spodoptera littoralis* nucleopolyhedrovirus (SpliNPV), *Steinernema carpocapsae, S. feltiae, S. kraussei, Streptomyces galbus, S. microflavus;*

L4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, extract of *Chenopodium ambrosiodes*, Neem oil, Quillay extract;

L5) Microbial pesticides with plant stress reducing, plant growth regulator, plant growth promoting and/or yield enhancing activity: *Azospirillum amazonense, A. brasilense, A. lipoferum, A. irakense, A. halopraeferens, Bradyrhizobium* spp., *B. elkanii, B. japonicum, B. liaoningense, B. lupini, Delftia acidovorans, Glomus intraradices, Mesorhizobium* spp., *Rhizobium leguminosarum* bv. *phaseoli*, R. I. bv. *trifolii*, R. I. bv. *viciae, R. tropici, Sinorhizobium meliloti.*

The biopesticides from group L1) and/or L2) may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group L5) may also have fungicidal, bactericidal, viricidal, plant defense activator, insecticidal, acaricidal, molluscidal, pheromone and/or nematicidal activity.

Many of these biopesticides have been deposited under deposition numbers mentioned herein (the prefaces such as ATCC or DSM refer to the acronym of the respective culture collection, for details see e.g. here: http://www.wfcc.info/ccinfo/collection/by_acronym/), are referred to in literature, registered and/or are commercially available: mixtures of *Aureobasidium pullulans* DSM 14940 and DSM 14941 isolated in 1989 in Konstanz, Germany (e.g. blastospores in BlossomProtect® from bio-ferm GmbH, Austria), *Azospirillum brasilense* Sp245 originally isolated in wheat reagion of South Brazil (Passo Fundo) at least prior to 1980 (BR 11005; e.g. GELFIX® Gramineas from BASF Agricultural Specialties Ltd., Brazil), *A. brasilense* strains Ab-V5 and Ab-V6 (e.g. in AzoMax from Novozymes BioAg Produtos papra Agricultura Ltda., Quattro Barras, Brazil or Simbiose-Maiz® from Simbiose-Agro, Brazil; Plant Soil 331, 413-425, 2010), *Bacillus amyloliquefaciens* strain AP-188 (NRRL B-50615 and B-50331; U.S. Pat. No. 8,445,255); *B. amyloliquefaciens* spp. *plantarum* D747 isolated from air in Kikugawa-shi, Japan (US 20130236522 A1; FERM BP-8234; e.g. Double Nickel™ 55 WDG from Certis LLC, USA), *B. amyloliquefaciens* spp. *plantarum* FZB24 isolated from soil in Brandenburg, Germany (also called SB3615; DSM 96-2; J. Plant Dis. Prot. 105, 181-197, 1998; e.g. Taegro® from Novozyme Biologicals, Inc., USA), *B. amyloliquefaciens* ssp. *plantarum* FZB42 isolated from soil in Brandenburg, Germany (DSM 23117; J. Plant Dis. Prot. 105, 181-197, 1998; e.g. RhizoVital® 42 from AbiTEP GmbH, Germany), *B. amyloliquefaciens* ssp. *plantarum* MB1600 isolated from *faba* bean in Sutton Bonington, Nottinghamshire, U.K. at least before 1988 (also called 1430; NRRL B-50595; US 2012/0149571 A1; e.g. Integral® from BASF Corp., USA), *B. amyloliquefaciens* spp. *plantarum* QST-713 isolated from peach orchard in 1995 in California, U.S.A. (NRRL B-21661; e.g. Serenade® MAX from Bayer Crop Science LP, USA), *B. amyloliquefaciens* spp. *plantarum* TJ1000 isolated in 1992 in South Dakoda, U.S.A. (also called 1BE; ATCC BAA-390; CA 2471555 A1; e.g. QuickRoots™ from TJ Technologies, Watertown, S. Dak., USA), *B. firmus* CNCM I-1582, a variant of parental strain EIP-N1 (CNCM 1-1556) isolated from soil of central plain area of Israel (WO 2009/126473, U.S. Pat. No. 6,406, 690; e.g. Votivo® from Bayer CropScience LP, USA), *B. pumilus* GHA 180 isolated from apple tree rhizosphere in Mexico (IDAC 260707-01; e.g. PRO-MIX® BX from Premier Horticulture, Quebec, Canada), *B. pumilus* INR-7 otherwise referred to as BU-F22 and BU-F33 isolated at least before 1993 from cucumber infested by *Erwinia tracheiphila* (NRRL B-50185, NRRL B-50153; U.S. Pat. No. 8,445,255), *B. pumilus* KFP9F isolated from the rhizosphere of grasses in South Africa at least before 2008 (NRRL B-50754; WO 2014/029697; e.g. BAC-UP or FUSION-P from BASF Agricultural Specialities (Pty) Ltd., South Africa), *B. pumilus* QST 2808 was isolated from soil collected in Pohnpei, Federated States of Micronesia, in 1998 (NRRL B-30087; e.g. Sonata® or Ballad® Plus from Bayer Crop Science LP, USA), *B. simplex* ABU 288 (NRRL B-50304; U.S. Pat. No. 8,445,255), *B. subtilis* FB17 also called UD 1022 or UD10-22 isolated from red beet roots in North America (ATCC PTA-11857; System. Appl. Microbiol. 27, 372-379, 2004; US 2010/0260735; WO 2011/109395); *B. thuringiensis* ssp. *aizawai* ABTS-1857 isolated from soil taken from a lawn in Ephraim, Wis., U.S.A., in 1987 (also called ABG-6346; ATCC SD-1372; e.g. XenTari® from BioFa AG, Münsingen, Germany), B. t. ssp. *kurstaki* ABTS-351 identical to HD-1 isolated in 1967 from diseased Pink Bollworm black larvae in Brownsville, Tex., U.S.A. (ATCC SD-1275; e.g. Dipel® DF from Valent BioSciences, IL, USA), B. t. ssp. *kurstaki* SB4 isolated from *E. saccharina* larval cadavers (NRRL B-50753; e. g. Beta Pro® from BASF Agricultural Specialities (Pty) Ltd., South Africa), B. t. ssp. *tenebrionis* NB-176-1, a mutant of strain NB-125, a wild type strain isolated in 1982 from a dead pupa of the beetle *Tenebrio molitor* (DSM 5480; EP 585 215 B1; e.g. Novodor® from Valent BioSciences, Switzerland), *Beauveria bassiana* GHA (ATCC 74250; e.g. BotaniGard® 22WGP from Laverlam Int. Corp., USA), *B. bassiana* JW-1 (ATCC 74040; e.g. Naturalis® from CBC (Europe) S.r.l., Italy), *B. bassiana* PPRI 5339 isolated from the larva of the tortoise beetle *Conchyloctenia punctata* (NRRL 50757; e.g. BroadBand® from BASF Agricultural Specialities (Pty) Ltd., South Africa), *Bradyrhizobium elkanii* strains SEMIA 5019 (also called 29W) isolated in Rio de Janeiro, Brazil and SEMIA 587 isolated in 1967 in the State of Rio Grande do Sul, from an area previously inoculated with a North American isolate, and used in commercial inoculants since 1968 (Appl. Environ. Microbiol. 73(8), 2635, 2007; e.g. GELFIX 5 from BASF Agricultural Specialties Ltd., Brazil), *B. japonicum* 532c isolated from Wisconsin field in U.S.A. (Nitragin 61A152; Can. J. Plant. Sci. 70, 661-666, 1990; e.g. in Rhizoflo®, Histick®, Hicoat® Super from BASF Agricultural Specialties Ltd., Canada), *B. japonicum* E-109 variant of strain USDA 138 (INTA E109, SEMIA 5085; Eur. J. Soil Biol. 45, 28-35, 2009; Biol. Fertil. Soils 47, 81-89, 2011); *B. japonicum* strains deposited at SEMIA known from Appl. Environ. Microbiol. 73(8), 2635, 2007: SEMIA 5079 isolated from soil in Cerrados region, Brazil by Embrapa-Cerrados used in commercial inoculants since 1992 (CPAC 15; e.g. GELFIX 5 or ADHERE 60 from BASF Agricultural Specialties Ltd., Brazil), *B. japonicum* SEMIA 5080 obtained under lab conditions by Embrapa-Cerrados in Brazil and used in commercial inoculants since 1992, being a natural variant of SEMIA 586 (CB1809) originally isolated in U.S.A. (CPAC 7; e.g. GELFIX 5 or ADHERE 60 from BASF Agricultural Specialties Ltd., Brazil); *Burkholderia* sp. A396 isolated from soil in Nikko, Japan, in 2008 (NRRL B-50319; WO 2013/032693; Marrone Bio Innovations, Inc., USA), *Coniothyrium minitans* CON/M/91-08 isolated from oilseed rape (WO 1996/021358; DSM 9660; e.g. Contans® WG, Intercept® WG from Bayer CropScience AG, Germany), harpin (alpha-beta) protein (Science 257, 85-88, 1992; e.g. Messenger™ or HARP-N-Tek from Plant Health Care plc, U.K.), *Helicoverpa armigera* nucleopolyhedrovirus (HearNPV) (J. Invertebrate Pathol. 107, 112-126, 2011; e.g. Helicovex® from Adermatt Biocontrol, Switzerland; Diplomata® from Koppert, Brazil; Vivus® Max from AgBiTech Pty Ltd., Queensland, Australia), *Helicoverpa zea* single capsid nucleopolyhedrovirus (HzSNPV) (e.g. Gemstar® from Certis LLC, USA), *Helicoverpa zea* nucleopolyhedrovirus ABA-NPV-U (e.g. Heligen® from AgBiTech Pty Ltd., Queensland, Australia), *Heterorhabditis bacteriophora* (e.g. Nemasys® G from BASF Agricultural Specialities Limited, UK), *Isaria fumosorosea* Apopka-97 isolated from mealy bug on gynura in Apopka, Fla., U.S.A. (ATCC 20874; Biocontrol Science Technol. 22(7), 747-761, 2012; e.g. PFR-97™ or PreFeRal® from Certis LLC, USA), *Metarhizium anisopliae* var. *anisopliae* F52 also called 275 or V275 isolated from codling moth in Austria (DSM 3884, ATCC 90448; e.g. Met52® Novozymes Biologicals BioAg Group, Canada), *Metschnikowia fructicola* 277 isolated from grapes in the central part of Israel (U.S. Pat. No. 6,994,849; NRRL Y-30752; e.g. formerly Shemer® from Agrogreen, Israel), *Paecilomyces ilacinus* 251 isolated from infected nematode eggs in the Philippines (AGAL 89/030550; WO1991/02051; Crop Protection 27, 352-361, 2008; e.g. BioAct® from Bayer CropScience AG, Germany and MeloCon® from Certis, USA), *Paenibacillus alvei* NAS6G6 isolated from the rhizosphere of grasses in South Africa at least before 2008 (WO 2014/029697; NRRL B-50755; e.g. BAC-UP from BASF Agricultural Specialities (Pty) Ltd., South Africa), Pasteuria nishizawae Pn1 isolated from a soybean field in the mid-2000s in Illinois, U.S.A. (ATCC SD-5833; Federal Register 76(22), 5808, Feb. 2, 2011; e.g. Clariva™ PN from Syngenta Crop Protection, LLC, USA), *Penicillium bilaiae* (also called *P. bilaii*) strains ATCC 18309 (=ATCC 74319), ATCC 20851 and/or ATCC 22348 (=ATCC 74318) originally isolated from soil in Alberta, Canada (Fertilizer Res. 39, 97-103, 1994; Can. J. Plant Sci. 78(1), 91-102, 1998; U.S. Pat. No. 5,026,417, WO 1995/017806; e.g. Jump Start®, Provide® from Novozymes Biologicals BioAg Group, Canada), *Reynoutria sachalinensis* extract (EP 0307510 B1; e.g. Regalia® SC from Marrone BioInnovations, Davis, Calif., USA or Milsana® from BioFa AG, Germany), *Steinernema carpocapsae* (e.g. Millenium® from BASF Agricultural Specialities Limited, UK), *S. feltiae* (e.g. Nemashield® from BioWorks, Inc., USA; Nemasys® from BASF Agricultural Specialities Limited, UK), *Streptomyces microflavus* NRRL B-50550 (WO 2014/124369; Bayer CropScience, Germany), *Trichoderma asperelloides* JM41R isolated in South Africa (NRRL 50759; also referred to as *T. fertile*; e.g. Trichoplus® from BASF Agricultural Specialities (Pty) Ltd., South Africa), *T. harzianum* T-22 also called KRL-AG2 (ATCC 20847; BioControl 57, 687-696, 2012; e.g. Plantshield® from BioWorks Inc., USA or SabrEx™ from Advanced Biological Marketing Inc., Van Wert, Ohio, USA).

According to the invention, the solid material (dry matter) of the biopesticides (with the exception of oils such as Neem oil) are considered as active components (e.g. to be obtained after drying or evaporation of the extraction or suspension medium in case of liquid formulations of the microbial pesticides).

In accordance with the present invention, the weight ratios and percentages used herein for a biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1\times10^{10}$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, such as *Steinernema feltiae*.

When mixtures comprising microbial pesticides are employed in crop protection, the application rates preferably range from about $1\times10^6$ to $5\times10^{15}$ (or more) CFU/ha, preferably from about $1\times10^8$ to about $1\times10^{13}$ CFU/ha, and even more preferably from about $1\times10^9$ to about $1\times10^{12}$ CFU/ha.

In the case of (entomopathogenic) nematodes as microbial pesticides (e.g. *Steinernema feltiae*), the application rates preferably range inform about $1\times10^5$ to $1\times10^{12}$ (or more), more preferably from $1\times10^8$ to $1\times10^{11}$, even more preferably from $5\times10^8$ to $1\times10^{10}$ individuals (e.g. in the form of eggs, juvenile or any other live stages, preferably in an infective juvenile stage) per ha.

When mixtures comprising microbial pesticides are employed in seed treatment, the application rates with respect to plant propagation material preferably range from about $1\times10^6$ to $1\times10^{12}$ (or more) CFU/seed. Preferably, the concentration is about $1\times10^6$ to about $1\times10^9$ CFU/seed. In the case of the microbial pesticides II, the application rates with respect to plant propagation material also preferably range from about $1\times10^7$ to $1\times10^{14}$ (or more) CFU per 100 kg of seed, preferably from $1\times10^9$ to about $1\times10^{12}$ CFU per 100 kg of seed.

The invention also relates to agrochemical compositions comprising an auxiliary and at least one compound of the present invention or a mixture thereof.

An agrochemical composition comprises a pesticidally effective amount of a compound of the present invention or a mixture thereof. The term "pesticidally effective amount" is defined below.

The compounds of the present invention or the mixtures thereof can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Mono-graph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, lime-stone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl-sulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of the present invention on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible Concentrates (DC)

5-25 wt % of a compound I according to the invention and 1-10 wt % dispersant (e.g. polyvinylpyrrolidone) are dissolved in up to 100 wt % organic solvent (e.g. cyclohexanone). Dilution with water gives a dispersion.

iii) Emulsifiable Concentrates (EC)

15-70 wt % of a compound I according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)

5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I according to the invention are ground finely with addition of up to 100 wt % dispersants and wetting agents (e.g. sodium lignosulfonate and alcohol ethoxylate) and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

ix) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.

x) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsule. The monomers amount to 1-10 wt %. The wt % relate to the total CS composition.

xi) Dustable Powders (DP, DS)

1-10 wt % of a compound I according to the invention are ground finely and mixed intimately with up to 100 wt % solid carrier, e.g. finely divided kaolin.

xii) Granules (GR, FG)

0.5-30 wt % of a compound I according to the invention is ground finely and associated with up to 100 wt % solid carrier (e.g. silicate). Granulation is achieved by extrusion, spray-drying or the fluidized bed.

xiii) Ultra-Low Volume Liquids (UL)

1-50 wt % of a compound I according to the invention are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds of the present invention and/or mixing partners as defined above, may be mixed by the user in a spray tank and further auxiliaries and additives may be added, if appropriate.

In a further embodiment, either individual components of the composition according to the invention or partially premixed components, e.g. components comprising compounds of the present invention and/or mixing partners as defined above, can be applied jointly (e.g. after tank mix) or consecutively.

The compounds of the present invention are suitable for use in protecting crops, plants, plant propagation materials, such as seeds, or soil or water, in which the plants are growing, from attack or infestation by animal pests. Therefore, the present invention also relates to a plant protection method, which comprises contacting crops, plants, plant propagation materials, such as seeds, or soil or water, in which the plants are growing, to be protected from attack or infestation by animal pests, with a pesticidally effective amount of a compound of the present invention.

The compounds of the present invention are also suitable for use in combating or controlling animal pests. Therefore, the present invention also relates to a method of combating or controlling animal pests, which comprises contacting the animal pests, their habitat, breeding ground, or food supply, or the crops, plants, plant propagation materials, such as seeds, or soil, or the area, material or environment in which the animal pests are growing or may grow, with a pesticidally effective amount of a compound of the present invention.

The compounds of the present invention are effective through both contact and ingestion. Furthermore, the compounds of the present invention can be applied to any and all developmental stages, such as egg, larva, pupa, and adult.

The compounds of the present invention can be applied as such or in form of compositions comprising them as defined above. Furthermore, the compounds of the present invention can be applied together with a mixing partner as defined above or in form of compositions comprising said mixtures as defined above. The components of said mixture can be applied simultaneously, jointly or separately, or in succession, that is immediately one after another and thereby creating the mixture "in situ" on the desired location, e.g. the plant, the sequence, in the case of separate application, generally not having any effect on the result of the control measures.

The application can be carried out both before and after the infestation of the crops, plants, plant propagation materials, such as seeds, soil, or the area, material or environment by the pests.

Suitable application methods include inter alia soil treatment, seed treatment, in furrow application, and foliar application. Soil treatment methods include drenching the soil, drip irrigation (drip application onto the soil), dipping roots, tubers or bulbs, or soil injection. Seed treatment techniques include seed dressing, seed coating, seed dusting, seed soaking, and seed pelleting. In furrow applications typically include the steps of making a furrow in cultivated land, seeding the furrow with seeds, applying the pesticidally active compound to the furrow, and closing the furrow. Foliar application refers to the application of the pesticidally active compound to plant foliage, e.g. through spray equipment. For foliar applications, it can be advantageous to modify the behavior of the pests by use of pheromones in combination with the compounds of the present invention. Suitable pheromones for specific crops and pests are known to a skilled person and publicly available from databases of pheromones and semiochemicals, such as http://www.pherobase.com.

As used herein, the term "contacting" includes both direct contact (applying the compounds/compositions directly on the animal pest or plant—typically to the foliage, stem or roots of the plant) and indirect contact (applying the compounds/compositions to the locus, i.e. habitat, breeding ground, plant, seed, soil, area, material or environment in which a pest is growing or may grow, of the animal pest or plant).

The term "animal pest" includes arthropods, gastropods, and nematodes. Preferred animal pests according to the invention are arthropods, preferably insects and arachnids, in particular insects. Insects, which are of particular relevance for crops, are typically referred to as crop insect pests.

The term "crop" refers to both, growing and harvested crops.

The term "plant" includes cereals, e.g. durum and other wheat, rye, barley, triticale, oats, rice, or maize (fodder maize and sugar maize/sweet and field corn); beet, e.g. sugar beet or fodder beet; fruits, such as pomes, stone fruits or soft fruits, e.g. apples, pears, plums, peaches, nectarines, almonds, cherries, papayas, strawberries, raspberries, blackberries or gooseberries; leguminous plants, such as beans, lentils, peas, alfalfa or soybeans; oil plants, such as rapeseed (oilseed rape), turnip rape, mustard, olives, sunflowers, coconut, cocoa beans, castor oil plants, oil palms, ground nuts or soybeans; cucurbits, such as squashes, pumpkins, cucumber or melons; fiber plants, such as cotton, flax, hemp or jute; citrus fruit, such as oranges, lemons, grapefruits or mandarins; vegetables, such as eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, such as avocados, cinnamon or camphor; energy and raw material plants, such as corn, soybean, rapeseed, sugar cane or oil palm; tobacco; nuts, e.g. walnuts; pistachios; coffee; tea; bananas; vines (table grapes and grape juice grape vines); hop; sweet leaf (also called *Stevia*); natural rubber plants or ornamental and forestry plants, such as flowers (e.g. carnation, petunias, geranium/pelargoniums, pansies and impatiens), shrubs, broad-leaved trees (e.g. poplar) or evergreens, e.g. conifers; *eucalyptus*; turf; lawn; grass such as grass for animal feed or ornamental uses. Preferred plants include potatoes sugar beets, tobacco, wheat, rye, barley, oats, rice, corn, cotton, soybeans, rapeseed, legumes, sunflowers, coffee or sugar cane; fruits; vines; ornamentals; or vegetables, such as cucumbers, tomatoes, beans or squashes.

The term "plant" is to be understood as including wild type plants and plants, which have been modified by either conventional breeding, or mutagenesis or genetic engineering, or by a combination thereof, in order to provide a new trait to a plant or to modify an already present trait.

The term "plant" is to be understood as including wild type plants and plants, which have been modified by either conventional breeding, or mutagenesis or genetic engineering, or by a combination thereof. Plants, which have been modified by mutagenesis or genetic engineering, and are of particular commercial importance, include alfalfa, rapeseed (e.g. oilseed rape), bean, carnation, chicory, cotton, eggplant, *eucalyptus*, flax, lentil, maize, melon, *papaya, petunia*, plum, poplar, potato, rice, soybean, squash, sugar beet, sugarcane, sunflower, sweet pepper, tobacco, tomato, and cereals (e.g. wheat), in particular maize, soybean, cotton, wheat, and rice. In plants, which have been modified by mutagenesis or genetic engineering, one or more genes have been mutagenized or integrated into the genetic material of the plant. The one or more mutagenized or integrated genes are preferably selected from pat, epsps, cry1Ab, bar, cry1Fa2, cry1Ac, cry34Ab1, cry35AB1, cry3A, cryF, cry1F, mcry3a, cry2Ab2, cry3Bb1, cry1A.105, dfr, barnase, vip3Aa20, barstar, als, bxn, bp40, asn1, and ppo5. The mutagenesis or integration of the one or more genes is performed in order to improve certain properties of the plant. Such properties, also known as traits, include abiotic stress tolerance, altered growth/yield, disease resistance, herbicide tolerance, insect resistance, modified product quality, and pollination control. Of these properties, herbicide tolerance, e.g. imidazolinone tolerance, glyphosate tolerance, or glufosinate tolerance, is of particular importance. Several plants have been rendered tolerant to herbicides by mutagenesis, for example Clearfield® oilseed rape being tolerant to imidazolinones, e.g. imazamox. Alternatively, genetic engineering methods have been used to render plants, such as soybean, cotton, corn, beets and oil seed rape, tolerant to herbicides, such as glyphosate and glufosinate, some of which are commercially available under the trade names RoundupReady® (glyphosate) and LibertyLink® (glufosinate). Furthermore, insect resistance is of importance, in particular lepidopteran insect resistance and coleopteran insect resistance. Insect resistance is typically achieved by modifying plants by integrating cry and/or vip genes, which were isolated from *Bacillus thuringiensis* (Bt), and code for the respective Bt toxins. Genetically modified plants with insect resistance are commercially available under trade names including WideStrike®, Bollgard®, Agrisure®, Herculex®, YieldGard®, Genuity®, and Intacta®. Plants may be modified by mutagenesis or genetic engineering either in terms of one property (singular traits) or in terms of a combination of properties (stacked traits). Stacked traits, e.g. the combination of herbicide tolerance and insect resistance, are of increasing importance. In general, all relevant modified plants in connection with singular or stacked traits as well as detailed information as to the mutagenized or integrated genes and the respective events are available from websites of the organizations "International Service for the Acquisition of Agri-biotech Applications (ISAAA)" (http://www.isaaa.org/gmapprovaldatabase) and "Center for Environmental Risk Assessment (CERA)" (http://cera-gmc.org/GMCropDatabase).

It has surprisingly been found that the pesticidal activity of the compounds of the present invention may be enhanced by the insecticidal trait of a modified plant. Furthermore, it has been found that the compounds of the present invention are suitable for preventing insects to become resistant to the insecticidal trait or for combating pests, which already have become resistant to the insecticidal trait of a modified plant. Moreover, the compounds of the present invention are suitable for combating pests, against which the insecticidal trait is not effective, so that a complementary insecticidal activity can advantageously be used.

The term "plant propagation material" refers to all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "seed" embraces seeds and plant propagules of all kinds including but not limited to true seeds, seed pieces, suckers, corms, bulbs, fruit, tubers, grains, cuttings, cut shoots and the like, and means in a preferred embodiment true seeds.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment, in furrow application or of application to the pests dwelling place or nest, the quantity of active ingredient ranges from 0.0001 to 500 g per 100 m$^2$, preferably from 0.001 to 20 g per 100 m$^2$.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, 30 to 40 g per hectare, or 40 to 50 g per hectare.

The compounds of the invention are particularly suitable for use in the treatment of seeds in order to protect the seeds from insect pests, in particular from soil-living insect pests, and the resulting seedling's roots and shoots against soil pests and foliar insects. The invention therefore also relates to a method for the protection of seeds from insects, in particular from soil insects, and of the seedling's roots and shoots from insects, in particular from soil and foliar insects, said method comprising treating the seeds before sowing and/or after pregermination with a compound of the invention. The protection of the seedling's roots and shoots is preferred. More preferred is the protection of seedling's shoots from piercing and sucking insects, chewing insects and nematodes.

The term "seed treatment" comprises all suitable seed treatment techniques known in the art, such as seed dressing, seed coating, seed dusting, seed soaking, seed pelleting, and in-furrow application methods. Preferably, the seed treatment application of the active compound is carried out by spraying or by dusting the seeds before sowing of the plants and before emergence of the plants.

The invention also comprises seeds coated with or containing the active compound. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is for example seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment of seeds from plants, which have been modified by mutagenesis or genetic engineering, and which e.g. tolerate the action of herbicides or fungicides or insecticides. Such modified plants have been described in detail above.

Conventional seed treatment formulations include for example flowable concentrates FS, solutions LS, suspoemulsions (SE), powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. Preferably, the formulations are applied such that germination is not included.

The active substance concentrations in ready-to-use formulations, which may be obtained after two-to-tenfold dilution, are preferably from 0.01 to 60% by weight, more preferably from 0.1 to 40% by weight.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of the compounds of the invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

In the treatment of seed, the application rates of the compounds of the invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed, e.g. from 1 g to 100 g or from 5 g to 100 g per 100 kg of seed.

The invention therefore also relates to seed comprising a compound of the invention, or an agriculturally useful salt thereof, as defined herein. The amount of the compound of the invention or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

The compounds of the invention may also be used for improving the health of a plant. Therefore, the invention also relates to a method for improving plant health by treating a plant, plant propagation material and/or the locus where the plant is growing or is to grow with an effective and non-phytotoxic amount of a compound of the invention.

As used herein "an effective and non-phytotoxic amount" means that the compound is used in a quantity which allows to obtain the desired effect but which does not give rise to any phytotoxic symptom on the treated plant or on the plant grown from the treated propagule or treated soil.

The terms "plant" and "plant propagation material" are defined above.

"Plant health" is defined as a condition of the plant and/or its products which is determined by several aspects alone or in combination with each other such as yield (for example increased biomass and/or increased content of valuable ingredients), quality (for example improved content or composition of certain ingredients or shelf life), plant vigour (for example improved plant growth and/or greener leaves ("greening effect"), tolerance to abiotic (for example drought) and/or biotic stress (for example disease) and production efficiency (for example, harvesting efficiency, processability).

The above identified indicators for the health condition of a plant may be interdependent and may result from each other. Each indicator is defined in the art and can be determined by methods known to a skilled person.

The compounds of the invention are also suitable for use against non-crop insect pests. For use against said non-crop pests, compounds of the invention can be used as bait composition, gel, general insect spray, aerosol, as ultra-low volume application and bed net (impregnated or surface applied). Furthermore, drenching and rodding methods can be used.

As used herein, the term "non-crop insect pest" refers to pests, which are particularly relevant for non-crop targets, such as ants, termites, wasps, flies, ticks, mosquitos, crickets, or cockroaches.

The bait can be a liquid, a solid or a semisolid preparation (e.g. a gel). The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature (e.g. http://www.pherobase.com), and are known to those skilled in the art.

For use in bait compositions, the typical content of active ingredient is from 0.001 weight % to 15 weight %, desirably from 0.001 weight % to 5% weight % of active compound.

Formulations of the compounds of the invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents, furthermore auxiliaries such as emulsifiers, perfume oils, if appropriate stabilizers, and, if required, propellants.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder.

The compounds of the invention and its compositions can be used for protecting wooden materials such as trees, board fences, sleepers, frames, artistic artifacts, etc. and buildings, but also construction materials, furniture, leathers, fibers, vinyl articles, electric wires and cables etc. from ants and/or termites, and for controlling ants and termites from doing harm to crops or human being (e.g. when the pests invade into houses and public facilities).

Customary application rates in the protection of materials are, for example, from 0.001 g to 2000 g or from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

The compounds of the invention are especially suitable for efficiently combating animal pests such as arthropods, gastropods and nematodes including but not limited to: insects from the order of Lepidoptera, for example *Achroia grisella, Acleris* spp. such as *A. fimbriana, A. gloverana, A. variana; Acrolepiopsis assectella, Acronicta major, Adoxophyes* spp. such as *A. cyrtosema, A. orana; Aedia leucomelas, Agrotis* spp. such as *A. exclamationis, A. fucosa, A. ipsilon, A. orthogoma, A. segetum, A. subterranea; Alabama argillacea, Aleurodicus dispersus, Alsophila pometaria, Ampelophaga rubiginosa, Amyelois transitella, Anacampsis sarcitella, Anagasta kuehniella, Anarsia lineatella, Anisota senatoria, Antheraea pernyi, Anticarsia (=Thermesia)* spp. such as *A. gemmatalis; Apamea* spp., *Aproaerema modicella, Archips* spp. such as *A. argyrospila, A. fuscocupreanus, A. rosana, A. xyloseanus; Argyresthia conjugella, Argyroploce* spp., *Argyrotaenia* spp. such as *A. velutinana; Athetis mindara, Austroasca viridigrisea, Autographa gamma, Autographa nigrisigna, Barathra brassicae, Bedellia* spp., *Bonagota salubricola, Borbo cinnara, Bucculatrix thurberiella, Bupalus piniarius, Busseola* spp., *Cacoecia* spp. such as *C. murinana, C. podana; Cactoblastis cactorum, Cadra cautella, Calingo braziliensis, Caloptilis theivora, Capua reticulana, Carposina* spp. such as *C. niponensis, C. sasakii; Cephus* spp., *Chaetocnema aridula, Cheimatobia brumata, Chilo* spp. such as *C. Indicus, C. suppressalis, C. partellus; Choreutis pariana, Choristoneura* spp. such as *C. conflictana, C. fumiferana, C. longicellana, C. murinana, C. occidentalis, C. rosaceana; Chrysodeixis (=Pseudoplusia)* spp. such as *C. eriosoma, C. includens; Cirphis unipuncta, Clysia ambiguella, Cnaphalocerus* spp., *Cnaphalocrocis medinalis, Cnephasia* spp., *Cochylis hospes, Coleophora* spp., *Colias eurytheme, Conopomorpha* spp., *Conotrachelus* spp., *Copitarsia* spp., *Corcyra cephalonica, Crambus caliginosellus, Crambus teterrellus, Crocidosema (=Epinotia) aporema*, Cydalima *(=Diaphania) perspectalis, Cydia (=Carpocapsa)* spp. such as *C. pomonella, C. latiferreana; Dalaca noctuides, Datana integerrima, Dasychira pinicola, Dendrolimus* spp. such as *D. pini, D. spectabilis, D. sibiricus; Desmia funeralis, Diaphania* spp. such as *D. nitidalis, D. hyalinata; Diatraea grandiosella, Diatraea saccharalis, Diphthera festiva, Earias* spp. such as *E. insulana, E. vittella; Ecdytolopha aurantianu*, Egira (=Xylomyges) *curialis, Elasmopalpus lignosellus, Eldana saccharina, Endopiza viteana, Ennomos subsignaria, Eoreuma loftini, Ephestia* spp. such as *E. cautella, E. elutella, E. kuehniella; Epinotia aporema, Epiphyas postvittana, Erannis tiliaria, Erionota thrax, Etiella* spp., *Eulia* spp., *Eupoecilia ambiguella, Euproctis chrysorrhoea, Euxoa* spp., *Evetria bouliana, Faronta albilinea, Feltia* spp. such as *F. subterranean; Galleria mellonella, Gracillaria* spp., *Grapholita* spp. such as *G. funebrana, G. molesta, G. inopinata; Halysidota* spp., *Harrisina americana, Hedylepta* spp., *Helicoverpa* spp. such as *H. armigera (=Heliothis armigera), H. zea (=Heliothis zea); Heliothis* spp. such as *H. assulta, H. subflexa, H. virescens; Hellula* spp. such as *H. undalis, H. rogatalis; Helocoverpa gelotopoeon, Hemileuca oliviae, Herpetogramma licarsisalis, Hibernia defoliaria, Hofmannophila pseudospretella, Homoeosoma electellum, Homona magnanima, Hypena scabra, Hyphantria cunea, Hyponomeuta padella, Hyponomeuta malinellus, Kakivoria flavofasciata, Keiferia lycopersicella, Lambdina fiscellaria fiscellaria, Lambdina fiscellaria lugubrosa, Lamprosema indicata, Laspeyresia molesta, Leguminivora glycinivorella, Lerodea eufala, Leucinodes orbonalis, Leucoma salicis, Leucoptera* spp. such as *L. coffeella, L. scitella; Leuminivora lycinivorella, Lithocolletis blancardella, Lithophane antennata, Llattia octo (=Amyna axis), Lobesia botrana, Lophocampa* spp., *Loxagrotis albicosta, Loxostege* spp. such as *L. sticticalis, L. cereralis; Lymantria* spp. such as *L. dispar, L. monacha; Lyonetia clerkella, Lyonetia prunifoliella, Malacosoma* spp. such as *M. americanum, M. californicum, M. constrictum, M. neustria; Mamestra* spp. such as *M. brassicae, M. configurata; Mamstra brassicae, Manduca* spp. such as *M. quinquemaculata, M. sexta; Marasmia* spp, *Marmara* spp., *Maruca testulalis, Megalopyge lanata, Melanchra picta, Melanitis leda, Mocis* spp. such as *M. lapites, M. repanda; Mocis latipes, Monochroa fragariae, Mythimna separata, Nemapogon cloacella, Neoleucinodes elegantalis, Nepytia* spp., *Nymphula* spp., *Oiketicus* spp., *Omiodes indicata, Omphisa anastomosalis, Operophtera brumata, Orgyia pseudotsugata, Oria* spp., *Orthaga thyrisalis, Ostrinia* spp. such as *O. nubilalis; Oulema oryzae, Paleacrita vernata, Panolis flammea, Parnara* spp., *Papaipema nebris, Papilio*

*cresphontes, Paramyelois transitella, Paranthrene regalis, Paysandisia archon, Pectinophora* spp. such as *P. gossypiella; Peridroma saucia, Perileucoptera* spp., such as *P. coffeella; Phalera bucephala, Phryganidia californica, Phthorimaea* spp. such as *P. operculella; Phyllocnistis citrella, Phyllonorycter* spp. such as *P. blancardella, P. crataegella, P. issikii, P. ringoniella; Pieris* spp. such as *P. brassicae, P. rapae, P. napi; Pilocrocis tripunctata, Plathypena scabra, Platynota* spp. such as *P. flavedana, P. idaeusalis, P. stultana; Platyptilia carduidactyla, Plebejus argus, Plodia interpunctella, Plusia* spp, *Plutella maculipennis, Plutella xylostella, Pontia protodica, Prays* spp., *Prodenia* spp., *Proxenus lepigone, Pseudaletia* spp. such as *P. sequax, P. unipuncta; Pyrausta nubilalis, Rachiplusia nu, Richia albicosta, Rhizobius ventralis, Rhyacionia frustrana, Sabulodes aegrotata, Schizura concinna, Schoenobius* spp., *Schreckensteinia festaliella, Scirpophaga* spp. such as *S. incertulas, S. innotata; Scotia segetum, Sesamia* spp. such as *S. inferens, Seudyra subflava, Sitotroga cerealella, Sparganothis pilleriana, Spilonota lechriaspis, S. ocellana, Spodoptera* (=Lamphygma) spp. such as *S. cosmoides, S. eridania, S. exigua, S. frugiperda, S. latisfascia, S. littoralis, S. litura, S. ornithogalli; Stigmella* spp., *Stomopteryx subsecivella, Strymon bazochii, Sylepta derogata, Synanthedon* spp. such as *S. exitiosa, Tecia solanivora, Telehin licus, Thaumatopoea pityocampa, Thaumatotibia* (=Cryptophlebia) *leucotreta, Thaumetopoea pityocampa, Thecla* spp., *Theresimima ampelophaga, Thyrinteina* spp, *Tildenia inconspicuella, Tinea* spp. such as *T. cloacella, T. pellionella; Tineola bisselliella, Tortrix* spp. such as *T. viridana; Trichophaga tapetzella, Trichoplusia* spp. such as *T. ni; Tuta* (=Scrobipalpula) *absoluta, Udea* spp. such as *U. rubigalis, U. rubigalis; Virachola* spp., *Yponomeuta padella*, and *Zeiraphera canadensis;* insects from the order of Coleoptera, for example *Acalymma vittatum, Acanthoscehdes obtectus, Adoretus* spp., *Agelastica alni, Agrilus* spp. such as *A. anxius, A. planipennis, A. sinuatus; Agriotes* spp. such as *A. fuscicollis, A. lineatus, A. obscurus; Alphitobius diaperinus, Amphimallus solstitialis, Anisandrus dispar, Anisoplia austriaca, Anobium punctatum, Anomala corpulenta, Anomala rufocuprea, Anoplophora* spp. such as *A. glabripennis; Anthonomus* spp. such as *A. eugenii, A. grandis, A. pomorum; Anthrenus* spp., *Aphthona euphoridae, Apion* spp., *Apogonia* spp., *Athous haemorrhoidalis, Atomaria* spp. such as *A. linearis; Attagenus* spp., *Aulacophora femoralis, Blastophagus piniperda, Blitophaga undata, Bruchidius obtectus, Bruchus* spp. such as *B. lentis, B. pisorum, B. rufimanus; Byctiscus betulae, Callidiellum rufipenne, Callopistria floridensis, Callosobruchus chinensis, Cameraria ohridella, Cassida nebulosa, Cerotoma trifurcata, Cetonia aurata, Ceuthorhynchus* spp. such as *C. assimilis, C. napi; Chaetocnema tibialis, Cleonus mendicus, Conoderus* spp. such as *C. vespertinus; Conotrachelus nenuphar, Cosmopolites* spp., *Costelytra zealandica, Crioceris asparagi, Cryptolestes ferrugineus, Cryptorhynchus lapathi, Ctenicera* spp. such as *C. destructor; Curculio* spp., *Cylindrocopturus* spp., *Cyclocephala* spp., *Dactylispa balyi, Dectes texanus, Dermestes* spp., *Diabrotica* spp. such as *D. undecimpunctata, D. speciosa, D. longicornis, D. semipunctata, D. virgifera; Diaprepes abbreviates, Dichocrocis* spp., *Dicladispa armigera, Diloboderus abderus, Diocalandra frumenti* (*Diocalandra stigmaticollis*), *Enaphalodes rufulus, Epilachna* spp. such as *E. varivestis, E. vigintioctomaculata; Epitrix* spp. such as *E. hirtipennis, E. similaris; Eutheola humilis, Eutinobothrus brasiliensis, Faustinus cubae, Gibbium psylloides, Gnathocerus cornutus, Hellula undalis, Heteronychus arator, Hylamorpha elegans, Hylobius abietis, Hylotrupes bajulus, Hypera* spp. such as *H. brunneipennis, H. postica; Hypomeces squamosus, Hypothenemus* spp., *Ips typographus, Lachnosterna consanguinea, Lasioderma serricorne, Latheticus oryzae, Lathridius* spp., *Lema* spp. such as *L. bilineata, L. melanopus; Leptinotarsa* spp. such as *L. decemlineata; Leptispa pygmaea, Limonius californicus, Lissorhoptrus oryzophilus, Lixus* spp., *Luperodes* spp., *Lyctus* spp. such as *L. bruneus; Liogenys fuscus, Macrodactylus* spp. such as *M. subspinosus; Maladera matrida, Megaplatypus mutates, Megascelis* spp., *Melanotus communis, Meligethes* spp. such as *M. aeneus; Melolontha* spp. such as *M. hippocastani, M. melolontha; Metamasius hemipterus, Microthecha* spp., *Migdolus* spp. such as *M. fryanus, Monochamus* spp. such as *M. alternatus; Naupactus xanthographus, Niptus hololeucus, Oberia brevis, Oemona hirta, Oryctes rhinoceros, Oryzaephilus surinamensis, Oryzaphagus oryzae, Otiorrhynchus sulcatus, Otiorrhynchus ovatus, Otiorrhynchus sulcatus, Oulema melanopus, Oulema oryzae, Oxycetonia jucunda, Phaedon* spp. such as *P. brassicae, P. cochleariae; Phoracantha recurva, Phyllobius pyri, Phyllopertha horticola, Phyllophaga* spp. such as *P. helleri; Phyllotreta* spp. such as *P. chrysocephala, P. nemorum, P. striolata, P. vittula; Phyllopertha horticola, Popillia japonica, Premnotrypes* spp., *Psacothea hilaris, Psylliodes chrysocephala, Prostephanus truncates, Psylliodes* spp., *Ptinus* spp., *Pulga saltona, Rhizopertha dominica, Rhynchophorus* spp. such as *R. billineatus, R. ferrugineus, R. palmarum, R. phoenicis, R. vulneratus; Saperda candida, Scolytus schevyrewi, Scyphophorus acupunctatus, Sitona lineatus, Sitophilus* spp. such as *S. granaria, S. oryzae, S. zeamais; Sphenophorus* spp. such as *S. levis; Stegobium paniceum, Sternechus* spp. such as *S. subsignatus; Strophomorphus ctenotus, Symphyletes* spp., *Tanymecus* spp., *Tenebrio molitor, Tenebrioides mauretanicus, Tribolium* spp. such as *T. castaneum; Trogoderma* spp., *Tychius* spp., *Xylotrechus* spp. such as *X. pyrrhoderus*; and, *Zabrus* spp. such as *Z. tenebrioides;* insects from the order of Diptera e.g. *Aedes* spp. such as *A. aegypti, A. albopictus, A. vexans; Anastrepha ludens, Anopheles* spp. such as *A. albimanus, A. crucians, A. freeborni, A. gambiae, A. leucosphyrus, A. maculipennis, A. minimus, A. quadrimaculatus, A. sinensis; Bactrocera invadens, Bibio hortulanus, Calliphora erythrocephala, Calliphora vicina, Ceratitis capitata, Chrysomyia* spp. such as *C. bezziana, C. hominivorax, C. macellaria; Chrysops atlanticus, Chrysops discalis, Chrysops silacea, Cochliomyia* spp. such as *C. hominivorax; Contarinia* spp. such as *C. sorghicola; Cordylobia anthropophaga, Culex* spp. such as *C. nigripalpus, C. pipiens, C. quinquefasciatus, C. tarsalis, C. tritaeniorhynchus; Culicoides furens, Culiseta inornata, Culiseta melanura, Cuterebra* spp., *Dacus cucurbitae, Dacus oleae, Dasineura brassicae, Dasineura oxycoccana, Delia* spp. such as *D. antique, D. coarctata, D. platura, D. radicum; Dermatobia hominis, Drosophila* spp. such as *D. suzukii, Fannia* spp. such as *F. canicularis; Gastraphilus* spp. such as *G. intestinalis; Geomyza tipunctata, Glossina* spp. such as *G. fuscipes, G. morsitans, G. palpalis, G. tachinoides; Haematobia irritans, Haplodiplosis equestris, Hippelates* spp., *Hylemyia* spp. such as *H. platura; Hypoderma* spp. such as *H. lineata; Hyppobosca* spp., *Hydrellia philippina, Leptoconops torrens, Liriomyza* spp. such as *L. sativae, L. trifolii; Lucilia* spp. such as *L. caprina, L. cuprina, L. sericata; Lycoria pectoralis, Mansonia titillanus, Mayetiola* spp. such as *M. destructor; Musca* spp. such as *M. autumnalis, M. domestica; Muscina stabulans, Oestrus* spp. such as *O. ovis; Opomyza florum, Oscinella* spp. such as *O. frit; Orseolia oryzae, Pegomya hysocyami, Phlebotomus argentipes, Phorbia* spp. such as *P. antiqua, P. brassicae, P. coarctata; Phytomyza gymnostoma, Prosimulium mixtum, Psila rosae, Psorophora columbiae, Psorophora discolor, Rhagoletis* spp. such as *R. cerasi, R. cingulate, R. indifferens, R. mendax, R. pomonella; Rivellia quadrifasciata, Sarcophaga* spp. such as *S. haemorrhoidalis; Simulium vittatum, Sitodiplosis mosellana, Stomoxys* spp. such as *S. calcitrans; Tabanus* spp. such as *T. atratus, T. bovinus, T. lineola, T. similis; Tannia* spp., *Thecodiplosis japonensis, Tipula oleracea, Tipula paludosa*, and *Wohlfahrtia* spp;

insects from the order of Thysanoptera for example, *Baliothrips biformis, Dichromothrips corbetti, Dichromothrips* ssp., *Echinothrips americanus, Enneothrips flavens, Frankliniella* spp. such as *F. fusca, F. occidentalis, F. tritici; Heliothrips* spp., *Hercinothrips femoralis, Kakothrips* spp., *Microcephalothrips abdominalis, Neohydatothrips samayunkur, Pezothrips kellyanus, Rhipiphorothrips cruentatus, Scirtothrips* spp. such as *S. citri, S. dorsalis, S. perseae; Stenchaetothrips* spp, *Taeniothrips cardamoni, Taeniothrips inconsequens, Thrips* spp. such as *T. imagines, T. hawaiiensis, T. oryzae, T. palmi, T. parvispinus, T. tabaci;* insects from the order of Hemiptera for example, *Acizzia jamatonica, Acrosternum* spp. such as *A. hilare; Acyrthosipon* spp. such as *A. onobrychis, A. pisum; Adelges laricis, Adelges tsugae, Adelphocoris* spp., such as *A. rapidus, A. superbus; Aeneolamia* spp., *Agonoscena* spp., *Aulacorthum solani, Aleurocanthus woglumi, Aleurodes* spp., *Aleurodicus disperses, Aleurolobus barodensis, Aleurothrixus* spp., *Amrasca* spp., *Anasa tristis, Antestiopsis* spp., *Anuraphis cardui, Aonidiella* spp., *Aphanostigma piri, Aphidula nasturtii, Aphis* spp. such as *A. craccivora, A. fabae, A. forbesi, A. gossypii, A. grossulariae, A. maidiradicis, A. pomi, A. sambuci, A. schneideri, A. spiraecola; Arboridia apicalis, Arilus critatus, Aspidiella* spp., *Aspidiotus* spp., *Atanus* spp., *Aulacaspis yasumatsui, Aulacorthum solani, Bactericera cockerelli (Paratrioza cockerelli), Bemisia* spp. such as *B. argentifolii, B. tabaci (Aleurodes tabaci); Blissus* spp. such as *B. leucopterus; Brachycaudus* spp. such as *B. cardui, B. helichrysi, B. persicae, B. prunicola; Brachycolus* spp., *Brachycorynella asparagi, Brevicoryne brassicae, Cacopsylla* spp. such as *C. fulguralis, C. pyricola (Psylla piri); Calligypona marginata, Calocoris* spp., *Campylomma livida, Capitophorus horni, Carneocephala fulgida, Cavelerius* spp., *Ceraplastes* spp., *Ceratovacuna lanigera, Ceroplastes ceriferus, Cerosipha gossypii, Chaetosiphon fragaefolii, Chionaspis tegalensis, Chlorita onukii, Chromaphis juglandicola, Chrysomphalus ficus, Cicadulina mbila, Cimex* spp. such as *C. hemipterus, C. lectularius; Coccomytilus halli, Coccus* spp. such as *C. hesperidum, C. pseudomagnoliarum; Corythucha arcuata, Creontiades dilutus, Cryptomyzus ribis, Chrysomphalus aonidium, Cryptomyzus ribis, Ctenarytaina spatulata, Cyrtopeltis notatus, Dalbulus* spp., *Dasynus piperis, Dialeurodes* spp. such as *D. citrifolii; Dalbulus maidis, Diaphorina* spp. such as *D. citri; Diaspis* spp. such as *D. bromeliae; Dichelops furcatus, Diconocoris hewetti, Doralis* spp., *Dreyfusia nordmannianae, Dreyfusia piceae, Drosicha* spp., *Dysaphis* spp. such as *D. plantaginea, D. pyri, D. radicola; Dysaulacorthum pseudosolani, Dysdercus* spp. such as *D. cingulatus, D. intermedius; Dysmicoccus* spp., *Edessa* spp., *Geocoris* spp., *Empoasca* spp. such as *E. fabae, E. solana; Epidiaspis leperii, Eriosoma* spp. such as *E. lanigerum, E. pyricola; Erythroneura* spp., *Eurygaster* spp. such as *E. integriceps; Euscelis bilobatus, Euschistus* spp. such as *E. heros, E. impictiventris, E. servus; Fiorinia theae, Geococcus coffeae, Glycaspis brimblecombei, Halyomorpha* spp. such as *H. halys; Heliopeltis* spp., *Homalodisca vitripennis (=H. coagulata), Horcias nobilellus, Hyalopterus pruni, Hyperomyzus lactucae, Icerya* spp. such as *I. purchase; Idiocerus* spp., *Idioscopus* spp., *Laodelphax striatellus, Lecanium* spp., *Lecanoideus floccissimus, Lepidosaphes* spp. such as *L. ulmi; Leptocorisa* spp., *Leptoglossus phyllopus, Lipaphis erysimi, Lygus* spp. such as *L. hesperus, L. lineolaris, L. pratensis; Maconellicoccus hirsutus, Marchalina hellenica, Macropes excavatus, Macrosiphum* spp. such as *M. rosae, M. avenae, M. euphorbiae; Macrosteles quadrilineatus, Mahanarva fimbriolata, Megacopta cribraria, Megoura viciae, Melanaphis pyrarius, Melanaphis sacchari, Melanocallis (=Tinocallis) caryaefoliae, Metcafiella* spp., *Metopolophium dirhodum, Monellia costalis, Monelliopsis pecanis, Myzocallis coryli, Murgantia* spp., *Myzus* spp. such as *M. ascalonicus, M. cerasi, M. nicotianae, M. persicae, M. varians; Nasonovia ribis-nigri, Neotoxoptera formosana, Neomegalotomus* spp, *Nephotettix* spp. such as *N. malayanus, N. nigropictus, N. parvus, N. virescens; Nezara* spp. such as *N. viridula; Nilaparvata lugens, Nysius huttoni, Oebalus* spp. such as *O. pugnax; Oncometopia* spp., *Orthezia praelonga, Oxycaraenus hyalinipennis, Parabemisia myricae, Parlatoria* spp., *Parthenolecanium* spp. such as *P. corni, P. persicae; Pemphigus* spp. such as *P. bursarius, P. populivenae; Peregrinus maidis, Perkinsiella saccharicida, Phenacoccus* spp. such as *P. aceris, P. gossypii; Phloeomyzus passerinii, Phorodon humuli, Phylloxera* spp. such as *P. devastatrix, Piesma quadrata, Piezodorus* spp. such as *P. guildinii; Pinnaspis aspidistrae, Planococcus* spp. such as *P. citri, P. ficus; Prosapia bicincta, Protopulvinaria pyriformis, Psallus seriatus, Pseudacysta persea, Pseudaulacaspis pentagona, Pseudococcus* spp. such as *P. comstocki; Psylla* spp. such as *P. mali; Pteromalus* spp., *Pulvinaria amygdali, Pyrilla* spp., *Quadraspidiotus* spp., such as *Q. perniciosus; Quesada gigas, Rastrococcus* spp., *Reduvius senilis, Rhizoecus americanus, Rhodnius* spp., *Rhopalomyzus ascalonicus, Rhopalosiphum* spp. such as *R. pseudobrassicas, R. insertum, R. maidis, R. padi; Sagatodes* spp., *Sahlbergella singularis, Saissetia* spp., *Sappaphis mala, Sappaphis mali, Scaptocoris* spp., *Scaphoides titanus, Schizaphis graminum, Schizoneura lanuginosa, Scotinophora* spp., *Selenaspidus articulatus, Sitobion avenae, Sogata* spp., *Sogatella furcifera, Solubea insularis, Spissistilus festinus (=Stictocephala festina), Stephanitis nashi, Stephanitis pyrioides, Stephanitis takeyai, Tenalaphara malayensis, Tetraleurodes perseae, Therioaphis maculate, Thyanta* spp. such as *T. accerra, T. perditor; Tibraca* spp., *Tomaspis* spp., *Toxoptera* spp. such as *T. aurantii; Trialeurodes* spp. such as *T. abutilonea, T. ricini, T. vaporariorum; Triatoma* spp., *Trioza* spp., *Typhlocyba* spp., *Unaspis* spp. such as *U. citri, U. yanonensis*; and *Viteus vitifolii,*

Insects from the order Hymenoptera for example *Acanthomyops interjectus, Athalia rosae, Atta* spp. such as *A. capiguara, A. cephalotes, A. cephalotes, A. laevigata, A. robusta, A. sexdens, A. texana, Bombus* spp., *Brachymyrmex* spp., *Camponotus* spp. such as *C. floridanus, C. pennsylvanicus, C. modoc; Cardiocondyla nuda, Chalibion* sp, *Crematogaster* spp., *Dasymutilla occidentalis, Diprion* spp., *Dolichovespula maculata, Dorymyrmex* spp., *Dryocosmus kuriphilus, Formica* spp., *Hoplocampa* spp. such as *H. minuta, H. testudinea; Iridomyrmex humilis, Lasius* spp. such as *L. niger, Linepithema humile, Liometopum* spp., *Leptocybe invasa, Monomorium* spp. such as *M. pharaonis, Monomorium, Nylandria fulva, Pachycondyla chinensis, Paratrechina longicornis, Paravespula* spp., such as *P. germanica, P. pennsylvanica, P. vulgaris; Pheidole* spp. such as *P. megacephala*; *Pogonomyrmex* spp. such as *P. barbatus*, *P. californicus*, *Polistes rubiginosa*, *Prenolepis impairs*, *Pseudomyrmex gracilis*, *Schelipron* spp., *Sirex cyaneus*, *Solenopsis* spp. such as *S. geminata*, *S. invicta*, *S. molesta*, *S. richteri*, *S. xyloni*, *Sphecius speciosus*, *Sphex* spp., *Tapinoma* spp. such as *T. melanocephalum*, *T. sessile*; *Tetramorium* spp. such as *T. caespitum*, *T. bicarinatum*, *Vespa* spp. such as *V. crabro*; *Vespula* spp. such as *V. squamosal*; *Wasmannia auropunctata*, *Xylocopa* sp;

Insects from the order Orthoptera for example *Acheta domesticus*, *Calliptamus italicus*, *Chortoicetes terminifera*, *Ceuthophilus* spp., *Diastrammena asynamora*, *Dociostaurus maroccanus*, *Gryllotalpa* spp. such as *G. africana*, *G. gryllotalpa*; *Gryllus* spp., *Hieroglyphus daganensis*, *Kraussaria angulifera*, *Locusta* spp. such as *L. migratoria*, *L. pardalina*; *Melanoplus* spp. such as *M. bivittatus*, *M. femurrubrum*, *M. mexicanus*, *M. sanguinipes*, *M. spretus*; *Nomadacris septemfasciata*, *Oedaleus senegalensis*, *Scapteriscus* spp., *Schistocerca* spp. such as *S. Americana*, *S. gregaria*, *Stemopelmatus* spp., *Tachycines asynamorus*, and *Zonozerus variegatus*;

Pests from the Class Arachnida for example Acari, e.g. of the families Argasidae, Ixodidae and Sarcoptidae, such as *Amblyomma* spp. (e.g. *A. americanum*, *A. variegatum*, *A. maculatum*), *Argas* spp. such as *A. persicu*), *Boophilus* spp. such as *B. annulatus*, *B. decoloratus*, *B. microplus*, *Dermacentor* spp. such as *D. silvarum*, *D. andersoni*, *D. variabilis*, *Hyalomma* spp. such as *H. truncatum*, *Ixodes* spp. such as *I. ricinus*, *I. rubicundus*, *I. scapularis*, *I. holocyclus*, *I. pacificus*, *Rhipicephalus sanguineus*, *Ornithodorus* spp. such as *O. moubata*, *O. hermsi*, *O. turicata*, *Ornithonyssus bacoti*, *Otobius megnini*, *Dermanyssus gallinae*, *Psoroptes* spp. such as *P. ovis*, *Rhipicephalus* spp. such as *R. sanguineus*, *R. appendiculatus*, *Rhipicephalus evertsi*, *Rhizoglyphus* spp., *Sarcoptes* spp. such as*S. Scabiei*; and Family Eriophyidae including *Aceria* spp. such as *A. sheldoni*, *A. anthocoptes*, *Acallitus* spp., *Aculops* spp. such as *A. lycopersici*, *A. pelekassi*; *Aculus* spp. such as *A. schlechtendali*; *Colomerus vitis*, *Epitrimerus pyri*, *Phyllocoptruta oleivora*; *Eriophytes ribis* and *Eriophyes* spp. such as *Eriophyes sheldoni*; Family Tarsonemidae including *Hemitarsonemus* spp., *Phytonemus pallidus* and *Polyphagotarsonemus latus*, *Stenotarsonemus* spp. *Steneotarsonemus spinki*; Family Tenuipalpidae including *Brevipalpus* spp. such as *B. phoenicis*; Family Tetranychidae including *Eotetranychus* spp., *Eutetranychus* spp., *Oligonychus* spp., *Petrobia latens*, *Tetranychus* spp. such as *T. cinnabarinus*, *T. evansi*, *T. kanzawai*, *T, pacificus*, *T. phaseulus*, *T. telarius* and *T. urticae*; *Bryobia praetiosa*; *Panonychus* spp. such as *P. ulmi*, *P. citri*; *Metatetranychus* spp. and *Oligonychus* spp. such as *O. pratensis*, *O. perseae*, *Vasates lycopersici*; *Raoiella indica*, Family Carpoglyphidae including *Carpoglyphus* spp.; *Penthaleidae* spp. such as *Halotydeus destructor*; Family Demodicidae with species such as *Demodex* spp.; Family Trombicidea including *Trombicula* spp.; Family Macronyssidae including *Ornothonyssus* spp.; Family Pyemotidae including *Pyemotes tritici*; *Tyrophagus putrescentiae*; Family Acaridae including *Acarus siro*; Family Araneida including *Latrodectus mactans*, *Tegenaria agrestis*, *Chiracanthium* sp, *Lycosa* sp *Achaearanea tepidariorum* and *Loxosceles reclusa*;

Pests from the Phylum Nematoda, for example, plant parasitic nematodes such as rootknot nematodes, *Meloidogyne* spp. such as *M. hapla*, *M. incognita*, *M. javanica*; cyst-forming nematodes, *Globodera* spp. such as *G. rostochiensis*; *Heterodera* spp. such as *H. avenae*, *H. glycines*, *H. schachtii*, *H. trifolii*; Seed gall nematodes, *Anguina* spp.; Stem and foliar nematodes, *Aphelenchoides* spp. such as *A. besseyi*; Sting nematodes, *Belonolaimus* spp. such as *B. longicaudatus*; Pine nematodes, *Bursaphelenchus* spp. such as *B. lignicolus*, *B. xylophilus*; Ring nematodes, *Criconema* spp., *Criconemella* spp. such as *C. xenoplax* and *C. ornata*; and, *Criconemoides* spp. such as *Criconemoides informis*; *Mesocriconema* spp.; Stem and bulb nematodes, *Ditylenchus* spp. such as *D. destructor*, *D. dipsaci*; Awl nematodes, *Dolichodorus* spp.; Spiral nematodes, *Heliocotylenchus multicinctus*; Sheath and sheathoid nematodes, *Hemicycliophora* spp. and *Hemicriconemoides* spp.; *Hirshmanniella* spp.; Lance nematodes, *Hoploaimus* spp.; False rootknot nematodes, *Nacobbus* spp.; Needle nematodes, *Longidorus* spp. such as *L. elongatus*; Lesion nematodes, *Pratylenchus* spp. such as *P. brachyurus*, *P. neglectus*, *P. penetrans*, *P. curvitatus*, *P. goodeyi*; Burrowing nematodes, *Radopholus* spp. such as *R. similis*; *Rhadopholus* spp.; *Rhodopholus* spp.; Reniform nematodes, *Rotylenchus* spp. such as *R. robustus*, *R. reniformis*; *Scutellonema* spp.; Stubby-root nematode, *Trichodorus* spp. such as *T. obtusus*, *T. primitivus*; *Paratrichodorus* spp. such as *P. minor*; Stunt nematodes, *Tylenchorhynchus* spp. such as *T. claytoni*, *T. dubius*; Citrus nematodes, *Tylenchulus* spp. such as *T. semipenetrans*; Dagger nematodes, *Xiphinema* spp.; and other plant parasitic nematode species;

Insects from the order Isoptera for example *Calotermes flavicollis*, *Coptotermes* spp. such as *C. formosanus*, *C. gestroi*, *C. acinaciformis*; *Cornitermes cumulans*, *Cryptotermes* spp. such as *C. brevis*, *C. cavifrons*; *Globitermes sulfureus*, *Heterotermes* spp. such as *H. aureus*, *H. longiceps*, *H. tenuis*; *Leucotermes flavipes*, *Odontotermes* spp., *Incisitermes* spp. such as *I. minor*, *I. Snyder*; *Marginitermes hubbardi*, *Mastotermes* spp. such as *M. darwiniensis* *Neocapritermes* spp. such as *N. opacus*, *N. parvus*; *Neotermes* spp., *Procornitermes* spp., *Zootermopsis* spp. such as *Z. angusticollis*, *Z. nevadensis*, *Reticulitermes* spp. such as *R. hesperus*, *R. tibialis*, *R. speratus*, *R. flavipes*, *R. grassei*, *R. lucifugus*, *R. santonensis*, *R. virginicus*; *Termes natalensis*, Insects from the order Blattaria for example *Blatta* spp. such as *B. orientalis*, *B. lateralis*; *Blattella* spp. such as *B. asahinae*, *B. germanica*; *Leucophaea maderae*, *Panchlora nivea*, *Periplaneta* spp. such as *P. americana*, *P. australasiae*, *P. brunnea*, *P. fuligginosa*, *P. japonica*; *Supella longipalpa*, *Parcoblatta pennsylvanica*, *Eurycotis floridana*, *Pycnoscelus surinamensis*, Insects from the order Siphonoptera for example *Cediopsylla simples*, *Ceratophyllus* spp., *Ctenocephalides* spp. such as *C. felis*, *C. canis*, *Xenopsylla cheopis*, *Pulex irritans*, *Trichodectes canis*, *Tunga penetrans*, and *Nosopsyllus fasciatus*, Insects from the order Thysanura for example *Lepisma saccharina*, *Ctenolepisma urbana*, and *Thermobia domestica*, Pests from the class Chilopoda for example *Geophilus* spp., *Scutigera* spp. such as *Scutigera coleoptrata*;

Pests from the class Diplopoda for example *Blaniulus guttulatus*, *Julus* spp., *Narceus* spp., Pests from the class Symphyla for example *Scutigerella immaculata*, Insects from the order Dermaptera, for example *Forficula auricularia*, Insects from the order Collembola, for example *Onychiurus* spp., such as *Onychiurus armatus*, Pests from the order Isopoda for example, *Armadillidium vulgare*, *Oniscus asellus*, *Porcellio scaber*, Insects from the order Phthiraptera, for example *Damalinia* spp., *Pediculus* spp. such as *Pediculus humanus capitis*, *Pediculus humanus corporis*, *Pediculus humanus humanus*; *Pthirus pubis*, *Haematopinus* spp. such as *Hae-*

*matopinus eurysternus, Haematopinus suis; Linognathus* spp. such as *Linognathus vituli; Bovicola bovis, Menopon gallinae, Menacanthus stramineus* and *Solenopotes capillatus, Trichodectes* spp., Examples of further pest species which may be controlled by compounds of formula (I) include: from the Phylum Mollusca, class Bivalvia, for example, *Dreissena* spp.; class Gastropoda, for example, *Arion* spp., *Biomphalaria* spp., *Bulinus* spp., *Deroceras* spp., *Galba* spp., *Lymnaea* spp., *Oncomelania* spp., *Pomacea canaliclata, Succinea* spp.; from the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercora lis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti.*

The compounds of the invention are suitable for use in treating or protecting animals against infestation or infection by parasites. Therefore, the invention also relates to the use of a compound of the invention for the manufacture of a medicament for the treatment or protection of animals against infestation or infection by parasites. Furthermore, the invention relates to a method of treating or protecting animals against infestation and infection by parasites, which comprises orally, topically or parenterally administering or applying to the animals a parasiticidally effective amount of a compound of the invention.

The present invention also relates to the non-therapeutic use of compounds of the invention for treating or protecting animals against infestation and infection by parasites. Moreover, the invention relates to a non-therapeutic method of treating or protecting animals against infestation and infection by parasites, which comprises applying to a locus a parasiticidally effective amount of a compound of the invention.

The compounds of the invention are further suitable for use in combating or controlling parasites in and on animals. Furthermore, the invention relates to a method of combating or controlling parasites in and on animals, which comprises contacting the parasites with a parasitically effective amount of a compound of the invention.

The invention also relates to the non-therapeutic use of compounds of the invention for controlling or combating parasites. Moreover, the invention relates to a non-therapeutic method of combating or controlling parasites, which comprises applying to a locus a parasiticidally effective amount of a compound of the invention.

The compounds of the invention can be effective through both contact (via soil, glass, wall, bed net, carpet, blankets or animal parts) and ingestion (e.g. baits). Furthermore, the compounds of the invention can be applied to any and all developmental stages.

The compounds of the invention can be applied as such or in form of compositions comprising the compounds of the invention.

The compounds of the invention can also be applied together with a mixing partner, which acts against pathogenic parasites, e.g. with synthetic coccidiosis compounds, polyetherantibiotics such as Amprolium, Robenidin, Toltrazuril, Monensin, Salinomycin, Maduramicin, Lasalocid, Narasin or Semduramicin, or with other mixing partners as defined above, or in form of compositions comprising said mixtures.

The compounds of the invention and compositions comprising them can be applied orally, parenterally or topically, e.g. dermally. The compounds of the invention can be systemically or non-systemically effective.

The application can be carried out prophylactically, therapeutically or non-therapeutically. Furthermore, the application can be carried out preventively to places at which occurrence of the parasites is expected.

As used herein, the term "contacting" includes both direct contact (applying the compounds/compositions directly on the parasite, including the application directly on the animal or excluding the application directly on the animal, e.g. at it's locus for the latter) and indirect contact (applying the compounds/compositions to the locus of the parasite). The contact of the parasite through application to its locus is an example of a non-therapeutic use of the compounds of the invention.

The term "locus" means the habitat, food supply, breeding ground, area, material or environment in which a parasite is growing or may grow outside of the animal.

As used herein, the term "parasites" includes endo- and ectoparasites. In some embodiments of the invention, endoparasites can be preferred. In other embodiments, ectoparasites can be preferred. Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the invention are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans,* and *Nosopsyllus fasciatus*; cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis*; flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis*; lice (Phthiraptera), e.g. *Pediculus*

*humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*; ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae; Actinedida* (Prostigmata) und *Acaridida* (Astigmata), e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp; Bugs (Heteropterida): *Cimex lectularius, Cimex hemipterus, Reduvius senilis, Triatoma* spp., *Rhodnius* ssp., *Panstrongylus* ssp., and *Arilus critatus; Anoplurida*, e.g. *Haematopinus* spp., *Linognathus* spp., *Pediculus* spp., *Phtirus* spp., and *Solenopotes* spp.; *Mallophagida* (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp.; Roundworms Nematoda: Wipeworms and Trichinosis (Trichosyringida), e.g. *Trichinellidae* (*Trichinella* spp.), (Trichuridae) *Trichuris* spp., *Capillaria* spp.; Rhabditida, e.g. *Rhabditis* spp., *Strongyloides* spp., *Helicephalobus* spp.; Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp., *Aleurostrongylus abstrusus*, and *Dioctophyma renale*; Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi; Camallanida*, e.g. *Dracunculus medinensis* (guinea worm); Spirurida, e.g. *Thelazia* spp., *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp.; Thorny headed worms (Acanthocephala), e.g. *Acanthocephalus* spp., *Macracanthorhynchus hirudinaceus* and *Oncicola* spp.; Planarians (Plathelminthes): Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp.; Cercomeromorpha, in particular *Cestoda* (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

As used herein, the term "animal" includes warm-blooded animals (including humans) and fish. Preferred are mammals, such as cattle, sheep, swine, camels, deer, horses, pigs, poultry, rab-bits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels. Particularly preferred are domestic animals, such as dogs or cats.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally, it is favorable to apply the compounds of the invention in total amounts of 0.5 mg/kg to 100 mg/kg per day, preferably 1 mg/kg to 50 mg/kg per day.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further auxiliaries such as acids, bases, buffer salts, preservatives, and solubilizers. Suitable auxiliaries for injection solutions are known in the art. The solutions are filtered and filled sterile.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on. Solutions for use on the skin are prepared according to the state of the art and according to what is described above for injection solutions, sterile procedures not being necessary.

Gels are applied to or spread on the skin or introduced into body cavities. Gels are prepared by treating solutions which have been prepared as described in the case of the injection solutions with sufficient thickener that a clear material having an ointment-like consistency results. Suitable thickeners are known in the art.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added. Suitable such auxiliaries are known in the art.

Emulsions can be administered orally, dermally or as injections. Emulsions are either of the water-in-oil type or of the oil-in-water type. They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances. Suitable hydrophobic phases (oils), suitable hydrophilic phases, suitable emulsifiers, and suitable further auxiliaries for emulsions are known in the art.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers. Suitable suspending agents, and suitable other auxiliaries for suspensions including wetting agents are known in the art.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form. Suitable auxiliaries for this purpose are known in the art.

The compositions which can be used in the invention can comprise generally from about 0.001 to 95% of the compound of the invention.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

Topical application may be conducted with compound-containing shaped articles such as collars, medallions, ear tags, bands for fixing at body parts, and adhesive strips and foils.

Generally it is favorable to apply solid formulations which release compounds of the invention in total amounts of 10 mg/kg to 300 mg/kg, preferably 20 mg/kg to 200 mg/kg, most preferably 25 mg/kg to 160 mg/kg body weight of the treated animal in the course of three weeks.

The following examples illustrate the invention.

Characterization

HPLC-MS data of compounds are summarized in Table B. The following HPLC-methods were applied:

HPLC Method A: MSD4/5: Shimadzu Nexera UHPLC+ Shimadzu LCMS 20-20, ESI. Column: Phenomenex Kinetex 1.7 μm XB-C18 100A, 50×2.1 mm. Mobile Phase: A: water+0.1% trifluoroacetic acid; B: acetonitrile. Temperature: 60° C. Gradient: 5% B to 100% B in 1.50 min; 100% B 0.25 min. Flow: 0.8 ml/min to 1.0 ml/min in 1.51 min. MS method: ESI positive. Mass range (m/z): 100-1400.

HPLC Method B: MSD4/5: Shimadzu Nexera UHPLC+ Shimadzu LCMS 20-20, ESI. Column: Phenomenex Kinetex 1.7 μm XB-C18 100A, 50×2.1 mm. Mobile Phase: A: water+0.1% trifluoroacetic acid; B: acetonitrile. Temperature: 60° C. Gradient: 5% B to 100% B in 1.50 min; 100% B 0.25 min. Flow: 0.8 ml/min to 1.0 ml/min in 1.51 min. MS method: ESI positive. Mass range (m/z): 100-700.

$^1$H-NMR: The signals were characterized by chemical shift (ppm) vs. tetramethylsilane, by their multiplicity and by their integral (relative number of hydrogen atoms given). The following abbreviations are used to characterize the multiplicity of the signals: br=broad, m=multiplett, q=quartett, t=triplett, d=doublet and s=singlet.

Abbreviations used are: $CDCl_3$ for deuterated chloroform, δ for chemical shift, EtOAc for ethylacetate, g for gramm(s) h for hour(s), M for mol/l, MHz for Megahertz, min for minute(s), ml for milliliter(s), ppm for parts-per-million, THF for tetrahydrofuran.

Synthesis Example: 3-(2-chlorothiazol-5-yl)-6-(4-methoxyphenyl)-1,8-dimethyl-7-oxo-2,3-dihydro-imidazo[1,2-a]pyrimidin-8-ium-5-olate (Compound C-1)

Step 1: tert-butyl N-[2-[methoxy(methyl)amino]-2-oxo-ethyl]-N-methyl-carbamate (C-1a)

2-[tert-butoxycarbonyl(methyl)amino]acetic acid (5.72 g; 30.23 mmol; 1.00 equiv) was dissolved in dichloromethane (60 ml) and carbonyldiimidazole (5.10 g) was added dropwise at room temperature. Evolution of the gas was observed. Reaction mixture was stirred at 23° C. for 90 min. Then, N,O-dimethylhydroxylamine hydrochloride (3.25 g) was added and the reaction mixture was stirred at 23° C. for additional 18 h. The reaction mixture was then diluted with EtOAc and extracted with an aqueous solution of HCl (1 M), followed by extraction with a saturated aqueous solution of $NaHCO_3$. The combined organic extracts were concentrated in vacuo and the residue was purified by column chromatography to obtain compound C-1a (5.82 g, 83% yield). Characterization by $^1$H-NMR (400 MHz, $CDCl_3$): δ ppm 4.15 (s, 2H); 3.72 (s, 3H); 3.20 (s, 3H); 2.94 (s, 3H); 1.48 (s, 9H).

Step 2: tert-butyl N-[2-(2-chlorothiazol-5-yl)-2-oxo-ethyl]-N-methyl-carbamate (C-1b)

A round-bottom flask was dried under vacuum and washed with Ar. 2-Chlorothiozole (3.08 g) was dissolved in dry THF (9.3 ml) under argon and cooled down to −20° C. i-PrMgCl (21.72 ml; 1.19 M; 1.27 equiv) was added dropwise over 5 min. The resulting mixture was stirred at −20° C. for 3 h, providing the chloro-(2-chlorothiazol-5-yl)magnesium solution in THF. Compound C-1a (5.00 g) was placed in another round-bottom flask that had been dried under vacuum and washed with Ar, dissolved in dry THF (5.3 ml) and cooled down to −20° C. Chloro-(2-chlorothiazol-5-yl)magnesium solution in THF was added dropwise over 10 min and the reaction mixture was stirred at −20° C. for 3 h. The reaction mixture was diluted with EtOAc and extracted with a saturated aqueous solution of $NH_4Cl$. The combined organic extracts were concentrated in vacuo and the residue was purified by column chromatography to obtain compound C-1b (3.72 g, 63% yield). Characterization by $^1$H-NMR (400 MHz, $CDCl_3$): δ ppm 8.18 (s, 1H); 4.49 (s, 2H); 2.99 (s, 3H); 1.39 (s, 9H).

Step 3: tert-butyl N-[(2Z)-2-tert-butylsulfinylimino-2-(2-chlorothiazol-5-yl)ethyl]-N-methyl-carbamate (Compound C-1c)

Compound C-1b (3.50 g) was dissolved in dry THF (25 ml) under Ar. 2-Methylpropane-2-sulfinamide (3.85 g) was added followed by the solution of titanium(IV) ethoxide (2.79 ml) in THF (5 ml). The reaction mixture was stirred at 50° C. for 5 h and then at 23° C. for 12 h. The reaction mixture was diluted with EtOAc and extracted with water. The combined organic extracts were concentrated in vacuo and the residue was purified by column chromatography to obtain compound C-1c (3.82 g, 80% yield). Characterization by $^1$H-NMR (400 MHz, $CDCl_3$): δ ppm 8.18 (s, 1H); 4.97-4.84 (m, 2H); 2.99 (s, 3H); 1.43 (s, 9H); 1.30 (s, 9H).

Step 4: tert-butyl N-[2-(tert-butylsulfinylamino)-2-(2-chlorothiazol-5-yl)ethyl]-N-methyl-carbamate (Compound C-1d)

Compound C-1c (3.00 g) was dissolved in a mixture comprising THF (35 ml) and $CH_3OH$ (4 ml) and cooled down to −4° C. Sodium borohydride (0.144 g) was added and the reaction mixture was stirred at −4° C. for 90 min. The reaction mixture was then diluted with a saturated aqueous solution of $NH_4Cl$ and extracted with EtOAc. The combined organic extracts were concentrated in vacuo and the residue was purified by column chromatography to obtain compound C-1d as a mixture of two diastereomers (2.8 g, 93% yield). Characterization by $^1$H-NMR (400 MHz, $CDCl_3$, one diastereomer): δ ppm 7.42 (s, 1H); 5.20 (br. s., 1H); 3.94 (br. s., 1H); 3.16 (br. s., 1H); 2.90 (s, 3H); 1.45 (s, 9H); 1.22 (s, 9H).

Step 5: N-[1-(2-chlorothiazol-5-yl)-2-(methylamino)ethyl]-2-methyl-propane-2-sulfinamide (Compound C-1e)

Compound C-1d (3.18 g) was dissolved in $CH_2Cl_2$ (80 ml). Trifluoroacetic acid (10 ml) was added and reaction mixture was stirred at 23° C. for 22 h, before being diluted with water and neutralized with a saturated aqueous solution of $NaHCO_3$. The aqueous phase of the reaction mixture was then extracted with EtOAc. The combined organic phases were concentrated in vacuo and the residue was purified by column chromatography to obtain compound C-1e as a mixture of two diastereomers (2.35 g, 98% yield). Characterization by $^1$H-NMR (400 MHz, $CDCl_3$): δ ppm 11.45 (br. s., 1H); 8.28 (br. s., 1H); 7.43 (s, 1H); 5.19 (br. s., 1H), 4.13 (br. s., 1H); 3.29 (br. s., 1H); 2.81 (s, 3H); 1.23 (s, 9H).

Step 6: (Z)-4-(2-chlorothiazol-5-yl)-N,1-dimethyl-imidazolidin-2-imine (Compound C-1f)

Compound C-1e (1.571 g) and methyl isothiocyanate (0.582 g) were added to dry toluene (40 ml) and heated to 100° C. for 90 min. The reaction mixture was then concentrated in vacuo and residue was purified by column chromatography to obtain compound C-1f (0.50 g; 40% yield).

Step 7: 3-(2-chlorothiazol-5-yl)-6-(4-methoxyphenyl)-1,8-dimethyl-7-oxo-2,3-dihydroimidazo[1,2-a]pyrimidin-8-ium-5-olate (Compound C-1)

Compound C-1f (0.178 g) added to dry toluene (8 ml) and heated to 110° C. bis(2,4,6-Trichlorophenyl) 2-(4-methoxyphenyl)propanedioate (0.562 g) was added at once and the reaction mixture was stirred at 110° C. for 6 h. After cooling to 20 to 25° C. the reaction mixture was concentrated in vacuo. The residue was purified by column chromatography to obtain compound C-1 (0.121 g; 39% yield). Characterization by $^1$H-NMR (400 MHz, $CDCl_3$): δ ppm 7.70 (d, J=8.4 Hz, 2H), 7.50 (s, 1H), 6.93-6.80 (m, 2H), 5.75-5.63 (m, 1H), 5.30 (s, 1H), 3.79 (s, 3H), 3.71-3.61 (m, 2H), 3.52 (s, 3H), 3.14 (s, 3H).

The following examples in Table B can be synthesized analogously as described in the Synthesis Example.

TABLE B

| No | Formula | Phys. Chem. Data*: HPLC Method Retention time; m/z |
|---|---|---|
| C-2 | (structure) | A: 1.02; 461.3 |

TABLE B-continued

| No | Formula | Phys. Chem. Data*: HPLC Method Retention time; m/z |
|---|---|---|
| C-3 | | B: 0.775; 375 |
| C-4 | | B: 1.041; 445 |
| C-5 | | B: 1.041; 445 |
| C-6 | | B: 0.787; 405 |
| C-7 | | B: 1.098, 456.9 |

TABLE B-continued
| No | Formula | Phys. Chem. Data*: HPLC Method Retention time; m/z |
|---|---|---|
| C-8 | 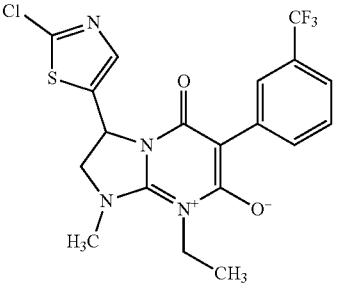 [SMILES: CC[n+]1c([O-])c(-c2cccc(C(F)(F)F)c2)c(=O)n2c1N(C)CC2c1cnc(Cl)s1] | B: 0.827; 419 |
| C-9 | 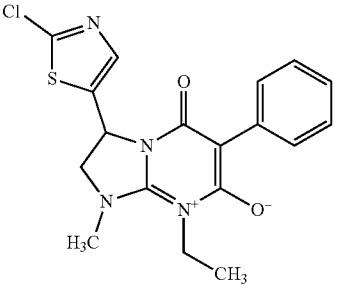 [SMILES: CC[n+]1c([O-])c(-c2ccccc2)c(=O)n2c1N(C)CC2c1cnc(Cl)s1] | B: 1.022; 457 |
| C-10** | 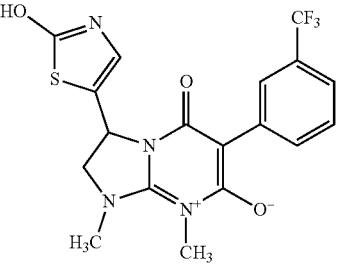 [SMILES: CN1CC(c2cnc(O)s2)n2c1[n+](C)c([O-])c(-c1cccc(C(F)(F)F)c1)c2=O] | B: 0.826; 1.389 |
| C-11 | 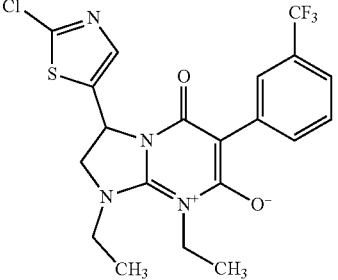 [SMILES: CCN1CC(c2cnc(Cl)s2)n2c1[n+](CC)c([O-])c(-c1cccc(C(F)(F)F)c1)c2=O] | B: 0.783; 425 |
| C-12 | 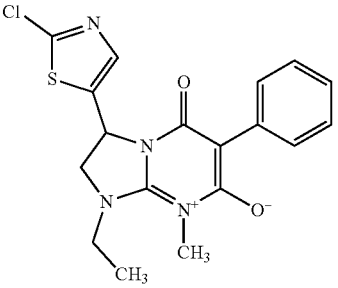 [SMILES: CCN1CC(c2cnc(Cl)s2)n2c1[n+](C)c([O-])c(-c1ccccc1)c2=O] | B: 1.101; 471 |

TABLE B-continued
| No | Formula | Phys. Chem. Data*: HPLC Method Retention time; m/z |
|---|---|---|
| C-13 | 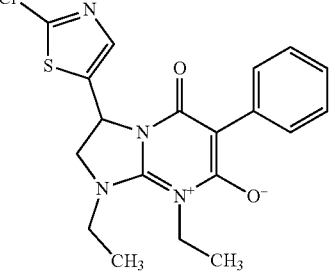 | B: 1.043; 457 |
| C-14 | 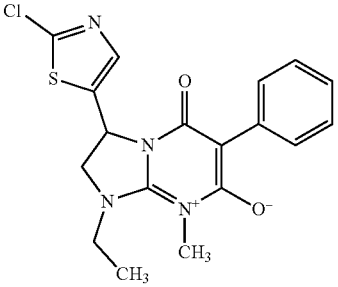 [SMILES: CCN1CC(c2cnc(Cl)s2)n2c1[n+](C)c([O-])c(-c1ccccc1)c2=O] | B: 0.869; 403 |
| C-15 | 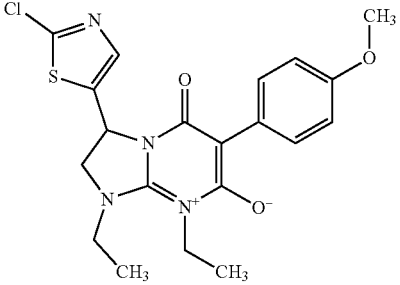 [SMILES: CCN1CC(c2cnc(Cl)s2)n2c1[n+](CC)c([O-])c(-c1ccc(OC)cc1)c2=O] | B: 0.838; 389 |
| C-16 | 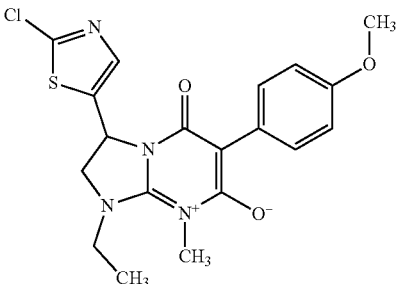 | B: 0.864; 433 |
| C-17 | 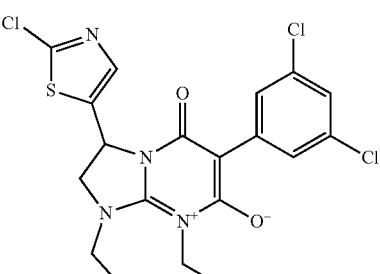 | B: 0.813; 419.1 |

TABLE B-continued

| No | Formula | Phys. Chem. Data*: HPLC Method Retention time; m/z |
|---|---|---|
| C-18 | | B: 1.137; 471 |
| C-19 | | B: 1.077; 456.9 |
| C-20 | | B: 0.976; 442.9 |
| C-21 | | B: 0.998; 439 |
| C-22 | | B: 0.998; 439 |

TABLE B-continued
| No | Formula | Phys. Chem. Data*: HPLC Method Retention time; m/z |
|---|---|---|
| C-23 | 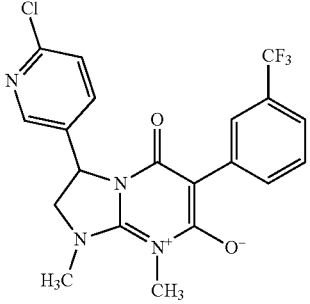 [SMILES: CN1CC(c2ccc(Cl)nc2)n2c1[n+](C)c([O-])c(-c1cccc(C(F)(F)F)c1)c2=O] | B: 0.966; 399 |
| C-24 | 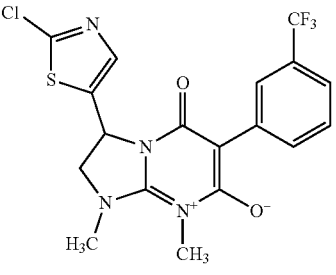 [SMILES: CN1CC(c2cnc(Cl)s2)n2c1[n+](C)c([O-])c(-c1cccc(C(F)(F)F)c1)c2=O] | B: 0.853; 425 |
| C-25 | 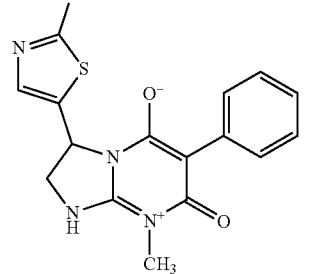 | B: 0.739; 361.1 |
| C-26 | 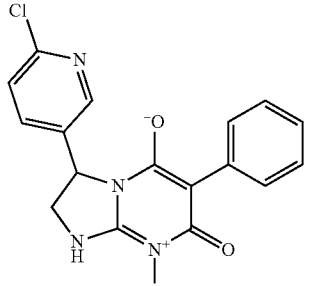 | B: 0.691; 355 |
| C-27 | 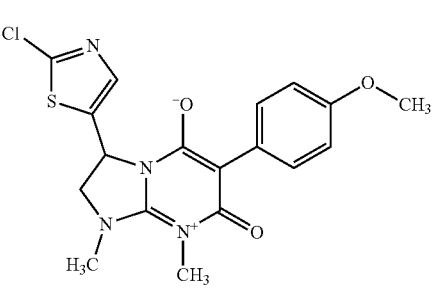 | B: 0.787; 405 |

TABLE B-continued

| No | Formula | Phys. Chem. Data*: HPLC Method Retention time; m/z |
|---|---|---|
| C-28 | | B: 1.043; 457 |
| C-29 | | B: 0.847; 388.9 |
| C-30 | | B: 1.054; 451 |
| C-31 | | B: 1.01; 481 |
| C-32 | | B: 0.84; 389 |

TABLE B-continued

| No | Formula | Phys. Chem. Data*: HPLC Method Retention time; m/z |
|---|---|---|
| C-33 | | B: 0.829; 400 |
| C-34 | | B: 0.996; 500.9 |
| C-35 | | B: 0.905; 403 |
| C-36 | | B: 1.182; 513 |

TABLE B-continued
| No | Formula | Phys. Chem. Data*: HPLC Method Retention time; m/z |
|---|---|---|
| C-37 | 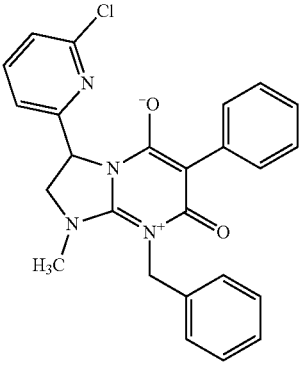 | B: 0.961; 445 |
| C-38 | 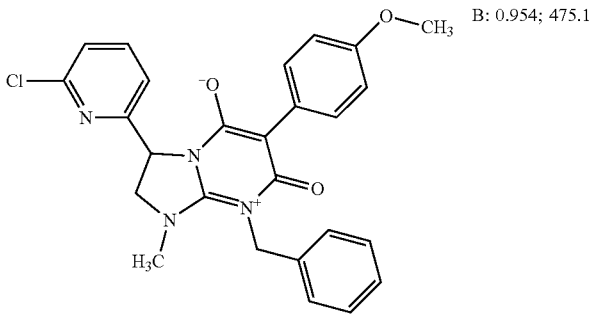 | B: 0.954; 475.1 |
| C-39 | 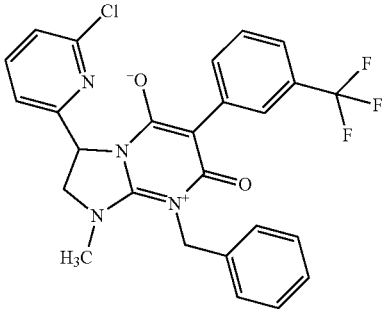 | B: 1.113; 513 |
| C-40 | 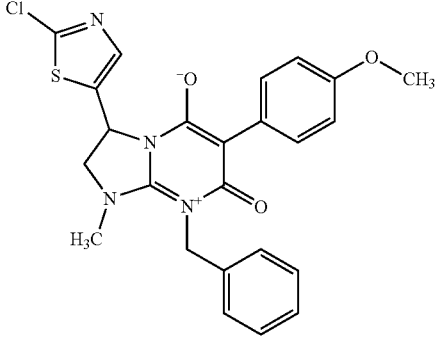 | B: 0.982; 480.9 |

TABLE B-continued

| No | Formula | Phys. Chem. Data*: HPLC Method Retention time; m/z |
|---|---|---|
| C-41 | | B: 1.146; 519 |
| C-42 | | B: 1.223; 520.8 |
| C-43 | | B: 0.993; 450.9 |

Compounds of formula (I) that were synthesized in analogy to the Synthesis Example.
*HPLC Method: retention time in minutes; mass charge ratio m/z.
** Not according to the invention.

EXAMPLE—SEPARATION OF THE ENANTIOMERS

Enantiomers of the compound of formula (I) could be synthesized separately using chiral (R)-Ellman's sulfonamide (R-(+)-2-methyl-2-propansulfinamid) in the synthesis of the compound C-Ic, followed by reduction reaction with $NaBH_4$ and separation of the diastereomers.

Procedure for the Separation of the Diastereomers:

The diastereomers were separated using a CombiFlashRf Teledyne Isco device, on a puriFlash Interchim PF-15SIHC-JP/40G column. Cyclohexane, Ethylacetate, 254 nm, 280 nm. 4 min—100% Cyclohexane; in 36 min—40% Ethylacetate; 25 min—Ethylacetate. Characterization by HPLC Method B resulted in retention times of 1.077 min (fist diastereomer) and 1.131 min (second diastereomer) for the diastereomers.

Subsequent deprotection reaction of each of the diastereomers would give a compound C-1e as a single enantiomer. X-ray crystallography of the compound produced from the second diastereomer showed an (S)-configuration at the newly formed chiral center at the C-atom. Following the standard procedures which were described above, the compounds of formula (I) could be synthesized in a pure (S)- or (R)-enantiomeric form.

The biological activity of the compounds of formula (I) of the present invention can be evaluated in biological tests as described in the following.

BIOLOGICAL EXAMPLES

If not otherwise specified, the test solutions are prepared as follows:

The active compound is dissolved at the desired concentration in a mixture of 1:1 (vol:vol) distilled water:acetone. The test solution is prepared at the day of use.

Test solutions are prepared in general at concentrations of 1000 ppm, 500 ppm, 300 ppm, 100 ppm and 30 ppm (wt/vol).

B.1. Boll Weevil (*Anthonomus grandis*)

For evaluating control of boll weevil (*Anthonomus grandis*) the test unit consisted of 96-well-microtiter plates containing an insect diet and 5-10 *A. grandis* eggs.

The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 25±1° C. and about 75±5% relative humidity for 5 days. Egg and larval mortality was then visually assessed.

In this test, the following compounds at 2500 ppm showed over 75% mortality in comparison with untreated controls: C-6, C-7, C-8, C-14, C-16, C-18

B.3. Cowpea Aphid (*Aphis craccivora*)

The active compound is dissolved at the desired concentration in a mixture of 1:1 (vol:vol) distilled water:acetone. Surfactant (Alkamuls® EL 620) is added at a rate of 0.1% (vol/vol). The test solution is prepared at the day of use.

Potted cowpea plants were colonized with approximately 50-100 aphids of various stages by manually transferring a leaf tissue cut from infested plant 24 hours before application. Plants were sprayed after the pest population has been recorded. Treated plants are maintained on light carts at about 28° C. Percent mortality was assessed after 72 hours.

In this test, the following compounds at 300 ppm showed over 75% mortality in comparison with untreated controls: C-1, C-3, C-4, C-5, C-6, C-7, C-8, C-9, C-11, C-12, C-13, C-14, C-15, C-16, C-17, C-18, C-19, C-20.

B.4. Diamond Back Moth (*Plutella xylostella*)

The active compound is dissolved at the desired concentration in a mixture of 1:1 (vol:vol) distilled water:acetone. Surfactant (Alkamuls® EL 620) is added at a rate of 0.1% (vol/vol). The test solution is prepared at the day of use.

Leaves of cabbage were dipped in test solution and air-dried. Treated leaves were placed in petri dish enlined with moist filter paper and inoculated with ten $3^{rd}$ instar larvae. Mortality was recorded 72 hours after treatment. Feeding damages were also recorded using a scale of 0-100%.

In this test, the following compounds at 300 ppm showed over 75% mortality in comparison with untreated controls: C-4, C-5, C-6, C-9, C-11, C-12, C-14, C-17, C-18

B.5. Green Peach Aphid (*Myzus persicae*, Mixed Life Stages)

B.5.1. The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 10 or 20 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24-hr photoperiod at about 25° C. and about 20-40% relative humidity. Aphid mortality on the treated plants, relative to mortality on untreated control plants, was determined after 5 days.

In this test, the compound C-5 at 300 ppm showed over 75% mortality in comparison with untreated controls.

B.5.2. For evaluating control of green peach aphid (*Myzus persicae*) through systemic means the test unit consisted of 96-well-microtiter plates containing liquid artificial diet under an artificial membrane. The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, the following compounds at 2500 ppm showed over 75% mortality in comparison with untreated controls: C-1, C-2, C-3, C-4, C-5, C-6, C-7, C-8, C-9, C-11, C-12, C-13, C-14, C-15, C-16, C-17, C-18, C-19, C-20, C-21, C-23, C-24, C-25, C-26, C-27, C-28, C-29, C-30, C-31, C-32, C-33, C-34.

B.8. Rice Green Leafhopper (*Nephotettix virescens*)

Rice seedlings were cleaned and washed 24 hours before spraying. The active compounds were formulated in 50:50 acetone:water (vol:vol), and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, the following compounds at 300 ppm showed over 75% mortality in comparison with untreated controls: C-3, C-4, C-5, C-6, C-7, C-8, C-9, C-11, C-12, C-13, C-14, C-17, C-18

B.9. Rice Brown Plant Hopper (*Nilaparvata lugens*)

Rice seedlings were cleaned and washed 24 hours before spraying. The active compounds were formulated in 50:50 acetone:water (vol:vol) and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, the following compounds at 300 ppm showed over 75% mortality in comparison with untreated controls: C-3, C-4, C-5, C-6, C-8, C-9, C-11, C-12, C-13, C-14, C-18

B.10. Silverleaf Whitefly (*Bemisia argentifolii*) (Adults)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% ace-tone:50% water (v/v). A non-ionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (24-hour photoperiod) to prevent trapping of heat inside the cup. Mortality was assessed 3 days after treatment, compared to untreated control plants.

In this test, the compound C-5 at 300 showed over 75% mortality in comparison with untreated controls.

B.11. Southern Armyworm (*Spodoptera eridania*), 2nd Instar Larvae

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% ace-tone:50% water (v/v). A nonionic surfactant (Kinetic®) was included in the solution at a volume of 0.01% (v/v).

Lima bean plants (variety *sieva*) were grown 2 plants to a pot and selected for treatment at the 1$^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compounds C-4, C-5, C-8, C-9, C-12, C-17, C-18, C-20, C-28, C-29, C-34, C-41, C-43 at 300 ppm showed over 75% mortality in comparison with untreated controls.

B.12. Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs.

The compounds were formulated using a solution containing 75% v/v water and 25% v/v DMSO. Different concentrations of formulated compounds were sprayed onto the insect diet at 10 µl, using a custom built micro atomizer, at two replications.

After application, microtiter plates were incubated at about 28±1° C. and about 80±5% relative humidity for 5 days. Egg and larval mortality was then visually assessed.

In this test, the following compounds at 2500 ppm showed over 75% mortality in comparison with untreated controls: C-3, C-4, C-5, C-6, C-7, C-8, C-11, C-12, C-14, C-17, C-18, C-19

B.13. Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, the following compounds at 2500 ppm showed over 75% mortality in comparison with untreated controls: C-3, C-4, C-5, C-6, C-7, C-8, C-9, C-11, C-12, C-13, C-14, C-15, C-16, C-17, C-18, C-19, C-20

B.14. Yellow Fever Mosquito (*Aedes aegypti*)

For evaluating control of yellow fever mosquito (*Aedes aegypti*) the test unit consisted of 96-well-microtiter plates containing 200 µl of tap water per well and 5-15 freshly hatched *A. aegypti* larvae. The active compounds were formulated using a solution containing 75% (v/v) water and 25% (v/v) DMSO. Different concentrations of formulated compounds or mixtures were sprayed onto the insect diet at 2.5 µl, using a custom built micro atomizer, at two replications.

After application, microtiter plates were incubated at 28+1° C., 80+5% RH for 2 days. Larval mortality was then visually assessed.

In this test, the following compounds at 2500 ppm showed over 75% mortality in comparison with untreated controls: C-11, C-12, C-13, C-14, C-15, C-16, C-17, C-18

B.15. Green Soldier Stink Bug (*Nezara viridula*)

The active compound was dissolved at the desired concentration in a mixture of 1:1 (vol:vol) distilled water: aceteone. Surfactant (Kinetic® HV) is added at a rate of 0.01% (vol/vol). The test solution was prepared at the day of use.

Soybean pods were placed in 90×50 mm glass Petri dishes lined with moist filter paper and inoculated with ten late 3rd instar *N. viridula*. Using a hand atomizer, an approximately 2 ml solution is sprayed into each Petri dish. Treated cups were kept at about 25-26° C. and relative humidity of about 65-70%. Percent mortality was recorded after 5 days. In this test, compounds C-5 and C-20 at 300 ppm showed over 75% mortality in comparison with untreated controls.

The invention claimed is:
1. A compound of formula (I):

(I)

$$\text{[structure: Het-substituted bicyclic imidazo-pyrimidinone with Z-R}^2\text{, N}^+\text{-R}^1\text{, O}^-\text{, and R}^3\text{ substituents]}$$

or an agriculturally or veterinary acceptable salt, stereoisomer, or tautomer thereof, wherein:
  Het is a 3- to 10-membered heterocyclic ring or a 7- to 11-membered heterocyclic ring system;
    wherein the 3- to 10-membered heterocyclic ring or 7- to 11-membered heterocyclic ring system contains 1, 2, 3, or 4 ring members independently selected from the group consisting of $N(R^c)_p$, O, and S;
    wherein the 3- to 10-membered heterocyclic ring or 7- to 11-membered heterocyclic ring system contains 0, 1, 2, 3, or 4 $N(R^c)_p$ ring members, 0, 1, or 2 O ring members, or 0, 1, or 2 S ring members;
    wherein 1, 2, or 3 C ring members of the 3- to 10-membered heterocyclic ring or 7- to 11-membered heterocyclic ring system are optionally and independently replaced with 1, 2, or 3 ring members independently selected from the group consisting of C(O) and C(S);
    wherein 1 or 2 S ring members of the 3- to 10-membered heterocyclic ring or 7- to 11-membered heterocyclic ring system are optionally and independently replaced with 1 or 2 $S(O)_o(NR^b)_q$ ring members; and
    wherein the 3- to 10-membered heterocyclic ring or 7- to 11-membered heterocyclic ring system is optionally substituted with 1, 2, 3, 4, or 5 independently selected $R^a$ substituents;
  Z is a direct bond, —$C(R^aR^{aa})O$—, —$C(X^1)$—, —$C(X^1)Y^1$—, —$NR^b$—, —O—, —$S(O)_m$—, or —$Y^1C(X^1)$—;
  $X^1$ is $NR^b$, O, or S;
  $Y^1$ is $NR^c$, O, or S;
  $R^1$ is H, $C_1$-$C_8$ alkyl, $C_2$-$C_8$ alkenyl, $C_2$-$C_8$ alkynyl, $C(NR^c)R^c$, $C(NNR^bR^c)R^c$, $C(N[NR^cC(O)R^b])R^c$, $C(N[NR^cC(O)OR^c])R^c$, $C(NOR^c)R^c$, $C(O)R^b$, $C(O)NR^bR^c$, $C(O)OC(O)C_1$-$C_4$ alkyl, $C(O)OC_3$-$C_6$ cycloalkyl, C(O)O-(saturated, partially unsaturated, or aromatic 3- to 6-membered carbocyclic or heterocyclic ring), $C(S)NR^bR^c$, $NR^bR^c$, $N(CR^bR^c)$, $NR^cC(O)R^c$, $NR^cC(O)NR^bR^c$, $NR^cC(O)OR^e$, $NR^cS(O)_2R^b$, $NR^cS(O)_2NR^bR^c$, $OC(O)R^c$, $OC(O)NR^bR^e$, $OC(O)OR^e$, $S(O)_o(NR^b)_qR^c$, $S(O)_2NR^bR^c$, $Si(R^d)_3$, cycloalkyl-$C_7$-$C_{14}$ cycloalkyl, or a saturated, partially unsaturated, or aromatic 3- to 11-membered carbocyclic or heterocyclic ring or ring system;
    wherein the saturated, partially unsaturated, or aromatic 3- to 11-membered heterocyclic ring or ring system contains 1, 2, 3, or 4 ring members independently selected from the group consisting of $N(R^c)_p$, O, and S;
    wherein 1 or more S ring members of the 3- to 11-membered heterocyclic ring or ring system are optionally and independently oxidized; and
    wherein the $C_1$-$C_8$ alkyl, $C_2$-$C_8$ alkenyl, $C_2$-$C_8$ alkynyl, cycloalkyl-$C_7$-$C_{14}$ cycloalkyl, or saturated, partially unsaturated, or aromatic 3- to 11-membered carbocyclic or heterocyclic ring or ring system is optionally substituted with 1, 2, 3, 4, or 5 independently selected $R^a$ substituents;
  $R^2$ is H, halogen, CN, $C_1$-$C_8$ alkyl, alkyl-$C_7$-$C_{10}$ cycloalkyl, alkyl-($C_5$-$C_{10}$ alkylcycloalkyl), $C_2$-$C_8$ alkenyl, $C_2$-$C_8$ alkynyl, cycloalkyl-$C_7$-$C_{14}$ cycloalkyl, a saturated, partially unsaturated, or aromatic 3- to 10-membered carbocyclic or heterocyclic ring, or a saturated, partially unsaturated, or aromatic 7- to 11-membered carbocyclic or heterocyclic ring system;
    wherein the saturated, partially unsaturated, or aromatic 3- to 10-membered heterocyclic ring or saturated, partially unsaturated, or aromatic 7- to 11-membered heterocyclic ring system contains 1, 2, 3, or 4 ring members independently selected from the group consisting of $N(R^c)_p$, O, and S;
    wherein 1 or more S ring members of the saturated, partially unsaturated, or aromatic 3- to 10-membered heterocyclic ring or saturated, partially unsaturated, or aromatic 7- to 11-membered heterocyclic ring system are optionally and independently oxidized; and
    wherein the $C_1$-$C_8$ alkyl, alkyl-$C_7$-$C_{10}$ cycloalkyl, alkyl-($C_5$-$C_{10}$ alkylcycloalkyl), $C_2$-$C_8$ alkenyl, $C_2$-$C_8$ alkynyl, cycloalkyl-$C_7$-$C_{14}$ cycloalkyl, saturated, partially unsaturated, or aromatic 3- to 10-membered carbocyclic or heterocyclic ring, or saturated, partially unsaturated, or aromatic 7- to 11-membered carbocyclic or heterocyclic ring system is optionally substituted with 1, 2, 3, 4, or 5 independently selected $R^{2a}$ substituents;
  each $R^{2a}$ is independently halogen, CN, $NO_2$, $C_1$-$C_6$ alkyl, $C_2$-$C_4$ alkenyl, $C_2$-$C_4$ alkynyl, $C(NNR^bR^c)R^b$, $C(NNR^cC(O)O_pR^c)R^b$, $C(NO_pR_b)R_b$, $C(O)NR^bR^c$, $C(O)O_pR^c$, $C(S)NR^bR^c$, $NR^bR^c$, $N(CR^bR^c)$, $NR^bC(NR^b)NR^bR^c$, $NR^bC(O)NR^bR^c$, $NR^bC(O)O_pR^e$, $NR^bC(S)NR^bR^c$, $NR^bN(CR^bR^c)$, $NR^bNR^bR^c$, $NR^bNR^bC(X^2)NR^bR^c$, $NR^bNR^bS(O)_2NR^bR^c$, $NR^bS(O)_2R^c$, $NR^bS(O)_2NR^bR^c$, $N[S(O)_pR^c]R^c$, OCN, $OR^e$, $OC_5$-$C_6$ alkyl, $OC_5$-$C_6$ haloalkyl, $OC(O)NR^bR^e$, $OC(O)O_pR^e$, $ONR^bR^c$, $ON(CR^bR^c)$, $OP(X^2)(O_pR^c)R^b$, $OP(X^2)(OR^c)_2$, $OS(O)_2R^c$, $OS(O)_2NR^bR^c$, $P(X^2)R^bR^c$, SCN, $SF_5$, $S(O)_mR^b$, $S(O)_o(NR^b)_qR^c$, $S(O)_2NR^bR^c$, $Si(R^d)_3$, or a saturated, partially unsaturated, or aromatic 3- to 6-membered carbocyclic or heterocyclic ring;
    wherein each saturated, partially unsaturated, or aromatic 3- to 6-membered heterocyclic ring independently contains 1, 2, or 3 ring members independently selected from the group consisting of $N(R^c)_p$, O, and S;
    wherein 1 or more S ring members of each 3- to 6-membered heterocyclic ring are optionally and independently oxidized; and
    wherein each $C_1$-$C_6$ alkyl, $C_2$-$C_4$ alkenyl, $C_2$-$C_4$ alkynyl, $OC_5$-$C_6$ alkyl, $OC_5$-$C_6$ haloalkyl, and saturated, partially unsaturated, or aromatic 3- to 6-membered carbocyclic or heterocyclic ring is optionally and independently substituted with 1, 2, 3, 4, or 5 independently selected $R^{2aa}$ substituents; or
    two geminal $R^{2a}$, bound together, optionally form a substituent selected from the group consisting of =$CR^bR^c$, =$NR^c$, =$NNR^cR^c$, =$NOR^c$, =O, and =S;
  $R^3$ is H, $C_1$-$C_8$ alkyl, $C_2$-$C_8$ alkenyl, $C_2$-$C_8$ alkynyl, $C(NR^c)R^c$, $C(NNR^bR^c)R^c$, $C(N[NR^cC(O)R^b])R^c$, $C(N[NR^cC(O)OR^c])R^c$, $C(NOR^c)R^c$, $C(O)R^b$, $C(O)NR^bR^c$, $C(O)OC(O)C_1$-$C_4$ alkyl, $C(O)OC_3$-$C_6$ cycloalkyl, C(O)O-(saturated, partially unsaturated, or aromatic 3- to 6-membered carbocyclic or heterocyclic ring), $C(S)NR^bR^c$, $NR^bR^c$, $N(CR^bR^c)$, $NR^cC(O)R^c$, $NR^cC(O)NR^bR^c$, $NR^cC(O)OR^e$, $NR^cS(O)_2R^b$, $NR^cS(O)_2NR^bR^c$, $OC(O)R^c$, $OC(O)NR^bR^e$, $OC(O)OR^e$, $S(O)_o(NR^b)_qR^c$, $S(O)_2NR^bR^c$, $Si(R^d)_3$, cycloalkyl-$C_7$-$C_{14}$ cycloalkyl, or a saturated, partially unsaturated, or aromatic 3- to 11-membered carbocyclic or heterocyclic ring or ring system;
wherein the saturated, partially unsaturated, or aromatic 3- to 11-membered heterocyclic ring or ring system contains 1, 2, 3, or 4 ring members independently selected from the group consisting of $N(R^c)_p$, O, and S;
wherein 1 or more S ring members of the 3- to 11-membered heterocyclic ring or ring system are optionally and independently oxidized; and
wherein the $C_1$-$C_8$ alkyl, $C_2$-$C_8$ alkenyl, $C_2$-$C_8$ alkynyl, cycloalkyl-$C_7$-$C_{14}$ cycloalkyl, or saturated, partially unsaturated, or aromatic 3- to 11-membered carbocyclic or heterocyclic ring or ring system is optionally substituted with 1, 2, 3, 4, or 5 independently selected $R^a$ substituents;
each $R^a$ is independently halogen, CN, $NO_2$, $C_1$-$C_6$ alkyl, $C_2$-$C_4$ alkenyl, $C_2$-$C_4$ alkynyl, $C(O)NR^bR^c$, $C(O)O_pR^c$, $C(S)NR^bR^c$, $NR^bR^c$, $NR^bC(O)NR^bR^c$, $NR^bC(O)O_pR^e$, $NR^bS(O)_2R^c$, $NR^bS(O)_2NR^bR^c$, $N[S(O)_pR_c]R_c$, OCN, $OR^c$, $OC_5$-$C_6$ alkyl, $OC_5$-$C_6$ haloalkyl, $OC(O)NR^bR^e$, $OC(O)O_pR^e$, $OS(O)_2R^c$, $OS(O)_2NR^bR^c$, SCN, $SF_5$, $S(O)_mR^b$, $S(O)_o(NR^b)_qR^c$, $S(O)_2NR^bR^c$, $Si(R^d)_3$, or a saturated, partially unsaturated, or aromatic 3- to 6-membered carbocyclic or heterocyclic ring;
wherein each saturated, partially unsaturated, or aromatic 3- to 6-membered heterocyclic ring independently contains 1, 2, or 3 ring members independently selected from the group consisting of $N(R^c)_p$, O, and S;
wherein 1 or more S ring members of each 3- to 6-membered heterocyclic ring are optionally and independently oxidized; and
wherein each $C_1$-$C_6$ alkyl, $C_2$-$C_4$ alkenyl, $C_2$-$C_4$ alkynyl, $OC_5$-$C_6$ alkyl, $OC_5$-$C_6$ haloalkyl, and saturated, partially unsaturated, or aromatic 3- to 6-membered carbocyclic or heterocyclic ring is optionally and independently substituted with 1, 2, 3, 4, or 5 independently selected $R^{aa}$ substituents; or
two geminal $R^a$, bound together, optionally form a substituent selected from the group consisting of $=CR^bR^c$, $=NR^c$, $=NNR^cR^c$, $=NOR^c$, $=O$, and $=S$;
each $R^b$ is independently H, $C_1$-$C_6$ alkyl, $C_1$-$C_6$ haloalkyl, $OC_1$-$C_6$ alkyl, $OC_1$-$C_6$ haloalkyl, or a saturated, partially unsaturated, or aromatic 3- to 6-membered carbocyclic or heterocyclic ring;
wherein each saturated, partially unsaturated, or aromatic 3- to 6-membered heterocyclic ring independently contains 1, 2, or 3 ring members independently selected from the group consisting of $N(R^c)_p$, O, and S;
wherein 1 or more S ring members of each 3- to 6-membered heterocyclic ring are optionally and independently oxidized; and
wherein each $C_1$-$C_6$ alkyl, $C_1$-$C_6$ haloalkyl, $OC_1$-$C_6$ alkyl, $OC_1$-$C_6$ haloalkyl, and saturated, partially unsaturated, or aromatic 3- to 6-membered carbocyclic or heterocyclic ring is optionally and independently substituted with 1, 2, 3, 4, or 5 independently selected $R^{aa}$ substituents;
each $R^c$ is independently H, $C_1$-$C_4$ alkyl, $C_1$-$C_4$ haloalkyl, $C(O)C_1$-$C_4$ alkyl, or a saturated, partially unsaturated, or aromatic 3- to 6-membered carbocyclic or heterocyclic ring;
wherein each saturated, partially unsaturated, or aromatic 3- to 6-membered heterocyclic ring independently contains 1, 2, or 3 ring members independently selected from the group consisting of $N(R^c)_p$, O, and S;
wherein 1 or more S ring members of each 3- to 6-membered heterocyclic ring are optionally and independently oxidized; and
wherein each saturated, partially unsaturated, or aromatic 3- to 6-membered carbocyclic or heterocyclic ring is optionally and independently substituted with 1, 2, 3, 4, or 5 independently selected $R^{aa}$ substituents; or
two geminal $R^b$, together with the atom to which they are attached, optionally and independently form a saturated, partially unsaturated, or aromatic 3- to 7-membered carbocyclic or heterocyclic ring;
wherein each saturated, partially unsaturated, or aromatic 3- to 7-membered heterocyclic ring contains 1 or 2 ring members independently selected from the group consisting of N, $N^+O^-$, O, S, S(O), and $S(O)_2$; and
wherein each saturated, partially unsaturated, or aromatic 3- to 7-membered carbocyclic or heterocyclic ring is optionally and independently substituted with 1, 2, 3, 4, or 5 independently selected $R^{bb}$ substituents; or
two geminal $R^b$ and $R^c$, together with the atom to which they are attached, optionally and independently form a saturated, partially unsaturated, or aromatic 3- to 7-membered carbocyclic or heterocyclic ring;
wherein each saturated, partially unsaturated, or aromatic 3- to 7-membered heterocyclic ring contains 1 or 2 ring members independently selected from the group consisting of N, $N^+O^-$, O, S, S(O), and $S(O)_2$; and
wherein each saturated, partially unsaturated, or aromatic 3- to 7-membered carbocyclic or heterocyclic ring is optionally and independently substituted with 1, 2, 3, 4, or 5 independently selected $R^{bb}$ substituents; or
two geminal $R^c$, together with the atom to which they are attached, optionally and independently form a saturated, partially unsaturated, or aromatic 3- to 7-membered carbocyclic or heterocyclic ring;
wherein each saturated, partially unsaturated, or aromatic 3- to 7-membered heterocyclic ring contains 1 or 2 ring members independently selected from the group consisting of N, $N^+O^-$, O, S, S(O), and $S(O)_2$; and
wherein each saturated, partially unsaturated, or aromatic 3- to 7-membered carbocyclic or heterocyclic ring is optionally and independently substituted with 1, 2, 3, 4, or 5 independently selected $R^{bb}$ substituents;
each $R^d$ is independently H, $C_1$-$C_6$ alkyl, alkyl-$OC_1$-$C_6$ alkyl, $C_2$-$C_6$ alkenyl, $C_2$-$C_6$ alkynyl, $C_3$-$C_6$ cycloalkyl, or phenyl;
wherein each $C_1$-$C_6$ alkyl, alkyl-$OC_1$-$C_6$ alkyl, $C_2$-$C_6$ alkenyl, $C_2$-$C_6$ alkynyl, $C_3$-$C_6$ cycloalkyl, and phenyl is optionally and independently substituted with 1, 2, 3, 4, or 5 independently selected halogen substituents;
each $R^e$ is independently $C_1$-$C_4$ alkyl, $C_1$-$C_4$ haloalkyl, $C(O)C_1$-$C_4$ alkyl, or a saturated, partially unsaturated, or aromatic 3- to 6-membered carbocyclic or heterocyclic ring;

wherein each saturated, partially unsaturated, or aromatic 3- to 6-membered heterocyclic ring independently contains 1, 2, or 3 ring members independently selected from the group consisting of $N(R^{aa})_p$, O, and S;

wherein 1 or more S ring members of each 3- to 6-membered heterocyclic ring are optionally and independently oxidized; and wherein each saturated, partially unsaturated, or aromatic 3- to 6-membered carbocyclic or heterocyclic ring is optionally and independently substituted with 1, 2, 3, 4, or 5 independently selected $R^{aa}$ substituents;

each $R^{aa}$ is independently halogen, $C_1$-$C_6$ alkyl, $C_1$-$C_6$ haloalkyl, $OC_1$-$C_6$ alkyl, or $OC_1$-$C_6$ haloalkyl;

each $R^{bb}$ is independently halogen, CN, $NO_2$, $C_1$-$C_6$ alkyl, $C_1$-$C_6$ haloalkyl, $C_2$-$C_4$ alkenyl, $C_2$-$C_4$ alkynyl, $C(NNR^bR^c)R^b$, $C(NNR^cC(O)O_pR^c)R^b$, $C(NO_pR_b)R_b$, $C(O)NR^bR^c$, $C(O)O_pR^c$, $C(S)NR^bR^c$, $NR^bR^c$, $N(CR^bR^c)$, $NR^bC(NR^b)NR^bR^c$, $NR^bC(O)NR^bR^c$, $NR^bC(O)O_pR^e$, $NR^bC(S)NR^bR^c$, $NR^bN(CR^bR^c)$, $NR^bNR^bR^c$, $NR^bNR^bC(X^2)NR^bR^c$, $NR^bNR^bS(O)_2NR^bR^c$, $NR^bS(O)_2R^c$, $NR^bS(O)_2NR^bR^c$, $N[S(O)_pR^c]R^c$, OCN, $OR^c$, $OC_5$-$C_6$ alkyl, $OC_5$-$C_6$ haloalkyl, $OC(O)NR^bR^e$, $OC(O)O_pR^e$, $ONR^bR^c$, $ON(CR^bR^c)$, $OP(X^2)(O_pR^c)R^b$, $OP(X^2)(OR^c)_2$, $OS(O)_2R^c$, $OS(O)_2NR^bR^c$, $P(X^2)R^bR^c$, SCN, $SF_5$, $S(O)_mR^b$, $S(O)_o(NR^b)_qR^c$, $S(O)_2NR^bR^c$, $Si(R^d)_3$, or $C_3$-$C_6$ cycloalkyl; or two geminal $R^{bb}$, bound together, optionally form a substituent selected from the group consisting of $=CR^bR^c$, $=NR^c$, $=NNR^cR^c$, $=NOR^c$, $=O$, and $=S$;

each $R^{2aa}$ is independently halogen, CN, $NO_2$, $C_1$-$C_6$ alkyl, $C_1$-$C_6$ haloalkyl, $C_2$-$C_4$ alkenyl, $C_2$-$C_4$ alkynyl, $C(NNR^bR^c)R^b$, $C(NNR^cC(O)O_pR^c)R^b$, $C(NO_pR^b)R^b$, $C(O)NR^bR^c$, $C(O)O_pR^c$, $C(S)NR^bR^c$, $NR^bR^c$, $N(CR^bR^c)$, $NR^bC(NR^b)NR^bR^c$, $NR^bC(O)NR^bR^c$, $NR^bC(O)O_pR^e$, $NR^bC(S)NR^bR^c$, $NR^bN(CR^bR^c)$, $NR^bNR^bR^c$, $NR^bNR^bC(X^2)NR^bR^c$, $NR^bNR^bS(O)_2NR^bR^c$, $NR^bS(O)_2R^c$, $NR^bS(O)_2NR^bR^c$, $N[S(O)_pR^c]R^c$, OCN, $OR^c$, $OC_5$-$C_6$ alkyl, $OC_5$-$C_6$ haloalkyl, $OC(O)NR^bR^e$, $OC(O)O_pR^e$, $ONR^bR^c$, $ON(CR^bR^c)$, $OP(X^2)(O_pR^c)R^b$, $OP(X^2)(OR^c)_2$, $OS(O)_2R^c$, $OS(O)_2NR^bR^c$, $P(X^2)R^bR^c$, SCN, $SF_5$, $S(O)_mR^b$, $S(O)_o(NR^b)_qR^c$, $S(O)_2NR^bR^c$, $Si(R^d)_3$, or $C_3$-$C_6$ cycloalkyl; or two geminal $R^{2aa}$, bound together, optionally form a substituent selected from the group consisting of $=CR^bR^c$, $=NR^c$, $=NNR^cR^c$, $=NOR^c$, $=O$, and $=S$;

each $X^2$ is independently O or S;
each m is independently 0, 1 or 2;
each o is independently 0, 1 or 2;
each p is independently 0 or 1; and
each q is independently 0, 1 or 2;

with the provisos that:
(1) the sum of o and q is 0, 1 or 2 for the 3- to 10-membered heterocyclic ring or 7- to 11-membered heterocyclic ring system of Het; and
(2) if $R^2$ is halogen or CN, then Z is a direct bond.

2. The compound according to claim 1, or a stereoisomer thereof, wherein the stereoisomer of the compound has formula (I-R):

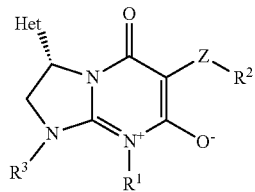

(I-R)

or an agriculturally or veterinary acceptable salt or tautomer thereof.

3. The compound according to claim 1, or an agriculturally or veterinary acceptable salt, stereoisomer, or tautomer thereof, wherein:

Het is D-2, D-9, or D-27:

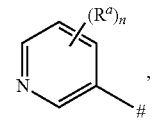

D-2

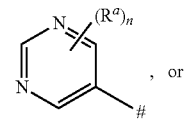

, or D-9

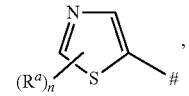

D-27 wherein:
each $R^a$ is independently halogen, $C_1$-$C_4$ haloalkyl, $OC_1$-$C_4$ alkyl, $SC_1$-$C_4$ alkyl, or phenyl;
n is 0, 1, or 2; and
# is the point of attachment to the remainder of formula (I).

4. The compound according to claim 3, or an agriculturally or veterinary acceptable salt, stereoisomer, or tautomer thereof, wherein:
each $R^a$ is independently halogen; and
n is 0 or 1.

5. The compound according to claim 1, or an agriculturally or veterinary acceptable salt, stereoisomer, or tautomer thereof, wherein Z is a direct bond.

6. The compound according to claim 1, or an agriculturally or veterinary acceptable salt, stereoisomer, or tautomer thereof, wherein $R^1$ is $C_1$-$C_4$ alkyl, $CH_2$-phenyl, $C_1$-$C_4$ haloalkyl, $C_2$-$C_4$ alkenyl, $C_3$-$C_6$ cycloalkyl, or phenyl.

7. The compound according to claim 1, or an agriculturally or veterinary acceptable salt, stereoisomer, or tautomer thereof, wherein:
$R^2$ is a saturated, partially unsaturated, or aromatic 5- or 6-membered carbocyclic or heterocyclic ring;
wherein the saturated, partially unsaturated, or aromatic 5- or 6-membered carbocyclic or heterocyclic ring contains 1, 2, 3, or 4 ring members independently selected from the group consisting of $N(R^c)_p$, O, and S;
wherein 1 or more S ring members of the saturated, partially unsaturated, or aromatic 5- or 6-membered heterocyclic ring are optionally and independently oxidized; and wherein the saturated, partially unsaturated, or aromatic 5- or 6-membered carbocyclic or heterocyclic ring is optionally substituted with 1, 2, 3, 4, or 5 independently selected $R^{2a}$ substituents;

each $R^{2a}$ is independently halogen, $C_1$-$C_6$ haloalkyl, C(O)NR$^b$R$^c$, C(O)OR$^c$, OR$^c$, phenyl, or pyridyl;
wherein each phenyl or pyridyl is optionally and independently substituted with 1, 2, 3, 4, or 5 independently selected $R^{2aa}$ substituents;

each $R^{2aa}$ is independently halogen, $C_1$-$C_6$ haloalkyl, or OC$_1$-$C_6$ alkyl;

each $R^b$ is independently H, $C_1$-$C_4$ alkyl, $C_1$-$C_4$ haloalkyl, or $C_3$-$C_6$ cycloalkyl; and each $R^c$ is independently H, $C_1$-$C_4$ alkyl, or $C_1$-$C_4$ haloalkyl; or two geminal $R^b$ and $R^c$, together with the atom to which they are attached, optionally and independently form a saturated, partially unsaturated, or aromatic 3- to 7-membered carbocyclic or heterocyclic ring;
wherein each saturated, partially unsaturated, or aromatic 3- to 7-membered heterocyclic ring contains 1 or 2 ring members independently selected from the group consisting of N, N$^+$O$^-$, O, S, S(O), and S(O)$_2$; and
wherein each saturated, partially unsaturated, or aromatic 3- to 7-membered carbocyclic or heterocyclic ring is optionally and independently substituted with 1, 2, 3, 4, or 5 independently selected $R^{bb}$ substituents.

8. The compound according to claim 1, or an agriculturally or veterinary acceptable salt, stereoisomer, or tautomer thereof, wherein $R^2$ is phenyl;
wherein the phenyl is optionally substituted with 1, 2, 3, 4, or 5 independently selected $R^{2a}$ substituents.

9. The compound according to claim 1, or an agriculturally or veterinary acceptable salt, stereoisomer, or tautomer thereof, wherein:
$R^3$ is $C_1$-$C_6$ alkyl, CH$_2$-phenyl, $C_2$-$C_4$ alkenyl, C(NR$^c$)R$^c$, C(NNR$^b$R$^c$)R$^c$, C(NOR$^c$)R$^c$, C(O)R$^b$, C(O)NR$^b$R$^c$, C(O)OC(O)C$_1$-$C_4$ alkyl, C(O)OC$_3$-$C_6$ cycloalkyl, C(O)O-(saturated, partially unsaturated, or aromatic 3- to 6-membered carbocyclic or heterocyclic ring), C(S)NR$^b$R$^c$, S(O)$_2$NR$^b$R$^c$, $C_3$-$C_6$ cycloalkyl, or phenyl;
wherein the $C_1$-$C_6$ alkyl, CH$_2$-phenyl, $C_2$-$C_4$ alkenyl, $C_3$-$C_6$ cycloalkyl, or phenyl is optionally substituted with 1, 2, 3, 4, or 5 independently selected $R^a$ substituents; and
each $R^a$ is independently halogen or $C_1$-$C_4$ alkyl.

10. The compound according to claim 1, or an agriculturally or veterinary acceptable salt, stereoisomer, or tautomer thereof, wherein:
Het is D-1, D-2, D-9, or D-27:

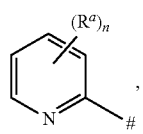

D-1

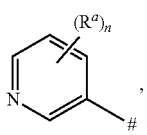

D-2

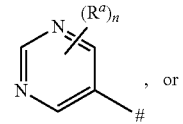

D-9

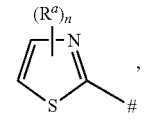

D-27 wherein:
$R^a$ is halogen, $C_1$-$C_4$ haloalkyl, OC$_1$-$C_4$ alkyl, SC$_1$-$C_4$ alkyl, or phenyl;
n is 1; and
# is the point of attachment to the remainder of formula (I);
Z is a direct bond;
$R^1$ is $C_1$-$C_4$ alkyl or CH$_2$-phenyl;
$R^2$ is CH$_2$-phenyl, CH(CH$_3$)-phenyl, or phenyl;
wherein the phenyl is optionally substituted with 1, 2, 3, 4, or 5 independently selected $R^{2a}$ substituents;
each $R^{2a}$ is independently halogen, CN, $C_1$-$C_3$ alkyl, $C_1$-$C_3$ haloalkyl, OC$_1$-$C_3$ alkyl, or OC$_1$-$C_3$ haloalkyl; and
$R^3$ is $C_1$-$C_3$ alkyl or C(O)OC$_1$-$C_4$ alkyl.

11. A seed comprising a compound according to claim 1, or an agriculturally or veterinary acceptable salt, stereoisomer, or tautomer thereof.

12. A pesticidal mixture comprising a compound according to claim 1, or an agriculturally or veterinary acceptable salt, stereoisomer, or tautomer thereof, and an additional agrochemically active ingredient.

13. The pesticidal mixture according to claim 12, wherein the additional agrochemically active ingredient is a pesticide.

14. The pesticidal mixture according to claim 13, wherein the pesticide is a fungicide or an insecticide.

15. The pesticidal mixture according to claim 12, wherein the pesticidal mixture further comprises an agriculturally or veterinary acceptable liquid carrier or solid carrier.

16. An agrochemical or veterinary composition comprising a compound according to claim 1, or an agriculturally or veterinary acceptable salt, stereoisomer, or tautomer thereof, and an agriculturally or veterinary acceptable carrier or diluent.

17. A method for protection of plant propagation material, wherein the method comprises contacting the plant propagation material with a pesticidally effective amount of a compound according to claim 1, or an agriculturally or veterinary acceptable salt, stereoisomer, or tautomer thereof.

18. A method for protection of plant propagation material, wherein the method comprises contacting the plant propagation material with a pesticidally effective amount of a pesticidal mixture according to claim 12.

19. A method for protecting plants from attack by invertebrate pests or infestation by invertebrate pests, wherein the method comprises contacting the plant, the soil in which the plant is growing, or the water in which the plant is growing with a pesticidally effective amount of a compound according to claim 1, or an agriculturally or veterinary acceptable salt, stereoisomer, or tautomer thereof.

20. A method for protecting plants from attack by invertebrate pests or infestation by invertebrate pests, wherein the method comprises contacting the plant, the soil in which the plant is growing, or the water in which the plant is growing with a pesticidally effective amount of a pesticidal mixture according to claim 12.

21. A method for controlling invertebrate pests, infestation by invertebrate pests, or infection by invertebrate pests, wherein the method comprises contacting the pests, their food supply, their habit, their breeding grounds, or their locus with a pesticidally effective amount of a compound according to claim 1, or an agriculturally or veterinary acceptable salt, stereoisomer, or tautomer thereof.

22. A method for controlling invertebrate pests, infestation by invertebrate pests, or infection by invertebrate pests, wherein the method comprises contacting the pests, their food supply, their habit, their breeding grounds, or their locus with a pesticidally effective amount of a pesticidal mixture according to claim 12.

\* \* \* \* \*

UNITED STATES PATENT AND TRADEMARK OFFICE
CERTIFICATE OF CORRECTION

PATENT NO. : 11,399,543 B2
APPLICATION NO. : 16/652700
DATED : August 2, 2022
INVENTOR(S) : Joachim Dickhaut et al.

Page 1 of 1

It is certified that error appears in the above-identified patent and that said Letters Patent is hereby corrected as shown below:

In the Claims

At Column 96, Line 25, "$C(NO_pR_b)R_b$," should be -- $C(NO_pR^b)R^b$, --.

At Column 96, Lines 64-65, "$NR^cS(O)_2R^6$," should be -- $NR^cS(O)_2R^b$, --.

At Column 97, Lines 20-21, "$N[S(O)_pR_c]R_c$," should be -- $N[S(O)_pR^c]R^c$, --.

At Column 99, Lines 19-20, "$C(NO_pR_b)R_b$," should be -- $C(NO_pR^b)R^b$, --.

At Column 100, Lines 31-34, "  " should be --  --.

At Column 102, Lines 8-13, "  " should be --  --.

Signed and Sealed this
Seventh Day of February, 2023

Katherine Kelly Vidal
*Director of the United States Patent and Trademark Office*